United States Patent
Bannen et al.

(10) Patent No.: US 7,977,345 B2
(45) Date of Patent: Jul. 12, 2011

(54) C-MET MODULATORS AND METHOD OF USE

(75) Inventors: Lynne Canne Bannen, Pacifica, CA (US); Diva Sze-Ming Chan, San Francisco, CA (US); Lisa Esther Dalrymple, San Leandro, CA (US); Vasu Jammalamadaka, Pleasanton, CA (US); Richard George Khoury, Redwood City, CA (US); James William Leahy, San Leandro, CA (US); Morrisson B. Mac, San Francisco, CA (US); Grace Mann, Brisbane, CA (US); Larry W. Mann, Richland, MI (US); John M. Nuss, Danville, CA (US); Jason Jevious Parks, Sacramento, CA (US); Yong Wang, Foster City, CA (US); Wie Xu, Danville, CA (US)

(73) Assignee: Exelixis, Inc., South San Francisco, CA (US)

( * ) Notice: Subject to any disclaimer, the term of this patent is extended or adjusted under 35 U.S.C. 154(b) by 1096 days.

(21) Appl. No.: 11/571,140

(22) PCT Filed: Jul. 1, 2005

(86) PCT No.: PCT/US2005/023364
§ 371 (c)(1),
(2), (4) Date: Dec. 21, 2006

(87) PCT Pub. No.: WO2006/014325
PCT Pub. Date: Feb. 9, 2006

(65) Prior Publication Data
US 2007/0179130 A1    Aug. 2, 2007

Related U.S. Application Data

(60) Provisional application No. 60/584,977, filed on Jul. 2, 2004.

(51) Int. Cl.
C07D 487/04 (2006.01)
A61K 31/519 (2006.01)
A61K 31/522 (2006.01)

(52) U.S. Cl. .............. 514/265.1; 544/280; 544/262; 544/265; 514/262.1; 514/263.23; 514/263.3

(58) Field of Classification Search ............ 544/280; 514/265.1
See application file for complete search history.

(56) References Cited

U.S. PATENT DOCUMENTS

| 6,448,261 B1 | 9/2002 | Bakthavatchalam et al. |
| 7,439,246 B2 * | 10/2008 | Borzilleri et al. ......... 514/258.1 |
| 2004/0053908 A1 | 3/2004 | Funahashi et al. |

FOREIGN PATENT DOCUMENTS

| EP | 0795556 A1 | 9/1997 |
| EP | 1411046 A1 | 4/2004 |
| WO | 95/19774 A | 7/1995 |
| WO | WO 2004/018473 A2 | 4/2004 |
| WO | 2005/005389 A | 1/2005 |

OTHER PUBLICATIONS

Vippagunta et. al. (Advanced Drug Delivery Reviews, 2001, 48, pp. 3/26).*
Shealy et al., "v-Triazolo[4,5-d]pyrimidines. II. O-Substituted Derivatives of 8-Azaguanine and 8-Azahypoxanthine," J. Organic Chemistry, vol. 27, pp. 4518-4523 (1962).
Laufer et al., "Synthesis and biological testing of purine derivatives as potential ATP-competitive kinase inhibitors," J. Med. Chem., 48 (3): 710-722 (Feb. 10, 2005).
Myers et al., "The preparation and SAR of 4-(-anilino)-quinazolines: p56Ick and EGF-R tyrosine kinase activity," Bioorg. Med. Chem. Lett., 7 (4): 417-420 (Feb. 18, 1997).
Norman et al., "4-(Heteroarylthio)-2-byphenylyltetrazoles as nonpeptide angiotensin II antagonists," J. Med. Chem., 38 (23): 4670-4678 (Nov. 10, 1995).

* cited by examiner

*Primary Examiner* — Susanna Moore
(74) *Attorney, Agent, or Firm* — Honigman Miller Schwartz and Cohn; Heidi M. Berven; Jonathan P. O'Brien

(57) ABSTRACT

A compound for modulating kinase activity according to Formula I,

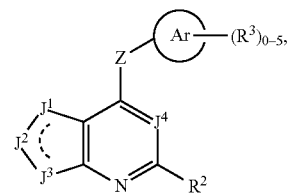

or a pharmaceutically acceptable salt thereof, Wherein $J^1$, $J^2$, $J^3$, $R^2$, $J^4$, Z, Ar and $R^3$ are as defined in the specification, compositions thereof, and methods of use thereof.

3 Claims, No Drawings

C-MET MODULATORS AND METHOD OF USE

REFERENCE TO RELATED APPLICATIONS

This application claims priority to U.S. provisional patent application 60/584,977 filed Jul. 2, 2004. The contents of the prior application are hereby incorporated in their entirety.

BACKGROUND OF THE INVENTION

1. Field of the Invention

This invention relates to compounds for modulating protein kinase enzymatic activity for modulating cellular activities such as proliferation, differentiation, programmed cell death, migration and chemoinvasion. Even more specifically, the invention relates to quinazolines and quinolines which inhibit, regulate and/or modulate kinase receptor signal transduction pathways related to the changes in cellular activities as mentioned above, compositions which contain these compounds, and methods of using them to treat kinase-dependent diseases and conditions.

2. Summary of Related Art

Improvements in the specificity of agents used to treat cancer is of considerable interest because of the therapeutic benefits which would be realized if the side effects associated with the administration of these agents could be reduced. Traditionally, dramatic improvements in the treatment of cancer are associated with identification of therapeutic agents acting through novel mechanisms.

Protein kinases are enzymes that catalyze the phosphorylation of proteins, in particular, hydroxy groups on tyrosine, serine and threonine residues of proteins. The consequences of this seemingly simple activity are staggering; cell differentiation and proliferation; i.e., virtually all aspects of cell life in one-way or another depend on protein kinase activity. Furthermore, abnormal protein kinase activity has been related to a host of disorders, ranging from relatively non-life threatening diseases such as psoriasis to extremely virulent diseases such as glioblastoma (brain cancer).

Protein kinases can be categorized as receptor type or non-receptor type. Receptor-type tyrosine kinases have an extracellular, a transmembrane, and an intracellular portion, while non-receptor type tyrosine kinases are wholly intracellular.

Receptor-type tyrosine kinases are comprised of a large number of transmembrane receptors with diverse biological activity. In fact, about 20 different subfamilies of receptor-type tyrosine kinases have been identified. One tyrosine kinase subfamily, designated the HER subfamily, is comprised of EGFR (HER1), HER2, HER3, and HER4. Ligands of this subfamily of receptors identified so far include epithelial growth factor, TGF-alpha, amphiregulin, HB-EGF, betacellulin and heregulin. Another subfamily of these receptor-type tyrosine kinases is the insulin subfamily, which includes INS-R, IGF-IR, and IR-R. The PDGF subfamily includes the PDGF-alpha and beta receptors, CSFIR, c-Kit and FLK-II. Then there is the FLK family, which is comprised of the kinase insert domain receptor (KDR), fetal liver kinase-1 (FLK-1), fetal liver kinase-4 (FLK-4) and the fms-like tyrosine kinase-1 (flt-1). The PDGF and FLK families are usually considered together due to the similarities of the two groups. For a detailed discussion of the receptor-type tyrosine kinases, see Plowman et al., DN&P 7(6): 334-339, 1994, which is hereby incorporated by reference.

The non-receptor type of tyrosine kinases is also comprised of numerous subfamilies, including Src, Frk, Btk, Csk, Abl, Zap70, Fes/Fps, Fak, Jak, Ack, and LIMK. Each of these subfamilies is further sub-divided into varying receptors. For example, the Src subfamily is one of the largest and includes Src, Yes, Fyn, Lyn, Lck, Blk, Hck, Fgr, and Yrk. The Src subfamily of enzymes has been linked to oncogenesis. For a more detailed discussion of the non-receptor type of tyrosine kinases, see Bolen, Oncogene, 8:2025-2031 (1993), which is hereby incorporated by reference.

Since protein kinases and their ligands play critical roles in various cellular activities, deregulation of protein kinase enzymatic activity can lead to altered cellular properties, such as uncontrolled cell growth associated with cancer. In addition to oncological indications, altered kinase signaling is implicated in numerous other pathological diseases. These include, but are not limited to: immunological disorders, cardiovascular diseases, inflammatory diseases, and degenerative diseases. Therefore, both receptor and non-receptor protein kinases are attractive targets for small molecule drug discovery.

One particularly attractive goal for therapeutic use of kinase modulation relates to oncological indications. For example, modulation of protein kinase activity for the treatment of cancer has been demonstrated successfully with the FDA approval of Gleevec® (imatinib mesylate, produced by Novartis Pharmaceutical Corporation of East Hanover, N.J.) for the treatment of Chronic Myeloid Leukemia (CML) and gastrointestinal stroma cancers (GIST). Gleevec is a c-Kit and Abl kinase inhibitor.

Modulation (particularly inhibition) of cell proliferation and angiogenesis, two key cellular processes needed for tumor growth and survival (Matter A. Drug Disc Technol 2001 6, 1005-1024), is an attractive goal for development of small-molecule drugs. Anti-angiogenic therapy represents a potentially important approach for the treatment of solid tumors and other diseases associated with dysregulated vascularization, including ischemic coronary artery disease, diabetic retinopathy, psoriasis and rheumatoid arthritis. As well, cell antiproliferative agents are desirable to slow or stop the growth of tumors.

One particularly attractive target for small-molecule modulation, with respect to antiangiogenic and antiproliferative activity is c-Met. The kinase, c-Met, is the prototypic member of a subfamily of heterodimeric receptor tyrosine kinases (RTKs) which include Met, Ron and Sea. Expression of c-Met occurs in a wide variety of cell types including epithelial, endothelial and mesenchymal cells where activation of the receptor induces cell migration, invasion, proliferation and other biological activities associated with "invasive cell growth." As such, signal transduction through c-Met receptor activation is responsible for many of the characteristics of tumor cells.

The endogenous ligand for c-Met is the hepatocyte growth factor (HGF), a potent inducer of angiogenisis, also known as "scatter factor" (SF). Binding of HGF to c-Met induces activation of the receptor via autophosphorylation resulting in an increase of receptor dependent signaling, which promotes cell growth and invasion. Anti-HGF antibodies or HGF antagonists have been shown to inhibit tumor metastasis in vivo (See: Maulik et al Cytokine & Growth Factor Reviews 2002 13, 41-59).

Tumor growth progression requires the recruitment of new blood vessels into the tumor from preexisting vessels as well as invasion, adhesion and proliferation of malignant cells. Accordingly, c-Met overexpression has been demonstrated on a wide variety of tumor types including breast, colon, renal, lung, squamous cell myeloid leukemia, hemangiomas, melanomas, astrocytomas, and glioblastomas. Additionally activating mutations in the kinase domain of c-Met have been identified in hereditary and sporadic renal papilloma and squamous cell carcinoma. (See: Maulik et al Cytokine & growth Factor reviews 2002 13, 41-59; Longati et al Curr Drug Targets 2001, 2, 41-55; Funakoshi et al Clinica Chimica Acta 2003 1-23). Thus modulation of c-Met is desirable as a means to treat cancer and cancer-related disease.

The Eph receptors comprise the largest family of receptor tyrosine kinases and are divided into two groups, EphA and EphB, based on their sequence homology. The ligands for the Eph receptors are ephrin, which are membrane anchored. Ephrin A ligands bind preferentially to EphA receptors whilst ephrin B ligands bind to EphB receptors. Binding of ephrin to Eph receptors causes receptor autophosphorylation and typically requires a cell-cell interaction since both receptor and ligand are membrane bound.

Overexpression of Eph receptors has been linked to increased cell proliferation in a variety of tumors (Zhou R 1998 Pharmacol Ther. 77, 151-181; Kiyokawa E, Takai S, Tanaka M et al 1994 Cancer Res 54, 3645-3650; Takai N Miyazaki T, Fujisawa K, Nasu K and Miyakawa. 2001 Oncology reports 8, 567-573). The family of Eph receptor tyrosine kinases and their ephrin ligands play important roles in a variety of processes during embryonic development and also in pathological angiogenesis and potentially metastasis. Therefore modulation of Eph receptor kinase activity should provide means to treat or prevent disease states associated with abnormal cell proliferation such as those described above.

Inhibition of EGF, VEGF and ephrin signal transduction will prevent cell proliferation and angiogenesis, two key cellular processes needed for tumor growth and survival (Matter A. Drug Disc. Technol. 2001 6, 1005-1024). EGF and VEGF receptors are previously described targets for small molecule inhibition. KDR and flt-4 are both VEGF receptors Flt-3 is normally expressed on hematopoietic progenitor cells and a subset of mature myeloid and lymphoid cells, where it modulates cell survival and proliferation. Flt-3 is constitutively activated via mutation, either in the juxtamembrane region or in the activation loop of the kinase domain, in a large proportion of patients with AML (Reilly Leuk Lymphoma 2003 44: 1-7). Also, mutations in flt-3 are significantly correlated with poor prognosis in AML patients (Sawyers Cancer Cell 2002 1: 413-415).

Accordingly, the identification of small-molecule compounds that specifically inhibit, regulate and/or modulate the signal transduction of kinases, particularly including c-Met, KDR, and flt-3, is desirable as a means to treat or prevent disease states associated with abnormal cell proliferation and angiogenesis, and is an object of this invention.

SUMMARY OF THE INVENTION

In one aspect, the present invention provides compounds for modulating kinase activity and methods of treating diseases mediated by kinase activity utilizing the compounds and pharmaceutical compositions thereof. Diseases mediated by kinase activity include, but are not limited to, diseases characterized in part by migration, invasion, proliferation and other biological activities associated with invasive cell growth. In particular to this invention is modulation, even more particularly inhibition, of c-Met, KDR, and flt-3.

In another aspect, the invention provides methods of screening for modulators of c-Met, KDR and flt-3 activity. The methods comprise combining a composition of the invention, a kinase, e.g. c-Met, KDR, or flt-3, and at least one candidate agent and determining the effect of the candidate agent on the c-Met, KDR, or flt-3, activity.

In yet another aspect, the invention also provides pharmaceutical kits comprising one or more containers filled with one or more of the ingredients of pharmaceutical compounds and/or compositions of the present invention, including, one or more kinase, e.g. c-Met, KDR, or flt-3, enzyme activity modulators as described herein. Such kits can also include, for example, other compounds and/or compositions (e.g., diluents, permeation enhancers, lubricants, and the like), a device(s) for administering the compounds and/or compositions, and written instructions in a form prescribed by a governmental agency regulating the manufacture, use or sale of pharmaceuticals or biological products, which instructions can also reflects approval by the agency of manufacture, use or sale for human administration.

In still yet another aspect, the invention also provides a diagnostic agent comprising a compound of the invention and, optionally, pharmaceutically acceptable adjuvants and excipients.

These and other features and advantages of the present invention will be described in more detail below with reference to the associated drawings.

DETAILED DESCRIPTION OF THE INVENTION

The compositions of the invention are used to treat diseases associated with abnormal and or unregulated cellular activities. Disease states which can be treated by the methods and compositions provided herein include, but are not limited to, cancer (further discussed below), immunological disorders such as rheumatoid arthritis, graft-host diseases, multiple sclerosis, psoriasis; cardiovascular diseases such as artheroscrosis, myocardioinfarction, ischemia, stroke and restenosis; other inflammatory and degenerative diseases such as interbowel diseases, osteoarthritis, macular degeneration, diabetic retinopathy.

It is appreciated that in some cases the cells may not be in a hyper- or hypo-proliferative and/or migratory state (abnormal state) and still require treatment. For example, during wound healing, the cells may be proliferating "normally", but proliferation and migration enhancement may be desired. Alternatively, reduction in "normal" cell proliferation and/or migration rate may be desired.

The present invention comprises a compound for modulating kinase activity according to Formula I,

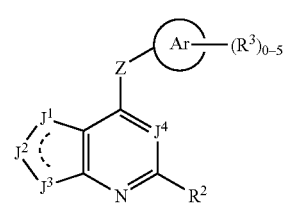

I or a pharmaceutically acceptable salt, hydrate, or prodrug thereof, wherein, each of $J^1$, $J^2$, and $J^3$ is independently selected from =N—, =C($R^1$)—, —N($R^1$)—, —O— and —S(O)$_{0-2}$—;

each $R^1$ is independently selected from —H, halogen, trihalomethyl, —CN, —NO$_2$, —OR$^{20}$, —N(R$^{20}$)R$^{20}$, —S(O)$_{0-2}$ R$^{20}$, —SO$_2$N(R$^{20}$)R$^{20}$, —CO$_2$R$^{20}$, —C(O)N(R$^{20}$)R$^{20}$, —N(R$^{20}$)SO$_2$R$^{20}$, —N(R$^{20}$)C(O)R$^{20}$, —NCO$_2$R$^{20}$, —C(O)R$^{20}$, optionally substituted C$_{1-6}$alkyl, optionally substituted aryl, optionally substituted aryl $C_{1-6}$alkyl, optionally substituted heterocyclyl, optionally substituted heterocyclyl $C_{1-6}$alkyl and —D-$R^{50}$;

$R^2$ is selected from —H, halogen, —$OR^{20}$, —$S(O)_{0-2}R^{20}$, —$NO_2$, —$N(R^{20})R^{20}$, and optionally substituted $C_{1-6}$alkyl;

$J^4$ is selected from =N—, =C(H)—, and =C(CN)—;

Ar is either a five- or six-membered arylene or a five- or six-membered heteroarylene containing between one and three heteroatoms;

each $R^3$ is independently selected from —H, halogen, trihalomethyl, —CN, —$NO_2$, —$OR^{20}$, —$N(R^{20})R^{20}$, —S$(O)_{0-2}$ $R^{20}$, —$SO_2N(R^{20})R^{20}$, —$CO_2R^{20}$, —$C(O)N(R^{20})R^{20}$, —$N(R^{20})SO_2R^{20}$, —$N(R^{20})C(O)R^{20}$, —$NCO_2R^{20}$, —$C(O)R^{20}$, optionally substituted $C_{1-6}$alkyl, optionally substituted aryl, optionally substituted aryl $C_{1-6}$alkyl, optionally substituted heterocyclyl, optionally substituted heterocyclyl $C_{1-6}$alkyl and a group —B-L-T, wherein B is selected from absent, —$N(R^{13})$—, —$N(SO_2R^{13})$—, —O—, —$S(O)_{0-2}$—, and —C(=O)—;

L is selected from absent, —C(=S)N($R^{13}$)—, —C(=$NR^{14}$)N($R^{13}$)—, —$SO_2N(R^{13})$—, —$SO_2$—, —C(=O)N($R^{13}$)—, —N($R^{13}$)—, —C(=O)$C_{1-2}$alkylN($R^{13}$)—, —N($R^{13}$)$C_{1-2}$alkylC(=O)—, —C(=O)$C_{0-1}$alkylC(=O)N($R^{13}$)—, —$C_{0-4}$alkylene-, —C(=O)$C_{0-1}$alkylC(=O)$OR^3$—, —C(=$NR^{14}$)$C_{0-1}$alkylC(=O)—, —C(=O)—, —C(=O)$C_{0-1}$alkylC(=O)—, and an optionally substituted four to six-membered heterocyclyl containing between one and three annular heteroatoms including at least one nitrogen; and T is selected from —H, —$R^{13}$, —$C_{0-4}$alkyl, —$C_{0-4}$alkylQ, —$OC_{0-4}$alkylQ, —$C_{0-4}$alkylOQ, —N($R^{13}$)$C_{0-4}$alkylQ, —$SO_2C_{0-4}$alkylQ, —C(=O)$C_{0-4}$alkylQ, —$C_{0-4}$alkylN($R^{13}$)Q, and —C(=O)N($R^{13}$)$C_{0-4}$alkylQ, wherein each of the aforementioned alkyls and alkylenes of —B-L-T is optionally substituted with one or two of $R^{60}$;

Z is selected from —$S(O)_{0-2}$—, —O—, and —$NR^4$—;

$R^4$ is either —H or optionally substituted $C_{1-6}$alkyl;

each D is independently selected from —O—, —$S(O)_{0-2}$—, and —$NR^5$—;

each $R^5$ is independently —H or optionally substituted $C_{1-6}$alkyl;

each $R^{13}$ is independently selected from —H, —C(=O)$R^{20}$, —C(=O)$OR^{20}$, —C(=O)$SR^{20}$, —$SO_2R^{20}$, —C(=O)N($R^{20}$)$R^{20}$, and optionally substituted $C_{1-4}$alkyl;

two of $R^{13}$, together with the atom or atoms to which they are attached, can combine to form a heteroalicyclic optionally substituted with between one and four of $R^{60}$, said heteroalicyclic can comprise up to four annular heteroatoms, and said heteroalicyclic can comprise an aryl or heteroaryl fused thereto, in which case said aryl or heteroaryl is optionally substituted with an additional one to four of $R^{60}$;

each $R^{14}$ is independently selected from —H, —$NO_2$, —N($R^{20}$)$R^{20}$, —CN, —$OR^{20}$, optionally substituted $C_{1-6}$alkyl, optionally substituted aryl, optionally substituted aryl $C_{1-6}$alkyl, optionally substituted heterocyclyl, optionally substituted heterocyclyl $C_{1-6}$alkyl;

Q is a five- to ten-membered annular system, optionally substituted with between zero and four of $R^{20}$;

each $R^{50}$ is independently either $R^{20}$, or according to formula II;

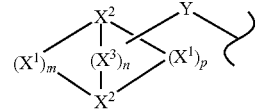

II wherein $X^1$, $X^2$, and optionally $X^3$, represent the atoms of a saturated bridged ring system, said saturated bridged ring system comprising up to four annular heteroatoms represented by any of $X^1$, $X^2$, and $X^3$; wherein, each $X^1$ is independently selected from —C($R^6$)$R^7$—, —O—, —$S(O)_{0-2}$—, and —$NR^8$—;

each $X^2$ is independently an optionally substituted bridgehead methine or a bridgehead nitrogen;

each $X^3$ is independently selected from —C($R^6$)$R^7$—, —O—, —$S(O)_{0-2}$—, and —$NR^8$—;

Y is either:
an optionally substituted lower alkylene linker, between D and either 1) any annular atom of the saturated bridged ring system, except $X^2$ when $X^2$ is a bridgehead nitrogen, or 2) any heteroatom, represented by any of $R^6$ or $R^7$; provided there are at least two carbon atoms between D and any annular heteroatom of the saturated bridged ring system or any heteroatom represented by any of $R^6$ or $R^7$;

or Y is absent, when Y is absent, said saturated bridged ring system, is directly attached to D via an annular carbon of said saturated bridged ring system, unless D is —$SO_2$—, in which case said saturated bridged ring system, is directly attached to D via an any annular atom of said saturated bridged ring system;

m and p are each independently one to four;

n is zero to two, when n equals zero there is a single bond between the two bridgehead $X^2$ 's;

$R^6$ and $R^7$ are each independently selected from —H, halogen, trihalomethyl, —CN, —$NO_2$, —$OR^{20}$, —$N(R^{20})R^{20}$, —$S(O)_{0-2}R^{20}$, —$SO_2N(R^{20})R^{20}$, —$CO_2R^{20}$, —C(O)N($R^{20}$)$R^{20}$, —$N(R^{20})SO_2R^{20}$, —$N(R^{20})C(O)R^{20}$, —$NCO_2R^{20}$, —C(O)$R^{20}$, optionally substituted $C_{1-6}$alkyl, optionally substituted aryl, optionally substituted aryl $C_{1-6}$alkyl, optionally substituted heterocyclyl, optionally substituted heterocyclyl $C_{1-6}$alkyl, and a bond to either Y or D; or $R^6$ and $R^7$, when taken together are oxo; or $R^6$ and $R^7$, when taken together with a common carbon to which they are attached, form a optionally substituted three- to seven-membered spirocyclyl, said optionally substituted three-to seven-membered spirocyclyl optionally containing at least one additional annular heteroatom selected from N, O, S, and P;

each $R^8$ is independently selected from —$R^{20}$, Y, —$SO_2N(R^{20})R^{20}$, —$CO_2R^{20}$, —C(O)N($R^{20}$)$R^{20}$, —$SO_2R^{20}$, and —C(O)$R^{20}$;

each $R^{20}$ is independently selected from —H, optionally substituted $C_{1-6}$alkyl, optionally substituted aryl, optionally substituted aryl $C_{1-6}$alkyl, optionally substituted heterocyclyl, and optionally substituted heterocyclyl $C_{1-6}$alkyl; or two of $R^{20}$, when taken together with a common nitrogen to which they are attached, can form an optionally substituted five- to seven-membered heterocyclyl, said optionally substituted five- to seven-membered heterocyclyl optionally containing at least one additional annular heteroatom selected from N, O, S, and P;

each $R^{60}$ is independently selected from —H, halogen, trihalomethyl, —CN, —$NO_2$, —$OR^{20}$, —$N(R^{20})R^{20}$, —$S(O)_{0-2}R^{20}$, —$SO_2N(R^{20})R^{20}$, —$CO_2R^{20}$, —$C(O)N(R^{20})R^{20}$, —$N(R^{20})SO_2R^{20}$, —$N(R^{20})C(O)R^{20}$, —$N(R^{20})CO_2R^{20}$, —$C(O)R^{20}$, optionally substituted $C_{1-6}$alkyl, optionally substituted aryl, optionally substituted aryl $C_{1-6}$alkyl, optionally substituted heterocyclyl, optionally substituted heterocyclyl $C_{1-6}$alkyl;

two of $R^{60}$, when taken together with a common carbon to which they are attached, can form an optionally substituted three- to seven-membered alicyclic or heteroalicyclic; and two of $R^{60}$, when taken together can be oxo.

In one example, the compound is according to paragraph [0025], wherein Z is either —O— or —$NR^4$—.

In another example, the compound is according to paragraph [0026], of formula III:

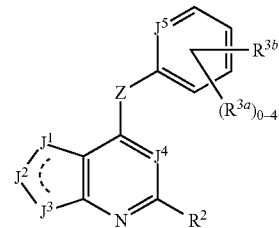

III wherein $J^4$ is =N— or =C(H)—; $J^5$ is selected from =N—, =$C(R^{3a})$—, and =$C(R^{3b})$—; each $R^{3a}$ is independently selected from —H, halogen, trihalomethyl, —CN, —$NO_2$, —$OR^{20}$, —$N(R^{20})R^{20}$, —$S(O)_{0-2}R^{20}$, —$SO_2N(R^{20})R^{20}$, —$CO_2R^{20}$, —$C(O)N(R^{20})R^{20}$, —$N(R^{20})SO_2R^{20}$, —$N(R^{20})C(O)R^{20}$, —$NCO_2R^{20}$, —$C(O)R^{20}$, optionally substituted $C_{1-6}$alkyl, and optionally substituted heterocyclyl; and $R^{3b}$ is selected from:

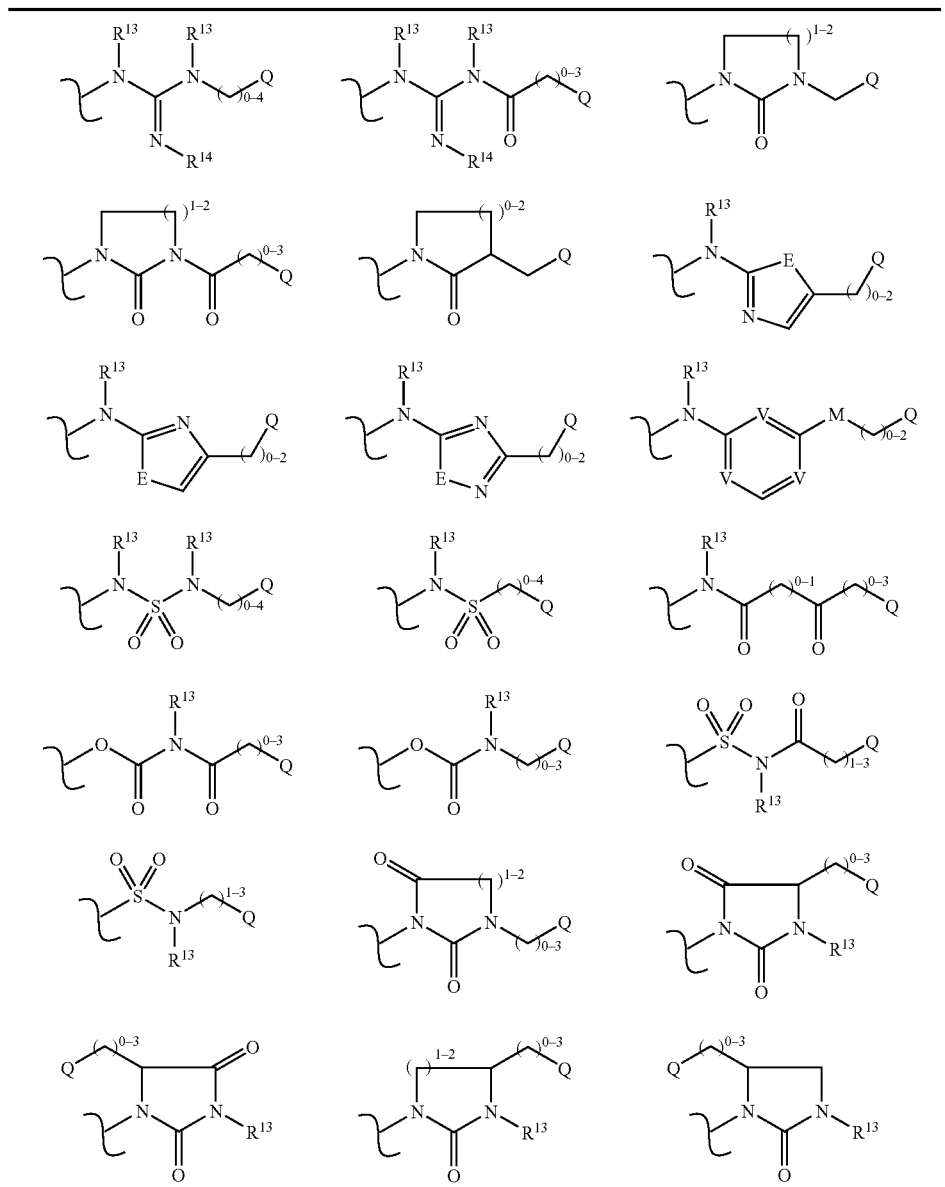

-continued

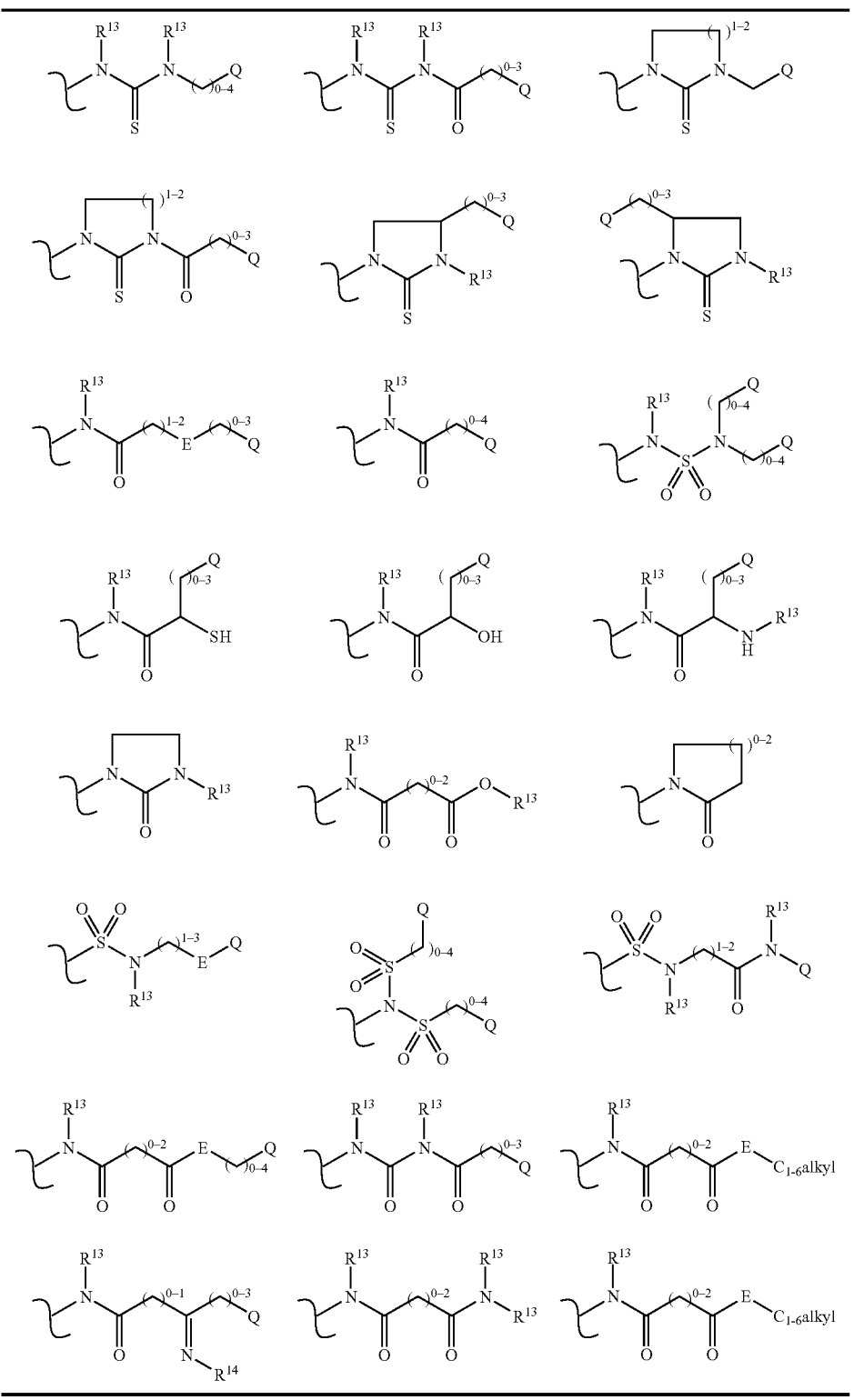

wherein Q, $R^{20}$, $R^{13}$ and $R^{14}$ are as defined above; each E is selected from —O—, —N($R^{13}$)—, —CH$_2$—, and —S(O)$_{0-2}$—; M is selected from —O—, —N($R^{13}$)—, —CH$_2$—, and —C(=O)N($R^{13}$)—; each V is independently either =N— or =C($R^{20}$)—; each methylene in any of the above formulae is independently optionally substituted with one or two of $R^{60}$.

In another example, the compound is according to paragraph [0027], wherein Z is —O—.

In another example, the compound is according to paragraph [0028], $R^{3b}$ is selected from:

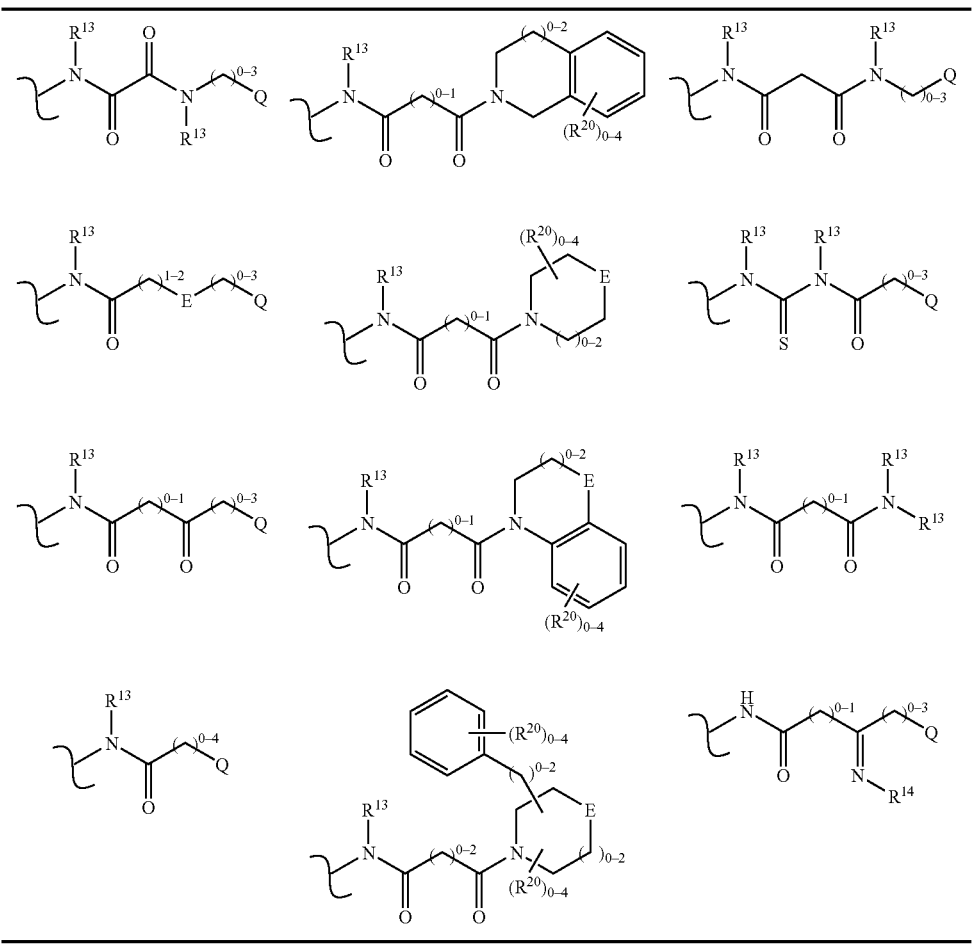

wherein Q, $R^{20}$, $R^{60}$, $R^{13}$ and $R^{14}$ are as defined above; each E is selected from —O—, —N($R^{13}$)—, —CH$_2$—, and —S(O)$_{0-2}$—; and each methylene in any of the above formulae is independently optionally substituted with one or two of $R^{60}$.

In another example, the compound is according to paragraph [0029], of formula IVa or IVb;

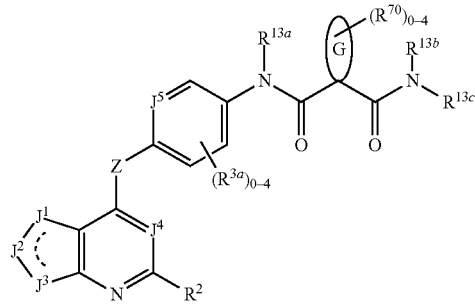

IVa

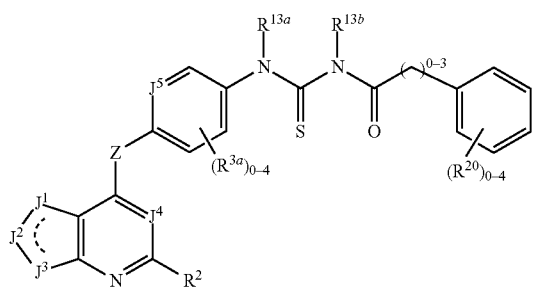

IVb wherein G is either an optionally substituted alicyclic or an optionally substituted heteroalicyclic; each $R^{70}$ is independently selected from —H, halogen, trihalomethyl, —CN, —NO$_2$, —OR$^{20}$, —N(R$^{20}$)R$^{20}$, —S(O)$_{0-2}$R$^{20}$, —SO$_2$N(R$^{20}$)R$^{20}$, —CO$_2$R$^{20}$, —C(O)N(R$^{20}$)R$^{20}$, —N(R$^{20}$)SO$_2$R$^{20}$, —N(R$^{20}$)C(O)R$^{20}$, —NCO$_2$R$^{20}$, —C(O)R$^{20}$, optionally substituted C$_{1-6}$alkyl, optionally substituted aryl, optionally substituted aryl C$_{1-6}$alkyl, optionally substituted heterocyclyl, and optionally substituted heterocyclyl C$_{1-6}$alkyl.

In another example, the compound is according to paragraph [0030], wherein —R$^{13a}$ is —H.

In another example, the compound is according to paragraph [0031], wherein —N(R$^{13b}$)R$^{13c}$ is selected from:

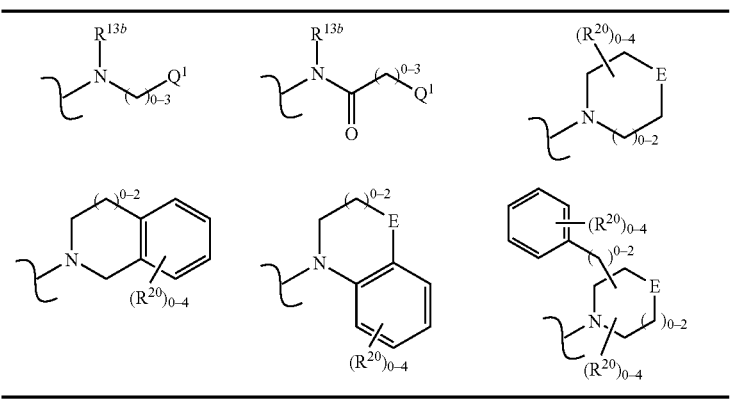

wherein $Q^1$, is a five- to ten-membered aryl or heteroaryl, optionally substituted with between zero and five of $R^{20}$; E is selected from —O—, —N($R^4$)—, —CH$_2$—, and —S(O)$_{0-2}$—; and each methylene in any of the above formulae, is independently optionally substituted with one or two of $R^{60}$.

In another example, the compound is according to paragraph [0032], of formula IVc or IVd:

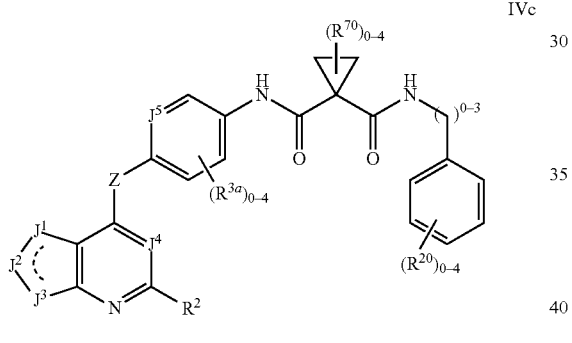

In another example, the compound is according to paragraph [0033], wherein $R^2$ is —H.

In another example, the compound is according to paragraph [0034], wherein at least one of $R^{3a}$ is halogen.

In another example, the compound is according to paragraph [0035], wherein at least one of $R^{3a}$ is fluorine.

In another example, the compound is according to paragraph [0036], of formula IVe or IVf:

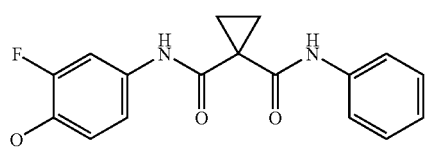

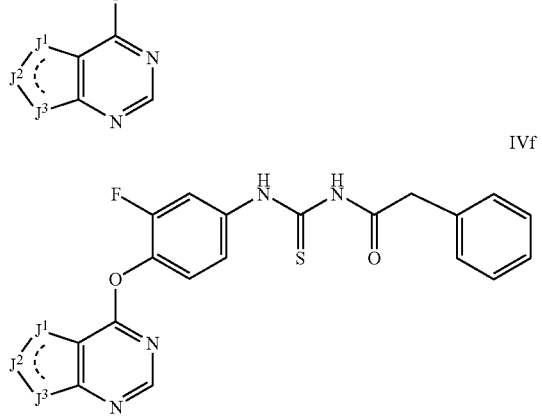

In another example, the compound is according to paragraph [0037], wherein $J^1$ is =C($R^{1a}$)—, $J^2$ is =C($R^{1b}$)—, and $J^3$ is —N($R^{1c}$)—.

In another example, the compound is according to paragraph [0037], wherein $J^1$ is =N—, $J^2$ is =C($R^{1b}$)—, and $J^3$ is —N($R^{1c}$)—.

In another example, the compound is according to paragraph [0037], wherein $J^1$ is =C($R^{1a}$)—, $J^2$ is =N—, and $J^3$ is —N($R^{1c}$)—.

In another example, the compound is according to any of paragraphs [0038]-[0040], wherein one of $R^{1a}$, $R^{1b}$ and $R^{1c}$ is selected from —C(O)N($R^{20}$)$R^{20}$, —C(O)$R^{20}$, optionally substituted C$_{1-6}$alkyl, optionally substituted C$_{1-6}$alkoxyl, optionally substituted heterocyclyl C$_{1-6}$alkyl and -D-R$^{50}$; provided D is —SO$_2$— when bonded to N.

In another example, the compound is according to paragraph [0038], wherein $R^{1b}$ is —C(O)N($R^{20a}$)$R^{20a}$, wherein at least one of $R^{20a}$ is C$_{1-4}$alkyl optionally substituted with an additional —N($R^{20}$)$R^{20}$.

In another example, the compound is according to paragraph [0042], wherein $R^{1b}$ is —C(O)N(H)$R^{20a}$, wherein $R^{20a}$ is optionally substituted heteroalicyclyl C$_{1-4}$alkyl.

In another example, the compound is according to paragraph [0043], wherein the heteroalicyclic portion of said optionally substituted heteroalicyclyl $C_{1-4}$alkyl is selected from the group consisting of piperidine, piperazine, morpholine, thiomorpholine, thiomorpholine 1-oxide, thiomorpholine 1,1-dioxide, 2-oxo-morpholine, pyrrolidine, and azepine.

In another example, the compound is according to paragraph [0041], wherein one of $R^{1a}$, $R^{1b}$ and $R^{1c}$ is -D-$R^{50}$.

In another example, the compound is according to paragraph [0045], wherein $R^{50}$ is optionally substituted heteroalicyclyl $C_{1-6}$alkyl.

In another example, the compound is according to paragraph [0046], wherein the heteroalicyclic portion of said optionally substituted heteroalicyclyl $C_{1-6}$alkyl is selected from the group consisting of piperidine, piperazine, morpholine, thiomorpholine, thiomorpholine 1-oxide, thiomorpholine 1,1-dioxide, 2-oxo-morpholine, pyrrolidine, and azepine.

In another example, the compound is according to paragraph [0045], wherein $R^{50}$ is according to formula II.

In another example, the compound is according to paragraph [0048], wherein the saturated bridged ring system according to formula II has a geometry selected from the group consisting of [4.4.0], [4.3.0], [4.2.0], [4.1.0], [3.3.0], [3.2.0], [3.1.0], [3.3.3], [3.3.2], [3.3.1], [3.2.2], [3.2.1], [2.2.2], and [2.2.1].

In another example, the compound is according to paragraph [0049], wherein Y is selected from —CH$_2$CH$_2$CH$_2$CH$_2$—, —CH$_2$CH$_2$CH$_2$—, —CH$_2$CH$_2$—, —CH$_2$—, and absent.

In another example, the compound is according to paragraph [0050], wherein n=0 and the saturated bridged ring system according to formula II has a geometry selected from the group consisting of [4.4.0], [4.3.0], [4.2.0], [4.1.0], [3.3.0], [3.2.0], and [3.1.0].

In another example, the compound is according to paragraph [0051], wherein said saturated bridged ring system contains at least one annular nitrogen or at least one annular oxygen.

In another example, the compound is according to paragraph [0052], wherein said saturated bridged ring system contains —NR$^8$—, wherein R$^8$ is selected from —H, optionally substituted $C_{1-6}$alkyl, —CO$_2$R$^{20}$, —C(O)N(R$^{20}$)R$^{20}$, —SO$_2$R$^{20}$, and —C(O)R$^{20}$.

In another example, the compound is according to paragraph [0052], wherein said saturated bridged ring system is of formula V,

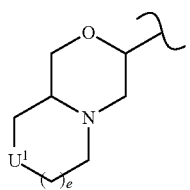

V wherein U$^1$ is selected from —O—, —S(O)$_{0-2}$—, —NR$^8$—, —CR$^6$R$^7$—, and absent; and e is 0 or 1.

In another example, the compound is according to paragraph [0054], wherein Y is —CH$_2$—.

In another example, the compound is according to paragraph [0055], wherein U$^1$ is —NR$^8$—, wherein R$^8$ is selected from —H, optionally substituted lower alkyl, —CO$_2$R$^{20}$, —C(O)N(R$^{20}$)R$^{20}$, —SO$_2$R$^{20}$, and —C(O)R$^{20}$.

In another example, the compound is according to paragraph [0055], wherein U$^1$ is —O—.

In another example, the compound is according to paragraph [0055], wherein U$^1$ is absent.

In another example, the compound is according to paragraph [0052], wherein Y is selected from —CH$_2$CH$_2$—, —CH$_2$—, and absent.

In another example, the compound is according to paragraph [0059], wherein said saturated bridged ring system is of formula VI,

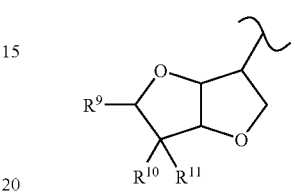

VI wherein R$^9$, R$^{10}$, and R$^{11}$ are each independently selected from —H, and —OR$^{12}$; or R$^9$ is selected from —H, and —OR$^{12}$, and R$^{10}$ and R$^{11}$, when taken together, are either an optionally substituted alkylidene or an oxo;

R$^{12}$ is selected from —H, —C(O)R$^{20}$, optionally substituted $C_{2-6}$alkylidyne, optionally substituted aryl $C_{2-6}$alkylidyne, optionally substituted heterocyclyl $C_{2-6}$alkylidyne, optionally substituted $C_{2-6}$alkylidene, optionally substituted aryl $C_{2-6}$alkylidene, optionally substituted heterocyclyl $C_{2-6}$alkylidene, optionally substituted $C_{1-6}$alkyl, optionally substituted aryl $C_{1-6}$alkyl, optionally substituted aryl, optionally substituted heterocyclyl $C_{1-6}$alkyl, and optionally substituted heterocyclyl;

or two R$^{12}$'s, when taken together, form 1) a corresponding spirocyclic ketal when said two R$^{12}$'s stem from R$^{10}$ and R$^{11}$, or 2) a corresponding cyclic ketal when said two R$^{12}$'s stem from R$^9$ and one of R$^{10}$ and R$^{11}$.

In another example, the compound is according to paragraph [0060], wherein one of R$^{10}$ and R$^{11}$ is —OR$^{12}$, wherein R$^{12}$ is selected from —H, —C(O)R$^{20}$, and optionally substituted $C_{1-6}$alkyl; and R$^9$ and the other of R$^{10}$ and R$^{11}$ are both —H.

In another example, the compound is according to paragraph [0061], wherein Y is either —CH$_2$— or absent.

In another example, the compound is according to paragraph [0060], wherein R$^9$ is an alkyl group containing at least one fluorine substitution thereon.

In another example, the compound is according to paragraph [0053], wherein said saturated bridged ring-system is of formula VII.

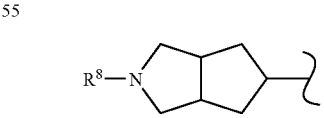

VII

In another example, the compound is according to paragraph [0064], wherein Y is either —CH$_2$— or absent.

In another example, the compound is according to paragraph [0065], wherein R$^8$ is methyl or ethyl.

In another example, the compound is according to paragraph [0053], wherein said saturated bridged ring system is of formula VIII.

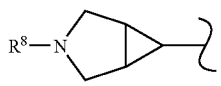
VIII

In another example, the compound is according to paragraph [0067], wherein Y is —CH$_2$—.

In another example, the compound is according to paragraph [0068], wherein R$^8$ is methyl or ethyl.

In another example, the compound is according to paragraph [0052], wherein said saturated bridged ring system is of formula IX

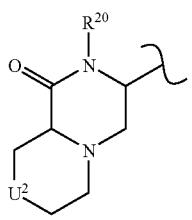
IX wherein U$^2$ is selected from —O—, —S(O)$_{0-2}$—, —NR$^8$—, —CR$^6$R$^7$—, and absent.

In another example, the compound is according to paragraph [0070], wherein R$^{20}$ of formula IX is selected from —H and optionally substituted alkyl.

In another example, the compound is according to paragraph [0071], wherein U$^2$ is either —CR$^6$R$^7$— or absent.

In another example, the compound is according to paragraph [0072], wherein U$^2$ is either —CH$_2$— or absent.

In another example, the compound is according to paragraph [0073], wherein Y is —CH$_2$—

In another example, the compound is according to paragraph [0053], wherein said saturated bridged ring system is according to formula X.

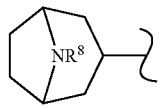
X

In another example, the compound is according to paragraph [0075], wherein R$^8$ is methyl or ethyl.

In another example, the compound is according to paragraph [0025], selected from Table 1.

TABLE 1

| Entry | Name | Structure |
|---|---|---|
| 1 | N-(4-fluorophenyl)-N'-[3-fluoro-4-(7H-pyrrolo[2,3-d]pyrimidin-4-yloxy)phenyl]propanediamide | 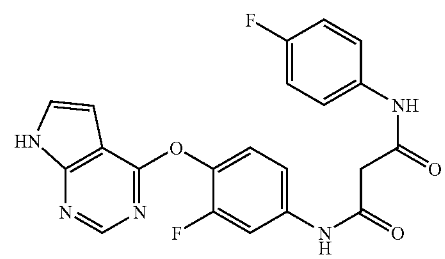 |
| 2 | N-(4-fluorophenyl)-N'-[3-fluoro-4-(7H-pyrrolo[2,3-d]pyrimidin-4-yloxy)phenyl]cyclopropane-1,1-dicarboxamide | 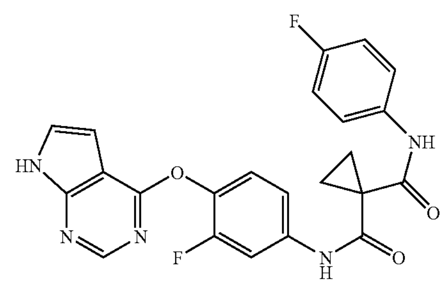 |
| 3 | N-({[3-fluoro-4-(7H-pyrrolo[2,3-d]pyrimidin-4-yloxy)phenyl]amino}carbonothioyl)-2-phenylacetamide | 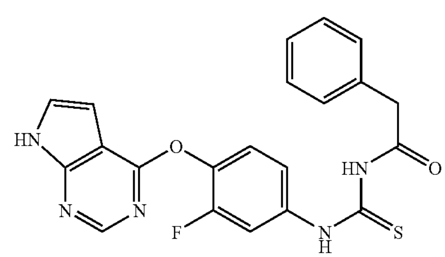 |

TABLE 1-continued

| Entry | Name | Structure |
|---|---|---|
| 4 | N-(4-fluorophenyl)-N'-(4-{[1-(tetrahydro-2H-pyran-2-yl)-1H-pyrazolo[3,4-d]pyrimidin-4-yl]oxy}phenyl)cyclopropane-1,1-dicarboxamide | 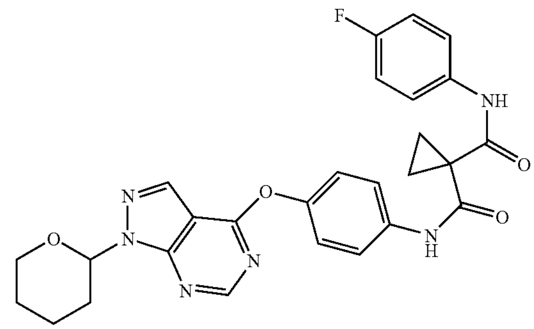 |
| 5 | 2-phenyl-N-{[(4-{[1-(tetrahydro-2H-pyran-2-yl)-1H-pyrazolo[3,4-d]pyrimidin-4-yl]oxy}phenyl)amino]carbonothioyl}acetamide | 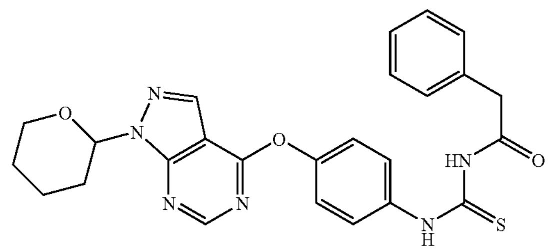 |
| 6 | N-(4-fluorophenyl)-N'-[4-(1H-pyrazolo[3,4-d]pyrimidin-4-yloxy)phenyl]cyclopropane-1,1-dicarboxamide | 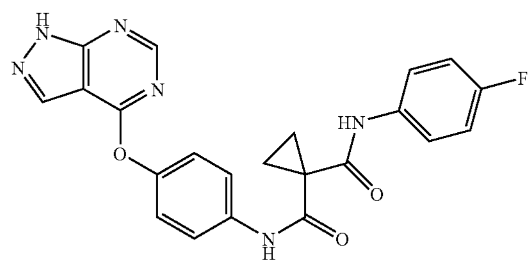 |
| 7 | 2-phenyl-N-({[4-(1H-pyrazolo[3,4-d]pyrimidin-4-yloxy)phenyl]amino}carbonothioyl)acetamide | 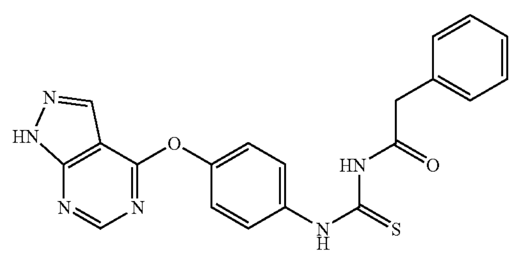 |
| 8 | N-(4-fluorophenyl)-N'-(4-{[9-(tetrahydro-2H-pyran-2-yl)-9H-purin-6-yl]oxy}phenyl)cyclopropane-1,1-dicarboxamide | 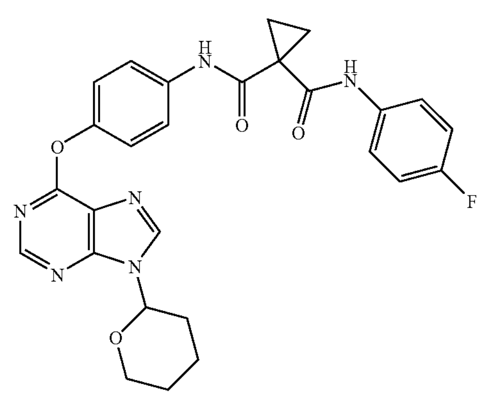 |

TABLE 1-continued

| Entry | Name | Structure |
|---|---|---|
| 9 | 2-phenyl-N-{[(4-{[9-(tetrahydro-2H-pyran-2-yl)-9H-purin-6-yl]oxy}phenyl)amino]carbonothioyl}acetamide | 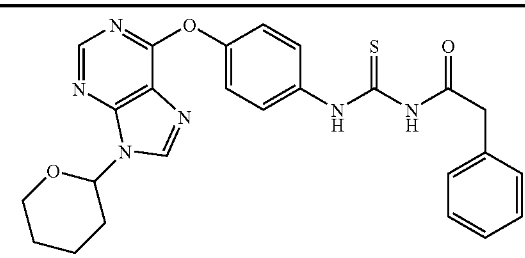 |
| 10 | N-(4-fluorophenyl)-N'-[4-(9H-purin-6-yloxy)phenyl]cyclopropane-1,1-dicarboxamide | 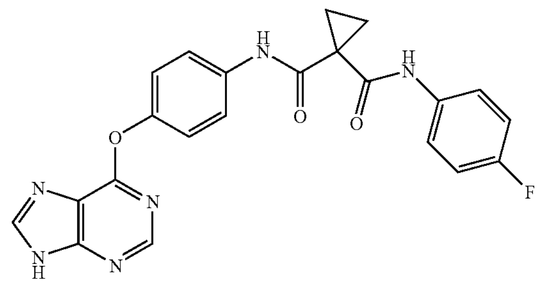 |
| 11 | 2-phenyl-N-({[4-(9H-purin-6-yloxy)phenyl]amino}carbonothioyl)acetamide | 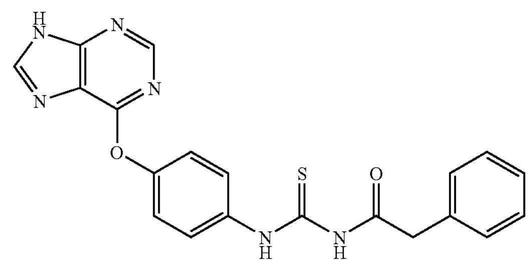 |
| 12 | N-{3-fluoro-4-[(6-{[(2-morpholin-4-ylethyl)amino]carbonyl}-7H-pyrrolo[2,3-d]pyrimidin-4-yl)oxy]phenyl}-N'-(4-fluorophenyl)cyclopropane-1,1-dicarboxamide | 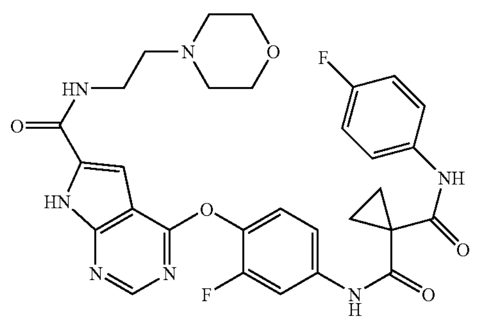 |

Another aspect of the invention is a pharmaceutical composition comprising a compound according to any one of paragraphs [0025]-[0077] and a pharmaceutically acceptable carrier.

Another aspect of the invention is a metabolite of the compound or the pharmaceutical composition according to any one of paragraphs [0025]-[0078].

Another aspect of the invention is a method of modulating the in vivo activity of a kinase, the method comprising administering to a subject an effective amount of the compound or the pharmaceutical composition according to any of paragraphs [0025]-[0078].

Another aspect of the invention is the method according to paragraph [0080], wherein the kinase is at least one of c-Met, KDR, and flt-3.

Another aspect of the invention is the method according to paragraph [0080], wherein the kinase is c-Met.

Another aspect of the invention is the method according to paragraph [0082], wherein modulating the in vivo activity of c-Met comprises inhibition of c-Met.

Another aspect of the invention is a method of treating diseases or disorders associated with uncontrolled, abnormal, and/or unwanted cellular activities, the method comprising administering, to a mammal in need thereof, a therapeutically effective amount of the compound or the pharmaceutical composition as described in any one of paragraphs [0025]-[0078].

Another aspect of the invention is a method of screening for a modulator of a kinase, said kinase selected from c-Met, KDR, and flt-3, the method comprising combining a compound according to any one of paragraphs [0025]-[0077], and at least one candidate agent and determining the effect of the candidate agent on the activity of said kinase.

Another aspect of the invention is a method of inhibiting proliferative activity in a cell or a plurality of cells, the method comprising administering an effective amount of a composition comprising a compound according any one of paragraphs [0025]-[0077] to said cell or said plurality of cells.

Definitions

As used in the present specification, the following words and phrases are generally intended to have the meanings as set forth below, except to the extent that the context in which they are used indicates otherwise or they are expressly defined to mean something different.

The symbol "—" means a single bond, "═" means a double bond, "≡" means a triple bond. The symbol "⁓" refers to a group on a double-bond as occupying either position on the terminus of a double bond to which the symbol is attached; that is, the geometry, E- or Z-, of the double bond is ambiguous. When a group is depicted removed from its parent formula, the "⁓" symbol will be used at the end of the bond which was theoretically cleaved in order to separate the group from its parent structural formula.

When chemical structures are depicted or described, unless explicitly stated otherwise, all carbons are assumed to have hydrogen substitution to conform to a valence of four. For example, in the structure on the left-hand side of the schematic below there are nine hydrogens implied. The nine hydrogens are depicted in the right-hand structure. Sometimes a particular atom in a structure is described in textual formula as having a hydrogen or hydrogens as substitution (expressly defined hydrogen), for example, —CH₂CH₂—. It is understood by one of ordinary skill in the art that the aforementioned descriptive techniques are common in the chemical arts to provide brevity and simplicity to description of otherwise complex structures.

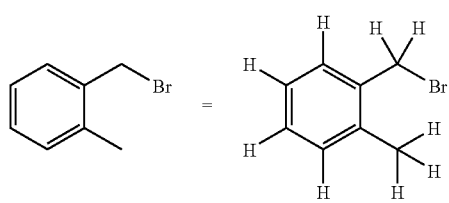

In this application, some ring structures are depicted generically and will be described textually. For example, in the schematic below, if in the structure on the left, ring A is used to describe a "spirocyclyl," then if ring A is cyclopropyl, there are at most four hydrogens on ring A (when "R" can also be —H). In another example, as depicted on the right side of the schematic below, if ring B is used to describe a "phenylene" then there can be at most four hydrogens on ring B (assuming depicted cleaved bonds are not C—H bonds).

If a group "R" is depicted as "floating" on a ring system, as for example in the formula:

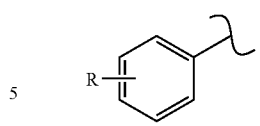

then, unless otherwise defined, a substituent "R" may reside on any atom of the ring system, assuming replacement of a depicted, implied, or expressly defined hydrogen from one of the ring atoms, so long as a stable structure is formed.

If a group "R" is depicted as floating on a fused ring system, as for example in the formulae:

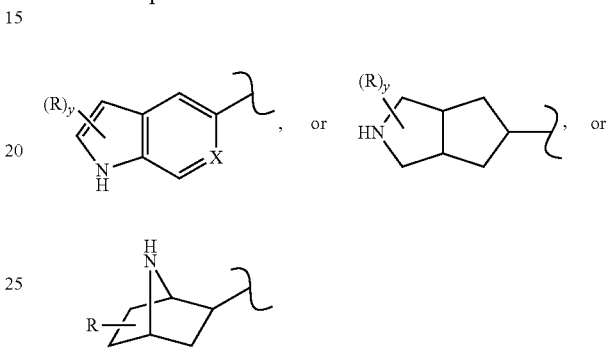

then, unless otherwise defined, a substituent "R" may reside on any atom of the fused ring system, assuming replacement of a depicted (for example the —NH— in the formula above), implied (for example as in the formula above, where the hydrogens are not shown but understood to be present), or expressly defined hydrogen (for example where in the formula above, "X" equals ═CH—) from one of the ring atoms, so long as a stable structure is formed. In the example depicted, the "R" group may reside on either the 5-membered or the 6-membered ring of the fused ring system. In the formula depicted above, when y is 2 for example, then the two "R's" may reside on any two atoms of the ring system, again assuming each replaces a depicted, implied, or expressly defined hydrogen on the ring.

When there are more than one such depicted "floating" groups, as for example in the formulae:

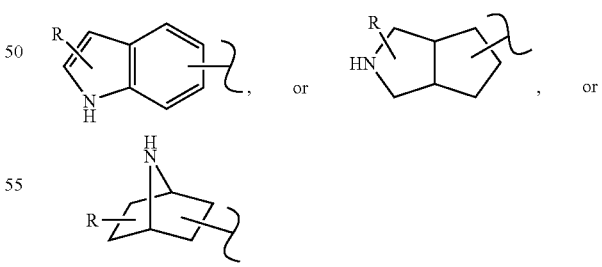

where there are two groups, namely, the "R" and the bond indicating attachment to a parent structure; then, unless otherwise defined, the "floating" groups may reside on any atoms of the ring system, again assuming each replaces a depicted, implied, or expressly defined hydrogen on the ring.

When a group "R" is depicted as existing on a ring system containing saturated carbons, as for example in the formula:

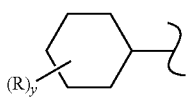

where, in this example, "y" can be more than one, assuming each replaces a currently depicted, implied, or expressly defined hydrogen on the ring; then, unless otherwise defined, where the resulting structure is stable, two "R's" may reside on the same carbon. A simple example is when R is a methyl group; there can exist a geminal dimethyl on a carbon of the depicted ring (an "annular" carbon).

In another example, two R's on the same carbon, including that carbon, may form a ring, thus creating a spirocyclic ring (a "spirocyclyl" group) structure with the depicted ring as for example in the formula:

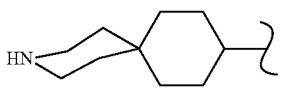

"Alicyclic" refers to a saturated carbocyclic ring system, for example cyclopropane and the like.

"Alkyl" is intended to include linear, branched, or cyclic hydrocarbon structures and combinations thereof, inclusively. For example, "$C_8$ alkyl" may refer to an n-octyl, iso-octyl, cyclohexylethyl, and the like. Lower alkyl refers to alkyl groups of from one to six carbon atoms. Examples of lower alkyl groups include methyl, ethyl, propyl, isopropyl, butyl, s-butyl, t-butyl, isobutyl, pentyl, hexyl and the like. Higher alkyl refers to alkyl groups containing more that eight carbon atoms. Exemplary alkyl groups are those of $C_{20}$ or below. Cycloalkyl is a subset of alkyl and includes cyclic hydrocarbon groups of from three to thirteen carbon atoms. Examples of cycloalkyl groups include c-propyl, c-butyl, c-pentyl, norbornyl, adamantyl and the like. In this application, alkyl refers to alkanyl, alkenyl, and alkynyl residues (and combinations thereof); it is intended to include cyclohexylmethyl, vinyl, allyl, isoprenyl, and the like. Thus when an alkyl residue having a specific number of carbons is named, all geometric isomers having that number of carbons are intended to be encompassed; thus, for example, either "butyl" or "$C_4$ alkyl" is meant to include n-butyl, sec-butyl, isobutyl, t-butyl, isobutenyl and but-2-yne radicals; and for example, "propyl" or "$C_3$ alkyl" each include n-propyl, propenyl, and isopropyl.

"Alkylene" refers to straight or branched chain divalent radical consisting solely of carbon and hydrogen atoms, containing no unsaturation and having from one to ten carbon atoms, for example, methylene, ethylene, propylene, n-butylene and the like. Alkylene is a subset of alkyl, referring to the same residues as alkyl, but having two points of attachment and, specifically, fully saturated. Examples of alkylene include ethylene (—$CH_2CH_2$—), propylene (—$CH_2CH_2CH_2$—), dimethylpropylene (—$CH_2C(CH_3)_2CH_2$—), and cyclohexylpropylene (—$CH_2CH_2CH(C_6H_{13})$).

"Alkylidene" refers to a straight or branched chain unsaturated divalent radical consisting solely of carbon and hydrogen atoms, having from two to ten carbon atoms, for example, ethylidene, propylidene, n-butylidene, and the like. Alkylidene is a subset of alkyl, referring to the same residues as alkyl, but having two points of attachment and, specifically, double bond unsaturation. The unsaturation present includes at least one double bond.

"Alkylidyne" refers to a straight or branched chain unsaturated divalent radical consisting solely of carbon and hydrogen atoms having from two to ten carbon atoms, for example, propylid-2-ynyl, n-butylid-1-ynyl, and the like. Alkylidyne is a subset of alkyl, referring to the same residues as alkyl, but having two points of attachment and, specifically, triple bond unsaturation. The unsaturation present includes at least one triple bond.

Any of the above radicals, "alkylene," "alkylidene" and "alkylidyne," when optionally substituted, may contain alkyl substitution which itself contains unsaturation. For example, 2-(2-phenylethynyl-but-3-enyl)-naphthalene (IUPAC name) contains an n-butylid-3-ynyl radical with a vinyl substituent at the 2-position of said radical.

"Alkoxy" or "alkoxyl" refers to the group —O-alkyl, for example including from one to eight carbon atoms of a straight, branched, cyclic configuration, unsaturated chains, and combinations thereof attached to the parent structure through an oxygen atom. Examples include methoxy, ethoxy, propoxy, isopropoxy, cyclopropyloxy, cyclohexyloxy and the like. Lower-alkoxy refers to groups containing one to six carbons.

"Substituted alkoxy" refers to the group —O—(substituted alkyl), the substitution on the alkyl group generally containing more than only carbon (as defined by alkoxy). One exemplary substituted alkoxy group is "polyalkoxy" or —O-optionally substituted alkylene-optionally substituted alkoxy, and includes groups such as —$OCH_2CH_2OCH_3$, and glycol ethers such as polyethyleneglycol and —$O(CH_2CH_2O)_xCH_3$, where x is an integer of between about two and about twenty, in another example, between about two and about ten, and in a further example between about two and about five. Another exemplary substituted alkoxy group is hydroxyalkoxy or —$OCH_2(CH_2)_yOH$, where y is for example an integer of between about one and about ten, in another example y is an integer of between about one and about four.

"Acyl" refers to groups of from one to ten carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to six carbons.

"α-Amino Acids" refer to naturally occurring and commercially available amino acids and optical isomers thereof. Typical natural and commercially available α-amino acids are glycine, alanine, serine, homoserine, threonine, valine, norvaline, leucine, isoleucine, norleucine, aspartic acid, glutamic acid, lysine, ornithine, histidine, arginine, cysteine, homocysteine, methionine, phenylalanine, homophenylalanine, phenylglycine, ortho-tyrosine, meta-tyrosine, para-tyrosine, tryptophan, glutamine, asparagine, proline and hydroxyproline. A "side chain of an α-amino acid" refers to the radical found on the α-carbon of an α-amino acid as defined above, for example, hydrogen (for glycine), methyl (for alanine), benzyl (for phenylalanine), and the like.

"Amino" refers to the group —$NH_2$. "Substituted amino," refers to the group —N(H)R or —N(R)R where each R is independently selected from the group: optionally substituted alkyl, optionally substituted alkoxy, optionally substituted aryl, optionally substituted heterocyclyl, acyl, carboxy, alkoxycarbonyl, sulfanyl, sulfinyl and sulfonyl, for example, diethylamino, methylsulfonylamino, furanyl-oxy-sulfonamino.

"Annular" refers to a single ring system either aromatic or alicyclic.

"Aryl" refers to aromatic six- to fourteen-membered carbocyclic ring, for example, benzene, naphthalene, indane, tetralin, fluorene and the like, univalent radicals. As univalent radicals, the aforementioned ring examples are named, phenyl, naphthyl, indanyl, tetralinyl, and fluorenyl.

"Arylene" generically refers to any aryl that has at least two groups attached thereto. For a more specific example, "phenylene" refers to a divalent phenyl ring radical. A phenylene, thus may have more than two groups attached, but is defined by a minimum of two non-hydrogen groups attached thereto.

"Arylalkyl" refers to a residue in which an aryl moiety is attached to a parent structure via one of an alkylene, alkylidene, or alkylidyne radical. Examples include benzyl, phenethyl, phenylvinyl, phenylallyl and the like. Both the aryl, and the corresponding alkylene, alkylidene, or alkylidyne radical portion of an arylalkyl group may be optionally substituted. "Lower arylalkyl" refers to an arylalkyl where the "alkyl" portion of the group has one to six carbons; this can also be referred to as $C_{1-6}$ arylalkyl.

"Exo-alkenyl" refers to a double bond that emanates from an annular carbon, and is not within the ring system, for example the double bond depicted in the formula below.

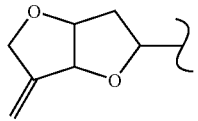

In some examples, as appreciated by one of ordinary skill in the art, two adjacent groups on an aromatic system may be fused together to form a ring structure. The fused ring structure may contain heteroatoms and may be optionally substituted with one or more groups. It should additionally be noted that saturated carbons of such fused groups (i.e. saturated ring structures) can contain two substitution groups.

"Fused-polycyclic" or "fused ring system" refers to a polycyclic ring system that contains bridged or fused rings; that is, where two rings have more than one shared atom in their ring structures. In this application, fused-polycyclics and fused ring systems are not necessarily all aromatic ring systems. Typically, but not necessarily, fused-polycyclics share a vicinal set of atoms, for example naphthalene or 1,2,3,4-tetrahydro-naphthalene. A spiro ring system is not a fused-polycyclic by this definition, but fused polycyclic ring systems of the invention may themselves have spiro rings attached thereto via a single ring atom of the fused-polycyclic.

"Halogen" or "halo" refers to fluorine, chlorine, bromine or iodine. "Haloalkyl" and "haloaryl" refer generically to alkyl and aryl radicals that are substituted with one or more halogens, respectively. Thus, "dihaloaryl," "dihaloalkyl," "trihaloaryl" etc. refer to aryl and alkyl substituted with a plurality of halogens, but not necessarily a plurality of the same halogen; thus 4-chloro-3-fluorophenyl is within the scope of dihaloaryl.

"Heteroarylene" generically refers to any heteroaryl that has at least two groups attached thereto. For a more specific example, "pyridylene" refers to a divalent pyridyl ring radical. A pyridylene, thus may have more than two groups attached, but is defined by a minimum of two non-hydrogen groups attached thereto.

"Heteroatom" refers to O, S, N, or P.

"Heterocyclyl" refers to a stable three- to fifteen-membered ring radical that consists of carbon atoms and from one to five heteroatoms selected from the group consisting of nitrogen, phosphorus, oxygen and sulfur. For purposes of this invention, the heterocyclyl radical may be a monocyclic, bicyclic or tricyclic ring system, which may include fused or bridged ring systems as well as spirocyclic systems; and the nitrogen, phosphorus, carbon or sulfur atoms in the heterocyclyl radical may be optionally oxidized to various oxidation states. In a specific example, the group —S(O)$_{0-2}$—, refers to —S— (sulfide), —S(O)— (sulfoxide), and —SO$_2$— (sulfone). For convenience, nitrogens, particularly but not exclusively, those defined as annular aromatic nitrogens, are meant to include their corresponding N-oxide form, although not explicitly defined as such in a particular example. Thus, for a compound of the invention having, for example, a pyridyl ring; the corresponding pyridyl-N-oxide is meant to be included as another compound of the invention. In addition, annular nitrogen atoms may be optionally quaternized; and the ring radical may be partially or fully saturated or aromatic. Examples of heterocyclyl radicals include, but are not limited to, azetidinyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, tetrahydrofuryl, tetrahydropyranyl, thienyl, benzothieliyl, thiamorpholinyl, thiamorpholinyl sulfoxide, thiamorpholinyl sulfone, dioxaphospholanyl, and oxadiazolyl.

"Heteroalicyclic" refers specifically to a non-aromatic heterocyclyl radical. A heteroalicyclic may contain unsaturation, but is not aromatic.

"Heteroaryl" refers specifically to an aromatic heterocyclyl radical.

"Heterocyclylalkyl" refers to a residue in which a heterocyclyl is attached to a parent structure via one of an alkylene, alkylidene, or alkylidyne radical. Examples include (4-methylpiperazin-1-yl)methyl, (morpholin-4-yl)methyl, (pyridine-4-yl)methyl, 2-(oxazolin-2-yl)ethyl, 4-(4-methylpiperazin-1-yl)-2-butenyl, and the like. Both the heterocyclyl, and the corresponding alkylene, alkylidene, or alkylidyne radical portion of a heterocyclylalkyl group may be optionally substituted. "Lower heterocyclylalkyl" refers to a heterocyclylalkyl where the "alkyl" portion of the group has one to six carbons. "Heteroalicyclylalkyl" refers specifically to a heterocyclylalkyl where the heterocyclyl portion of the group is non-aromatic; and "heteroarylalkyl" refers specifically to a heterocyclylalkyl where the heterocyclyl portion of the group is aromatic Such terms may be described in more than one way, for example, "lower heterocyclylalkyl" and "heterocyclyl $C_{1-6}$alkyl" are equivalent terms.

"Optional" or "optionally" means that the subsequently described event or circumstance may or may not occur, and that the description includes instances where said event or circumstance occurs and instances in which it does not. One of ordinary skill in the art would understand that, with respect to any molecule described as containing one or more optional substituents, that only sterically practical and/or synthetically feasible compounds are meant to be included. "Optionally substituted" refers to all subsequent modifiers in a term, for example in the term "optionally substituted aryl$C_{1-8}$ alkyl," optional substitution may occur on both the "$C_{1-8}$ alkyl" portion and the "aryl" portion of the molecule; and for example, optionally substituted alkyl includes optionally substituted cycloalkyl groups, which in turn are defined as including optionally substituted alkyl groups, potentially ad infinitum. A list of exemplary optional substitution are listed below in the definition of "substituted."

"Saturated bridged ring system" refers to a bicyclic or polycyclic ring system that is not aromatic. Such a system may contain isolated or conjugated unsaturation, but not aromatic or heteroaromatic rings in its core structure (but may have aromatic substitution thereon). For example, hexahydro-furo[3,2-b]furan, 2,3,3a,4,7,7a-hexahydro-1H-indene, 7-aza-bicyclo[2.2.1]heptane, and 1,2,3,4,4a,5,8,8a-octahydro-naphthalene are all included in the class "saturated bridged ring system."

"Spirocyclyl" or "spirocyclic ring" refers to a ring originating from a particular annular carbon of another ring. For example, as depicted below, a ring atom of a saturated bridged ring system (rings B and B'), but not a bridgehead atom, can be a shared atom between the saturated bridged ring system and a spirocyclyl (ring A) attached thereto. A spirocyclyl can be carbocyclic or heteroalicyclic.

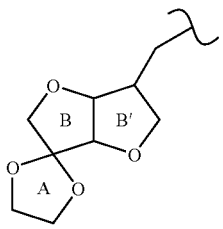

"Substituted" alkyl, aryl, and heterocyclyl, refer respectively to alkyl, aryl, and heterocyclyl, wherein one or more (for example up to about five, in another example, up to about three) hydrogen atoms are replaced by a substituent independently selected from: optionally substituted alkyl (for example, fluoromethyl), optionally substituted aryl (for example, 4-hydroxyphenyl), optionally substituted arylalkyl (for example, 1-phenyl-ethyl), optionally substituted heterocyclylalkyl (for example, 1-pyridin-3-yl-ethyl), optionally substituted heterocyclyl (for example, 5-chloro-pyridin-3-yl or 1-methyl-piperidin-4-yl), optionally substituted alkoxy, alkylenedioxy (for example methylenedioxy), optionally substituted amino (for example, alkylamino and dialkylamino), optionally substituted amidino, optionally substituted aryloxy (for example, phenoxy), optionally substituted arylalkyloxy (for example, benzyloxy), carboxy (—$CO_2H$), carboalkoxy (that is, acyloxy or —OC(=O)R), carboxyalkyl (that is, esters or —$CO_2R$), carboxamido, benzyloxycarbonylamino (CBZ-amino), cyano, acyl, halogen, hydroxy, nitro, sulfanyl, sulfinyl, sulfonyl, thiol, halogen, hydroxy, oxo, carbamyl, acylamino, and sulfonamido.

"Sulfanyl" refers to the groups: —S-(optionally substituted alkyl), —S-(optionally substituted aryl), and —S-(optionally substituted heterocyclyl).

"Sulfinyl" refers to the groups: —S(O)—H, —S(O)-(optionally substituted alkyl), —S(O)-optionally substituted aryl), and —S(O)-(optionally substituted heterocyclyl).

"Sulfonyl" refers to the groups: —S($O_2$)—H, —S($O_2$)-(optionally substituted alkyl), —S($O_2$)-optionally substituted aryl), —S($O_2$)-(optionally substituted heterocyclyl), —S($O_2$)-(optionally substituted alkoxy), —S($O_2$)-optionally substituted aryloxy), and —S($O_2$)-(optionally substituted heterocyclyloxy).

"Yield" for each of the reactions described herein is expressed as a percentage of the theoretical yield.

Some of the compounds of the invention may have imino, amino, oxo or hydroxy substituents off aromatic heterocyclyl systems. For purposes of this disclosure, it is understood that such imino, amino, oxo or hydroxy substituents may exist in their corresponding tautomeric form, i.e., amino, imino, hydroxy or oxo, respectively.

Compounds of the invention are named according to systematic application of the nomenclature rules agreed upon by the International Union of Pure and Applied Chemistry (IUPAC), International Union of Biochemistry and Molecular Biology (IUBMB), and the Chemical Abstracts Service (CAS).

The compounds of the invention, or their pharmaceutically acceptable salts, may have asymmetric carbon atoms, oxidized sulfur atoms or quaternized nitrogen atoms in their structure.

The compounds of the invention and their pharmaceutically acceptable salts may exist as single stereoisomers, racemates, and as mixtures of enantiomers and diastereomers. The compounds may also exist as geometric isomers. All such single stereoisomers, racemates and mixtures thereof, and geometric isomers are intended to be within the scope of this invention.

It is assumed that when considering generic descriptions of compounds of the invention for the purpose of constructing a compound, such construction results in the creation of a stable structure. That is, one of ordinary skill in the art would recognize that there can theoretically be some constructs which would not normally be considered as stable compounds (that is, sterically practical and/or synthetically feasible, supra).

When a particular group with its bonding structure is denoted as being bonded to two partners; that is, a divalent radical, for example, —$OCH_2$—, then it is understood that either of the two partners may be bound to the particular group at one end, and the other partner is necessarily bound to the other end of the particular group, unless stated explicitly otherwise. Stated another way, divalent radicals are not to be construed as limited to the depicted orientation, for example "—$OCH_2$—" is meant to mean not only "—$OCH_2$—" as drawn, but also "—$CH_2O$—."

Methods for the preparation and/or separation and isolation of single stereoisomers from racemic mixtures or non-racemic mixtures of stereoisomers are well known in the art. For example, optically active (R)- and (S)-isomers may be prepared using chiral synthons or chiral reagents, or resolved using conventional techniques. Enantiomers (R- and S-isomers) may be resolved by methods known to one of ordinary skill in the art, for example by: formation of diastereoisomeric salts or complexes which may be separated, for example, by crystallization; via formation of diastereoisomeric derivatives which may be separated, for example, by crystallization, selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents, or by converting on enantiomer to the other by asymmetric transformation. For a mixture of enantiomers, enriched in a particular enantiomer, the major component enantiomer may be further enriched (with concomitant loss in yield) by recrystallization.

"Patient" for the purposes of the present invention includes humans and other animals, particularly mammals, and other organisms. Thus the methods are applicable to both human therapy and veterinary applications. In a preferred embodiment the patient is a mammal, and in a most preferred embodiment the patient is human.

"Kinase-dependent diseases or conditions" refer to pathologic conditions that depend on the activity of one or more protein kinases. Kinases either directly or indirectly participate in the signal transduction pathways of a variety of cellular activities including proliferation, adhesion, migration, differentiation and invasion. Diseases associated with kinase activities include tumor growth, the pathologic neovascularization that supports solid tumor growth, and associated with other diseases where excessive local vascularization is involved such as ocular diseases (diabetic retinopathy, age-related macular degeneration, and the like) and inflammation (psoriasis, rheumatoid arthritis, and the like).

While not wishing to be bound to theory, phosphatases can also play a role in "kinase-dependent diseases or conditions" as cognates of kinases; that is, kinases phosphorylate and phosphatases dephosphorylate, for example protein substrates. Therefore compounds of the invention, while modulating kinase activity as described herein, may also modulate, either directly or indirectly, phosphatase activity. This additional modulation, if present, may be synergistic (or not) to activity of compounds of the invention toward a related or otherwise interdependent kinase or kinase family. In any case, as stated previously, the compounds of the invention are useful for treating diseases characterized in part by abnormal levels of cell proliferation (i.e. tumor growth), programmed cell death (apoptosis), cell migration and invasion and angiogenesis associated with tumor growth.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

"Cancer" refers to cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinorna, glucagonoma, gastrinoma, carcinoid tumors, vipoma), small bowel (adenocarcinorna, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [neplrroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformians), meninges (meningioma, meningiosarcoma, gliomatosis), brain (astrocytoma, medulloblastoma, glioma, ependymoma, germinoma [pinealoma], glioblastorna multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, SertoliLeydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal lands: neuroblastoma. Thus, the term "cancerous cell" as provided herein, includes a cell afflicted by any one of the above-identified conditions.

"Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19 which is incorporated herein by reference.)

"Prodrug" refers to compounds that are transformed (typically rapidly) in vivo to yield the parent compound of the above formulae, for example, by hydrolysis in blood. Common examples include, but are not limited to, ester and amide forms of a compound having an active form bearing a carboxylic acid moiety. Examples of pharmaceutically acceptable esters of the compounds of this invention include, but are not limited to, alkyl esters (for example with between about one and about six carbons) wherein the alkyl group is a straight or branched chain. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons). Amides and esters of the compounds of the present invention may be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Metabolite" refers to the break-down or end product of a compound or its salt produced by metabolism or biotransformation in the animal or human body; for example, biotransformation to a more polar molecule such as by oxidation, reduction, or hydrolysis, or to a conjugate (see Goodman and Gilman, "The Pharmacological Basis of Therapeutics" 8.sup.th Ed., Pergamon Press, Gilman et al. (eds), 1990 for a discussion of biotransformation). As used herein, the metabolite of a compound of the invention or its salt may be the biologically active form of the compound in the body. In one example, a prodrug may be used such that the biologically active form, a metabolite, is released in vivo. In another example, a biologically active metabolite is discovered serendipitously, that is, no prodrug design per se was undertaken. An assay for activity of a metabolite of a compound of the present invention is known to one of skill in the art in light of the present disclosure.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

In addition, it is intended that the present invention cover compounds made either using standard organic synthetic techniques, including combinatorial chemistry or by biological methods, such as bacterial digestion, metabolism, enzymatic conversion, and the like.

"Treating" or "treatment" as used herein covers the treatment of a disease-state in a human, which disease-state is characterized by abnormal cellular proliferation, and invasion and includes at least one of: (i) preventing the disease-state from occurring in a human, in particular, when such human is predisposed to the disease-state but has not yet been diagnosed as having it; (ii) inhibiting the disease-state, i.e., arresting its development; and (iii) relieving the disease-state, i.e., causing regression of the disease-state. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

One of ordinary skill in the art would understand that certain crystallized, protein-ligand complexes, in particular c-Met, c-Kit, KDR, flt-3, or flt-4-ligand complexes, and their corresponding x-ray structure coordinates can be used to reveal new structural information useful for understanding the biological activity of kinases as described herein. As well, the key structural features of the aforementioned proteins, particularly, the shape of the ligand binding site, are useful in methods for designing or identifying selective modulators of kinases and in solving the structures of other proteins with similar features. Such protein-ligand complexes, having compounds of the invention as their ligand component, are an aspect of the invention.

As well, one of ordinary skill in the art would appreciate that such suitable x-ray quality crystals can be used as part of a method of identifying a candidate agent capable of binding to and modulating the activity of kinases. Such methods may be characterized by the following aspects: a) introducing into a suitable computer program, information defining a ligand binding domain of a kinase in a conformation (e.g. as defined by x-ray structure coordinates obtained from suitable x-ray quality crystals as described above) wherein the computer program creates a model of the three dimensional structures of the ligand binding domain, b) introducing a model of the three dimensional structure of a candidate agent in the computer program, c) superimposing the model of the candidate agent on the model of the ligand binding domain, and d) assessing whether the candidate agent model fits spatially into the ligand binding domain. Aspects a-d are not necessarily carried out in the aforementioned order. Such methods may further entail: performing rational drug design with the model of the three-dimensional structure, and selecting a potential candidate agent in conjunction with computer modeling.

Additionally, one skilled in the art would appreciate that such methods may further entail: employing a candidate agent, so-determined to fit spatially into the ligand binding domain, in a biological activity assay for kinase modulation, and determining whether said candidate agent modulates kinase activity in the assay. Such methods may also include administering the candidate agent, determined to modulate kinase activity, to a mammal suffering from a condition treatable by kinase modulation, such as those described above.

Also, one skilled in the art would appreciate that compounds of the invention can be used in a method of evaluating the ability of a test agent to associate with a molecule or molecular complex comprising a ligand binding domain of a kinase. Such a method may be characterized by the following aspects: a) creating a computer model of a kinase binding pocket using structure coordinates obtained from suitable x-ray quality crystals of the kinase, b) employing computational algorithms to perform a fitting operation between the test agent and the computer model of the binding pocket, and c) analyzing the results of the fitting operation to quantify the association between the test agent and the computer model of the binding pocket.

General Administration

Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracistemally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages.

The compositions will include a conventional pharmaceutical carrier or excipient and a compound of the invention as the/an active agent, and, in addition, may include other medicinal agents, pharmaceutical agents, carriers, adjuvants, etc. Compositions of the invention may be used in combination with anticancer or other agents that are generally administered to a patient being treated for cancer. Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylalted hydroxytoluene, etc.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One preferable route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms as described above can be prepared with coatings and shells, such as enteric coatings and others well known in the art. They may contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of the invention, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compounds of the present invention with for example suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. In one example, the composition will be between about 5% and about 75% by weight of a compound(s) of the invention, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state in accordance with the teachings of this invention.

The compounds of the invention, or their pharmaceutically acceptable salts, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

Utility of Compounds of the Invention as Screening Agents

To employ the compounds of the invention in a method of screening for candidate agents that bind to, for example c-Met, KDR, or flt-3, the protein is bound to a support, and a compound of the invention is added to the assay. Alternatively, the compound of the invention is bound to the support and the protein is added. Classes of candidate agents among which novel binding agents may be sought include specific antibodies, non-natural binding agents identified in screens of chemical libraries, peptide analogs, etc. Of particular interest are screening assays for candidate agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the candidate agent to, for example, c-Met, KDR, or flt-3 protein may be done in a number of ways. In one example, the candidate agent (the compound of the invention) is labeled, for example, with a fluorescent or radioactive moiety and binding determined directly. For example, thus may be done by attaching all or a portion of the c-Met, KDR, or flt-3 protein to a solid support, adding a labeled agent (for example a compound of the invention in which at least one atom has been replaced by a detectable isotope), washing off excess reagent, and determining whether the amount of the label is that present on the solid support. Various blocking and washing steps may be utilized as is known in the art.

By "labeled" herein is meant that the compound is either directly or indirectly labeled with a label which provides a detectable signal, e.g., radioisotope, fluorescent tag, enzyme, antibodies, particles such as magnetic particles, chemiluminescent tag, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In some embodiments, only one of the components is labeled. For example, c-Met, KDR, or flt-3 protein may be labeled at tyrosine positions using $^{125}$I, or with fluorophores. Alternatively, more than one component may be labeled with different labels; using $^{125}$I for the proteins, for example, and a fluorophor for the candidate agents.

The compounds of the invention may also be used as competitors to screen for additional drug candidates. "Candidate bioactive agent" or "drug candidate" or grammatical equivalents as used herein describe any molecule, e.g., protein, oligopeptide, small organic molecule, polysaccharide, polynucleotide, etc., to be tested for bioactivity. They may be capable of directly or indirectly altering the cellular proliferation phenotype or the expression of a cellular proliferation sequence, including both nucleic acid sequences and protein sequences. In other cases, alteration of cellular proliferation protein binding and/or activity is screened. In the case where protein binding or activity is screened, some embodiments exclude molecules already known to bind to that particular protein. Exemplary embodiments of assays described herein include candidate agents, which do not bind the target protein in its endogenous native state, termed herein as "exogenous" agents. In one example, exogenous agents further exclude antibodies to c-Met, KDR, or flt-3.

Candidate agents can encompass numerous chemical classes, though typically they are organic molecules having a molecular weight of more than about 100 daltons and less than about 2,500 daltons. Candidate agents comprise functional groups necessary for structural interaction with proteins, particularly hydrogen bonding and lipophilic binding, and typically include at least an amine, carbonyl, hydroxyl, ether, or carboxyl group, for example at least two of the functional chemical groups. The candidate agents often comprise cyclical carbon or heterocyclyl structures and/or aromatic or polyaromatic structures substituted with one or more of the above functional groups. Candidate agents are also found among biomolecules including peptides, saccharides, fatty acids, steroids, purines, pyrimidines, derivatives, structural analogs, or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In one example, the binding of the candidate agent is determined through the use of competitive binding assays. In this example, the competitor is a binding moiety known to bind to c-Met, KDR, or flt-3, such as an antibody, peptide, binding partner, ligand, etc. Under certain circumstances, there may be competitive binding as between the candidate agent and the binding moiety, with the binding moiety displacing the candidate agent.

In some embodiments, the candidate agent is labeled. Either the candidate agent, or the competitor, or both, is added first to for example c-Met, KDR, or flt-3 for a time sufficient to allow binding, if present. Incubations may be performed at any temperature that facilitates optimal activity, typically between 4° C. and 40° C.

Incubation periods are selected for optimum activity, but may also be optimized to facilitate rapid high throughput screening. Typically between 0.1 and 1 hour will be sufficient. Excess reagent is generally removed or washed away. The second component is then added, and the presence or absence of the labeled component is followed, to indicate binding.

In one example, the competitor is added first, followed by the candidate agent. Displacement of the competitor is an indication the candidate agent is binding to c-Met, KDR, or flt-3 and thus is capable of binding to, and potentially modulating, the activity of the c-Met, KDR, or flt-3. In this embodiment, either component can be labeled. Thus, for example, if the competitor is labeled, the presence of label in the wash solution indicates displacement by the agent. Alternatively, if the candidate agent is labeled, the presence of the label on the support indicates displacement.

In an alternative embodiment, the candidate agent is added first, with incubation and washing, followed by the competitor. The absence of binding by the competitor may indicate the candidate agent is bound to c-Met, KDR, or flt-3, with a higher affinity. Thus, if the candidate agent is labeled, the presence of the label on the support, coupled with a lack of competitor binding, may indicate the candidate agent is capable of binding to c-Met, KDR, or flt-3.

It may be of value to identify the binding site of c-Met, KDR, or flt-3. This can be done in a variety of ways. In one embodiment, once c-Met, KDR, or flt-3, has been identified as binding to the candidate agent, the c-Met, KDR, or flt-3, is fragmented or modified and the assays repeated to identify the necessary components for binding.

Modulation is tested by screening for candidate agents capable of modulating the activity of c-Met, KDR, or flt-3, comprising the steps of combining a candidate agent with c-Met, KDR, or flt-3, as above, and determining an alteration in the biological activity of the c-Met, KDR, or flt-3. Thus, in this embodiment, the candidate agent should both bind to (although this may not be necessary), and alter its biological or biochemical activity as defined herein. The methods include both in vitro screening methods and in vivo screening of cells for alterations in cell viability, morphology, and the like.

Alternatively, differential screening may be used to identify drug candidates that bind to native c-Met, KDR, or flt-3, but cannot bind to modified c-Met, KDR, or flt-3.

Positive controls and negative controls may be used in the assays. For example, all control and test samples are performed in at least triplicate to obtain statistically significant results. Incubation of samples is for a time sufficient for the binding of the agent to the protein. Following incubation, samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g., albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

Abbreviations and Their Definitions

The following abbreviations and terms have the indicated meanings throughout:

| Abbreviation | Meaning |
| --- | --- |
| Ac | acetyl |
| ACN | acetonitrile |
| ATP | adenosine triphosphate |
| BNB | 4-bromomethyl-3-nitrobenzoic acid |
| Boc | t-butyloxy carbonyl |
| br | broad |
| Bu | butyl |
| ° C. | degrees Celsius |
| c- | cyclo |
| CBZ | CarboBenZoxy = benzyloxycarbonyl |
| d | doublet |
| dd | doublet of doublet |
| dt | doublet of triplet |
| DBU | Diazabicyclo[5.4.0]undec-7-ene |
| DCM | dichloromethane = methylene chloride = $CH_2Cl_2$ |
| DCE | dichloroethylene |
| DEAD | diethyl azodicarboxylate |
| DIC | diisopropylcarbodiimide |
| DIEA | N,N-diisopropylethyl amine |
| DMAP | 4-N,N-dimethylaminopyridine |
| DMF | N,N-dimethylfonnamide |
| DMSO | dimethyl sulfoxide |
| DVB | 1,4-divinylbenzene |
| EEDQ | 2-ethoxy-1-ethoxycarbonyl-1,2-dihydroquinoline |
| EI | Electron Impact ionization |
| Et | ethyl |
| Fmoc | 9-fluorenylmethoxycarbonyl |
| g | gram(s) |
| GC | gas chromatography |
| h or hr | hour(s) |
| HATU | O-(7-Azabenzotriazol-1-yl)-1,1,3,3-tetramethyluronium hexafluorophosphate |
| HMDS | hexamethyldisilazane |
| HOAc | acetic acid |
| HOBt | hydroxybenzotriazole |
| HPLC | high pressure liquid chromatography |
| L | liter(s) |
| M | molar or molarity |
| m | multiplet |
| Me | methyl |
| mesyl | methanesulfonyl |
| mg | milligram(s) |
| MHz | megahertz (frequency) |
| Min | minute(s) |
| mL | milliliter(s) |
| mM | millimolar |
| mmol | millimole(s) |
| mol | mole(s) |
| MS | mass spectral analysis |
| MTBE | methyl t-butyl ether |
| N | normal or normality |
| NBS | N-bromosuccinimide |
| NCS | N-chlorosuccinimide |
| nM | nanomolar |
| NMO | N-methylmorpholine oxide |
| NMR | nuclear magnetic resonance spectroscopy |
| PEG | polyethylene glycol |
| pEY | poly-glutamine, tyrosine |
| Ph | phenyl |
| PhOH | phenol |
| PfP | pentafluorophenol |
| PfPy | pentafluoropyridine |
| PPTS | Pyridinium p-toluenesulfonate |
| Py | pyridine |
| PyBroP | bromo-tris-pyrrolidino-phosphonium hexafluorophosphate |
| q | quartet |
| RT | Room temperature |
| Sat'd | saturated |
| s | singlet |
| SEM-Cl | chloromethyl 2-trimethylsilylethyl ether |
| s- | secondary |
| t- | tertiary |
| t or tr | triplet |

| Abbreviation | Meaning |
|---|---|
| TBDMS | t-butyldimethylsilyl |
| TES | triethylsilane |
| TFA | trifluoroacetic acid |
| THF | tetrahydrofuran |
| TMOF | trimethyl orthoformate |
| TMS | trimethylsilyl |
| tosyl | p-toluenesulfonyl |
| Trt | triphenylmethyl |
| µL | microliter(s) |
| µM | Micromole(s) or micromolar |

Synthesis of Compounds

Scheme 1 depicts a general synthetic route for compounds of the invention and is not intended to be limiting. Specific examples are described subsequently to this general synthetic description so as to allow one of ordinary skill in the art to make and use compounds of the invention.

Referring to Scheme 1, ester 1, for example where R is typically but not necessarily an alkyl radical (and $R^1$ for example is as defined above), is exemplary of a starting material for constructing 5,6-fused systems used in making compounds of the invention. In this example, a pyrrole derivative, 1, is used as a starting point. According to the description above, one of ordinary skill in the art would understand that other appropriately-functionalized five-membered ring systems such as thiophenes, pyrazolines, imidazoles, triazoles, thiazoles, oxazoles, thiadiazoles, oxadiazoles and the like, including regioisomers, can be used in analogous fashion to make the corresponding 5,6-fused systems of the invention. Indeed, one of ordinary skill in the art would appreciate that such five-membered ring systems are commercially available in many instances, but if not, can be made using well-known chemistry. Additionally, although Scheme 1 outlines methods for making 5,6-fused systems starting with a five-membered ring precursor, such systems can also be made via routes such as starting with a six-membered ring system and appending a five-membered ring; constructing a 5,6-fused system simultaneously, or modifying pre-existing 5,6-fused ring systems (for example commercially available compounds). Substituents in formula of Scheme 1 are consistent with those described in relation to formula I wherever possible so as to relate how the synthesis scheme relates to formation of compounds of the invention.

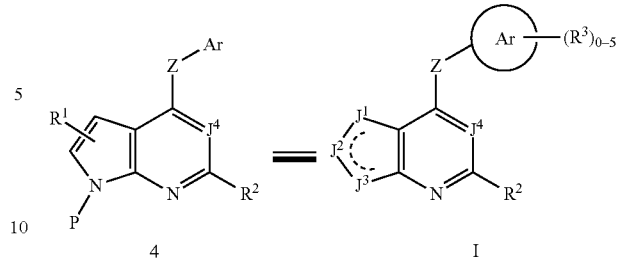

Formation of 5,6-fused system 2 is carried out by methods well known in the art, for example by heating 1 in the presence of a trialkylorthoformate and subsequent exposure to, for example, ammonia to make the corresponding pyrrolo[2,3-d] pyrimidine 2. In one example, the hydroxyl of pyrimidine 2 is converted to a leaving group, for example a halogen or triflate, to form intermediate 3. In some instances it is desirable to protect the pyrrole nitrogen with a protecting group "P" (for example a SEM group) before subsequent manipulation. Nucleophiles, for example aryls substituted with "Z" as defined above, are added to 3 to form 4. In alternative embodiments (not depicted), the hydroxyl of 2 is itself used as a nucleophile (where "Z" of formula I is —O—) to attach "Ar" according to formula I and form 4. In alternative embodiments, the hydroxyl is converted to a sulfur or nitrogen which is then used as a nucleophile. Compounds 4 are exemplary embodiments of the invention according to formula I.

One of ordinary skill in the art would appreciate that functionality, for example "$R^1$," about the 5,6-fused systems described can be manipulated at any stage of the aforementioned synthesis outlined to make compounds according to formula I. Again Scheme 1, in conjunction with the examples below, will make it sufficiently clear to one of ordinary skill in the art how to make compounds of the invention.

EXAMPLES

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety. Generally, each example set out below describes a multi-step synthesis, or at least a part of such, as outlined above.

Scheme 1

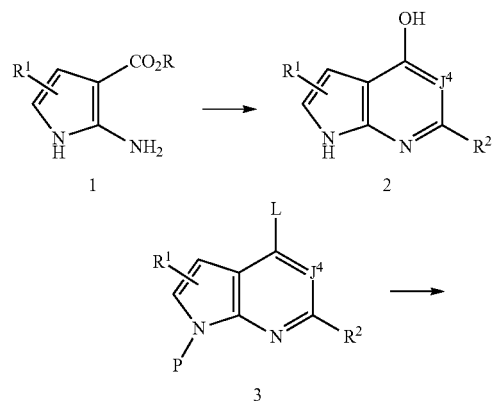

Example 1

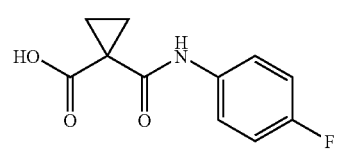

1-(4-Fluoro-phenylcarbamoyl)-cyclopropanecarboxylic acid. The title compound was prepared based on a modified procedure of Shih and Rankin [*Synthetic Communications*, 1996, 26(4), 833-836]: To a mixture of cyclopropane-1,1-dicarboxylic acid (21.2 g, 0.163 mol, 1.0 eq.) in anhydrous THF (200 mL) under nitrogen was added dropwise triethylamine (16.49 g, 0.163 mol, 1.0 eq.) with stirring for 30 minutes at 0° C., followed by the addition of thionyl chloride (19.39 g, 0.163 mol, 1.0 eq.) with stirring for another 30 minutes at 0° C. To the resulting mixture under nitrogen was added dropwise a solution of 4-fluoroaniline (19.92 g, 0.179 mol, 1.1 eq.) in anhydrous THF (100 mL) with stirring for 1:5 hours at 0° C. The reaction mixture was diluted with ethyl acetate and washed with 1N NaOH. The layers were separated, and the ethyl acetate layer was concentrated in vacuo to give a brownish solid. The brownish solid was washed with small amount of cold ethyl acetate, filtered and dried under vacuum to yield 1-(4-fluoro-phenylcarbamoyl)-cyclopropanecarboxylic acid as a white solid (23.71 g, 65.18%). $^1$H NMR (400 MHz, CD$_3$OD): 7.57-7.53 (m, 2H), 7.05-7.00 (m, 2H) 1.46-1.43 (m, 2H), 1.40-1.37 (m, 2H).

Example 2

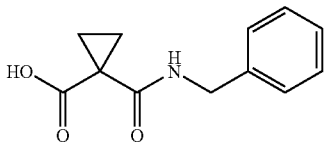

1-Benzylcarbamoyl-cyclopropanecarboxylic acid. The title compound was prepared based on a modified procedure of Shih and Rankin [*Synthetic Communications*, 1996, 26(4), 833-836]: To a mixture of cyclopropane-1,1-dicarboxylic acid (5.0 g, 38.4 mmol, 1.0 eq.) in anhydrous THF (50 mL) under nitrogen was added dropwise triethylamine (3.89 g, 38.4 mmol, 1.0 eq.) with stirring for 30 minutes at 0° C., followed by the addition of thionyl chloride (4.57 g, 38.4 mmol, 1.0 eq.) with stirring for another 30 minutes at 0° C. To the resulting mixture under nitrogen was added dropwise a solution of benzylamine 5 (4.53 g, 42.3 mmol, 1.1 eq.) in anhydrous THF (25 mL) with stirring for 1.5 hours at 0° C. The reaction mixture was diluted with ethyl acetate and extracted with 2N NaOH (to pH 10). The aqueous phase was titrated with 2N HCl to pH 1-2 and then extracted with ethyl acetate. The organic phase was dried with sodium sulfate and concentrated in vacuo to give 1-Benzylcarbamoyl-cyclopropanecarboxylic acid as a white solid (4.39 g, 52.15%). $^1$H NMR (400 MHz, CDCl$_3$): 8.44 (br s, 1H), 7.37-7.33 (m, 2H), 7.32-7.26 (m, 3H), 1.82-1.70 (m, 4H).

Example 3

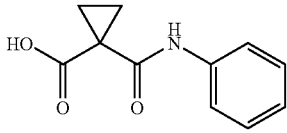

1-Phenylcarbamoyl-cyclopropanecarboxylic acid. To a mixture of cyclopropane-1,1-dicarboxylic acid (5.29 g, 40.7 mmol, 1.0 eq.) in anhydrous THF (50 mL) under nitrogen was added dropwise triethylamine (4.12 g, 40.7 mmol, 1.0 eq.) with stirring for 30 minutes at 0° C., followed by the addition of thionyl chloride (4.84 g, 40.7 mmol, 1.0 eq.) with stirring for another 30 minutes at 0° C. To the resulting mixture under nitrogen was added dropwise a solution of phenylamine 9 (4.17 g, 44.8 mmol, 1.1 eq.) in anhydrous THF (25 mL) with stirring for 1.5 hours at 0° C. The reaction mixture was diluted with ethyl acetate and extracted with 2N NaOH (to pH>10). The aqueous phase was titrated with 2N HCl to pH 1-2 and then extracted with ethyl acetate. The organic phase was dried with sodium sulfate and concentrated in vacuo to give 1-phenylcarbamoyl-cyclopropanecarboxylic acid as a white solid (5.08 g, 60.8%). $^1$H NMR (400 MHz, CDCl$_3$): 10.50 (br s, 1H), 7.56-7.54 (m, 2H), 7.35-7.31 (m, 2H), 7.15-7.10 (m, 1H), 1.94-1.91 (m, 2H), 1.82-1.79 (m, 2H).

Example 4

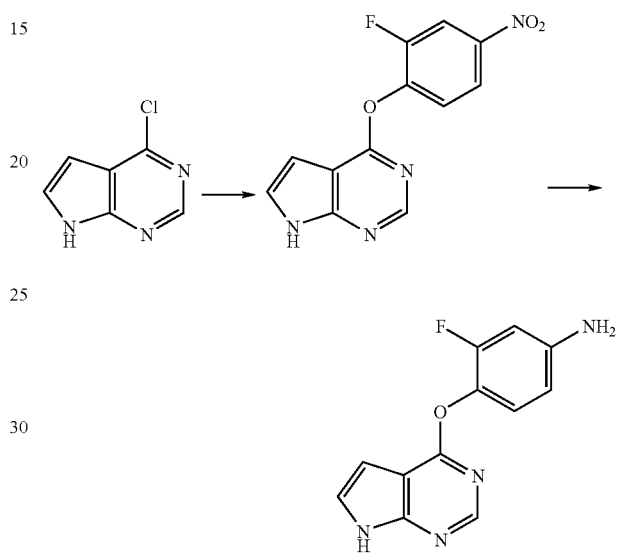

4-(2-Fluoro-4-nitro-phenoxy)-7H-pyrrolo[2,3-d]pyrimidine. To a sealed tube equipped with a magnetic stir bar was added 4-chloro-7H-pyrrolo[2,3-d]pyrimidine (1.0 g, 6.5 mmol, 1.0 eq.), 2-Fluoro-4-nitro-phenol (1.5 g, 9.5 mmol, 1.5 eq) and bromobenzene (5 ml). The mixture was stirred at 130° C. for 4 hours. The reaction mixture was then cooled to room temperature and ether was added (5 ml). After addition of ether the resulting precipitate was filtered and washed with ether. The product was recrystallized from methanol to give 4-(2-fluoro-4-nitro-phenoxy)-7H-pyrrolo[2,3-d]pyrimidine as an off white solid. (1.6 g, 89% yield). $^1$H NMR (400 MHz, DMSO): 12.44 (s, 1H), 8.41(dd, 1H), 8.34 (s, 1H), 8.24 (m, 1H), 7.80 (m, 1H), 7.61 (m, 1H), 6.69 (d, 1H); MS (ESI) for $C_{12}H_7FN_4O_3$: 275 (MH$^+$).

3-Fluoro-4-(7H-pyrrolo[2,3-d]pyrimidin-4-yloxy)-phenylamine. To a round bottom flask equipped with a magnetic stir bar was added 4-(2-fluoro-4-nitro-phenoxy)-7H-pyrrolo[2,3-d]pyrimidine (0.5 g, 2.0 mmol, 1.0 eq.), 5% PtS (20% by weight, 120 mg) ammonium formate (451 mg, 6 eq), and ethanol (20 ml). The reaction mixture was heated at reflux with stirring for 30 min upon which the reaction was filtered hot through celite. Removal of the ethanol was followed by the addition of 1N HCl, which was further washed twice with DCM (50 ml). The aqueous layer was basified and extracted with DCM. The organic layer was then washed twice with brine (50 ml) and dried over sodium sulfate. After removal of solvent in vacuo, 3-fluoro-4-(7H-pyrrolo[2,3-d]pyrimidin-4- yloxy)-phenylamine as a brownish solid was obtained (0.281 g, 63%). MS (ESI) for $C_{12}H_9FN_4O$: 244 (MH$^+$).

Example 5

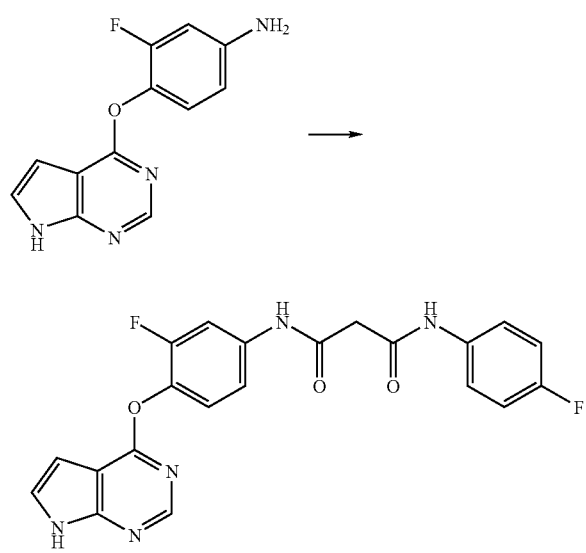

N-(4-Fluorophenyl)-N'-[3-fluoro-4-(7H-pyrrolo[2,3-d] pyrimidin-4-yloxy)phenyl]-propanediamide. To a round bottom flask equipped with a magnetic stir bar was added 3-fluoro-4-(7H-pyrrolo[2,3-d]pyrimidin-4-yloxy)-phenylamine (0.141 mg, 0.57 mmol, 1.0 eq.), 1-(4-fluoro-phenylcarbamoyl)-carboxylic acid (0.193 g, 0.88 mmol), HATU (0.584 g, 1.14 mmol), triethylamine (0.23 ml, 1.3 mmol) and anhydrous DMF (5 ml). The reaction mixture was stirred at room temperature overnight. The reaction mixture was diluted with H$_2$O (100 ml) and extracted with CHCl$_3$ (3×). The combined organic extractions were washed with H$_2$O (1×), sat'd NaHCO$_3$ (2×), 10% LiCl (3×), sat'd NaCl (1×), dried (Na$_2$SO$_4$), and concentrated in vacuo. The resulting crude residue was purified by HPLC to yield N-(4-fluorophenyl)-N'-[3-fluoro-4-(7H-pyrrolo[2,3-d]pyrimidin-4-yloxy) phenyl]propanediamide as a white solid (0.051 g, 21% yield). $^1$H NMR (400 MHz, DMSO): 12.30 (s, 1H), 10.49 (s, 1H), 10.28 (s, 1H), 8.29(s, 1H), 7.80 (dd, 1H), 7.65 (m, 2H), 7.51 (m, 1H), 7.40 (m, 2H), 7.19 (m, 2H), 6.58 (d, 1H), 3.49 (s, 2H); MS (ESI) for $C_{21}H_{15}F_2N_5O_3$: 424 (MH$^+$).

Example 6

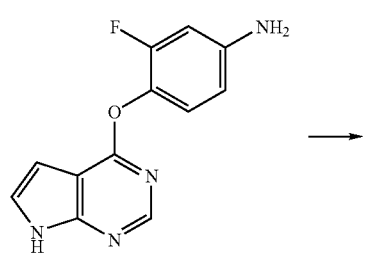

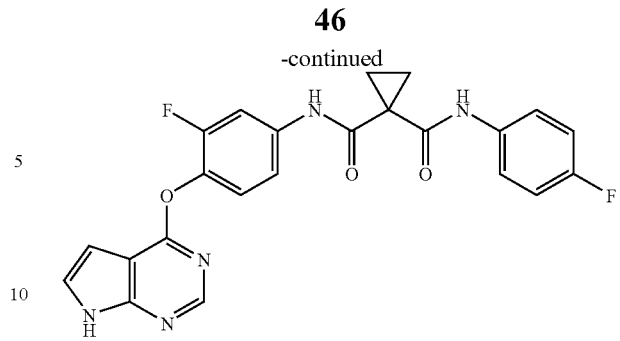

N-(4-fluorophenyl)-N'-[3-fluoro-4-(7H-pyrrolo[2,3-d]pyrimidin-4-yloxy)phenyl]-cyclopropane-1,1-dicarboxamide. To a round bottom flask equipped with a magnetic stir bar was added 3-fluoro-4-(7H-pyrrolo[2,3-d]pyrimidin-4-yloxy)-phenylamine (0.07 g, 0.29 mmol, 1.0 eq.), 1-(4-fluoro-phenylcarbamoyl)-cyclopropanecarboxylic acid (0.105 g, 0.32 mmol), HATU (0.304 g, 0.58 mmol), triethylamine (0.13 ml, 0.87 mmol), and anhydrous DMF (3 ml). The reaction mixture was stirred at room temperature overnight. The reaction mixture was diluted with H$_2$O (50 ml) and extracted with CHCl$_3$ (3×). The combined CHCl$_3$ extractions were washed with H$_2$O (1×), sat'd NaHCO$_3$ (2×), 10% LiCl (3×), sat'd NaCl (1×), dried (Na$_2$SO$_4$), and concentrated in vacuo. The resulting crude residue was purified by HPLC to yield N-(4-fluorophenyl)-N'-[3-fluoro-4-(7H-pyrrolo[2,3-d]pyrimidin-4-yloxy)phenyl]-cyclopropane-1,1-dicarboxamide as a white solid (0.011 g, 9.0% yield). $^1$H NMR (400 MHz, DMSO): 9.59 (bs, 1H), 8.47 (s, 1H), 7.85 (m, 2H), 7.65 (m, 3H), 7.48 (d, 1H), 7.36 (t, 1H), 7.19 (d, 1H), 7.15 (t, 3H), 1.44 (s, 5H); MS (ESI) for $C_{23}H_{17}F_2N_5O_3$: 450 (MH$^+$).

Example 7

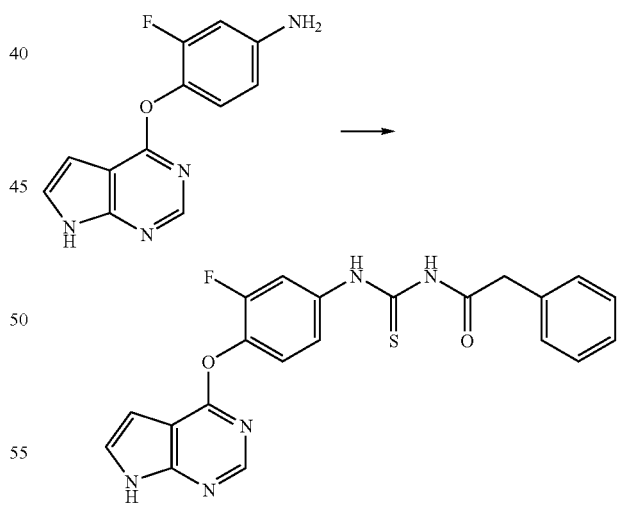

N-({[3-fluoro-4-(7H-pyrrolo[2,3-d]pyrimidin-4-yloxy) phenyl]amino}carbono-thioyl)-2-phenylacetamide. To a round bottom flask equipped with a magnetic stir bar was added 3-fluoro-4-(7H-pyrrolo[2,3-d]pyrimidin-4-yloxy)-phenylamine (0.07 g, 0.29 mmol, 1.0 eq.), toluene (10 ml), ethanol (10 ml) and phenyl-acetyl isothiocyanate (0.22 g, 1.3 mmol, 4.5 eq). The reaction mixture was stirred at room temperature overnight. After removal of the solvent the product was precipitated from methanol to give N-({[3-fluoro-4-

(7H-pyrrolo[2,3-d]pyrimidin-4-yloxy)phenyl]amino}carbonothioyl)-2-phenylacetamide as a white solid (0.6 g, 50% yield). ¹H NMR (400 MHz, DMSO): 12.49 (s, 1H), 12.35 (s, 1H), 12.82 (s, 1H), 8.32 (s, 1H), 7.89 (dd, 1H), 7.53 (t, 1H), 7.42 (d, 2H), 7.34 (d, 4H), 7.29 (m, 1H), 7.19 (d, 1H), 6.64 (d, 1H), 3.82 (s, 2H); MS (ESI) for $C_{21}H_{16}FN_5O_2S$: 422 (MH⁺).

Example 8

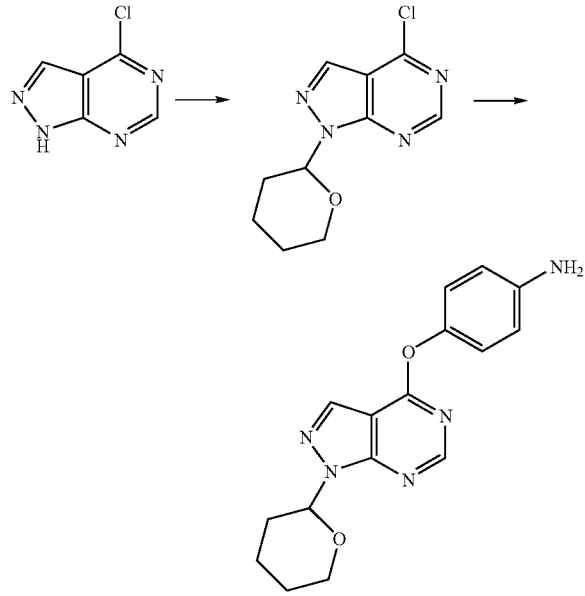

4-Chloro-1-(tetrahydro-pyran-2-yl)-1H-pyrazolo[3,4-d]pyrimidine. To a round bottom flask equipped with a magnetic stir bar was added 4-chloro-1H-pyrazolo[3,4-d]pyrimidine (2.0 g, 12.9 mmol, 1.0 eq.) and ethyl acetate. The mixture was heated to 50° C. After 10 minutes p-toluenesulfonic acid (50 mg) was added, followed by the addition of 2,3-dihydropurane (1.09 g, 15.5 mmol, 1.2 eq). The resulting reaction mixture was heated at 50° C. with stirring for 1 hour and was then cooled to room temperature at which time aqueous ammonia was added. After 5 minutes the organic layer was separated, and washed twice with water (100 ml) and once with brine (100 ml). The ethyl acetate was removed and petroleum ether was added. The mixture was heated and filtered thru cotton. Removal of the petroleum ether in vacuo afforded 4-chloro-1-(tetrahydro-pyran-2-yl)-1H-pyrazolo[3,4-d]pyrimidine as a light yellow colored solid (2.35 g, 77%). ¹H NMR (400 MHz, CDCl₃): 8.81(s, 1H), 8.22 (s, 1H), 6.05 (dd, 1H), 4.14 (m, 1H), 3.81 (m, 1H), 2.61 (m, 1H), 2.14 (m, 1H), 1.99 (m, 1H), 1.81 (m, 2H), 1.64 (m, 1H); MS (ESI) for $C_{10}H_{11}ClN_4O$: 239 (MH⁺).

4-[1-(Tetrahydro-pyran-2-yl)-1H-pyrazolo[3,4-d]pyrimidin-4-yloxy]-phenylamine. To a round bottom flask equipped with a magnetic stir bar was added 4-amino-phenol (0.251 g, 2.3 mmol, 1.1 eq) and DMF (3 ml). The mixture was cooled to 0° C. followed by the addition of NaH (0.13, 5.4 mmol, 2.7 eq). After 10 minutes 4-Chloro-1-(tetrahydro-pyran-2-yl)-1H-pyrazolo[3,4-d]pyrimidine (0.5 g, 2.1 mmol, 1.0 eq.) was added and the reaction was allowed to warm up to room temperature. After stirring at room temperature for 1 hour the reaction mixture was diluted with ethyl acetate (50 ml) and was washed (2×) water, (1×) NaHCO₃, (2×) 5% LiCl, and (1×) brine. The organic layer was dried over sodium sulfate and the solvent removed to give 4-[1-(tetrahydro-pyran-2-yl)-1H-pyrazolo[3,4-d]pyrimidin-4-yloxy]-phenylamine as a yellow solid (570 mg, 87%). ¹H NMR (400 MHz, CDCl₃): 8.56(s, 1H), 7.75 (s, 1H), 6.97 (d, 2H), 6.64 (d, 2H), 5.96 (dd, 1H), 5.21 (s, 2H), 3.96 (d, 1H), 3.72 (m, 1H), 2.42 (m, 1H), 2.01 (m, 1H), 1.87 (m, 1H), 1.76 (m, 1H), 1.57 (m, 2H); MS (ESI) for $C_{16}H_{17}N_5O_2$: 312 (MH⁺).

Example 9

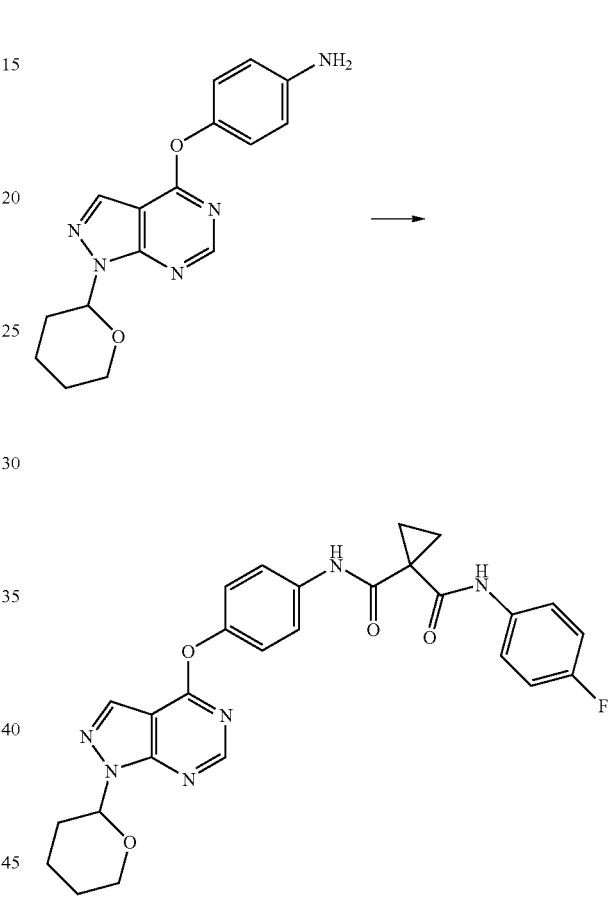

N-(4-Fluorophenyl)-N'-(4-{[1-(tetrahydro-2H-pyran-2-yl)-1H-pyrazolo[3,4-d]pyrimidin-4-yl]oxy}phenyl)cyclopropane-1,1-dicarboxamide. To a round bottom flask equipped with a magnetic stir bar was added 4-[1-(tetrahydro-pyran-2-yl)-1H-pyrazolo[3,4-d]pyrimidin-4-yloxy]-phenylamine (0.199 g, 0.63 mmol, 1.0 eq.), 1-(4-fluoro-phenylcarbamoyl)-cyclopropanecarboxylic acid (0.213 g, 0.95 mmol, 1.5 eq), HATU (0.607 g, 1.6 mmol, 2.5 eq), triethylamine (0.26 ml, 1.9 mmol, 3 eq), and anhydrous DMF (5 ml). The mixture was stirred at room temperature for 1 hour. The mixture was diluted with ethyl acetate, washed with (2×) H₂O (50 ml), sat'd NaHCO₃ (2×), 5% LiCl (3×), sat'd NaCl (1×), dried (Na₂SO₄), and concentrated in vacuo to give N-(4-fluorophenyl)-N'-(4-{[1-(tetrahydro-2H-pyran-2-yl)-1H-pyrazolo[3,4-d]pyrimidin-4-yl]oxy}phenyl)cyclopropane-1,1-dicarboxamide as a white solid (0.312 g, 95% yield). ¹H NMR (400 MHz, CDCl₃): 9.21 (s, 1H), 8.82 (bs, 1H), 8.56 (s, 1H), 7.96 (s, 2H), 7.65 (dd, 2H), 7.48 (m, 2H), 7.21 (m, 2H), 7.05 (t, 2H), 6.05 (dd, 1H), 3.78 (m, 1H), 2.61 (m, 1H), 2.16

(m, 1H), 2.14 (s,1H), 1.99 (m, 1H), 1.81 (m, 2H), 1.69 (m, 4H), 1.60 (s, 1H); MS (ESI) for $C_{27}H_{25}FN_7O_4$: 517 (MH+).

Example 10

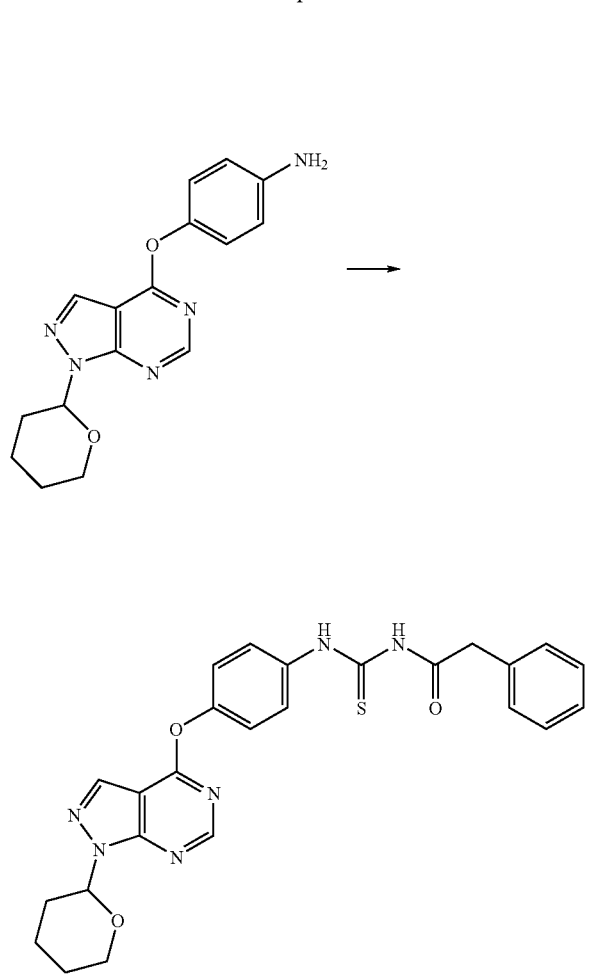

2-Phenyl-N-{[(4-{[1-(tetrahydro-2H-pyran-2-yl)-1H-pyrazolo[3,4-d]pyrimidin-4-yl]oxy}phenyl)amino]carbonothioyl}acetamide. To a round bottom flask equipped with a magnetic stir bar was added 4-[1-(tetrahydro-pyran-2-yl)-1H-pyrazolo[3,4-d]pyrimidin-4-yloxy]-phenylamine (0.199 g, 0.63 mmol, 1.0 eq.), toluene (10 ml), ethanol (10 ml) and phenyl-acetyl isothiocyanate (0.33 g, 2.0 mmol, 3.0 eq). The reaction mixture was stirred at room temperature overnight. After removal of solvent in vacuo, the product was separated by flash chromatography using a 3:1 hexane/ethyl acetate solution as the eluent to give 2-phenyl-N-{[(4-{[1-(tetrahydro-2H-pyran-2-yl)-1H-pyrazolo[3,4-d]pyrimidin-4-yl]oxy}phenyl)amino]carbonothioyl}acetamide (0.17 g, 54% yield). $^1$H NMR (400 MHz, DMSO): 12.39 (s, 1H), 11.78 (s, 1H), 8.59 (s, 1H), 8.20 (s, 1H), 7.71 (d, 2H), 7.53 (t, 1H), 7.34 (m, 5H), 7.26 (m, 1H), 5.97 (d, 1H), 3.94 (d, 1H), 3.73 (s, 2H), 3.72 (m 1H), 3.40 (s, 2H), 2.05 (m, 1H), 1.93 (m, 1H), 1.77 (m, 1H), 1.58 (m, 1H); MS (ESI) for $C_{25}H_{24}N_6O_3S$: 489 (MH+).

Example 11

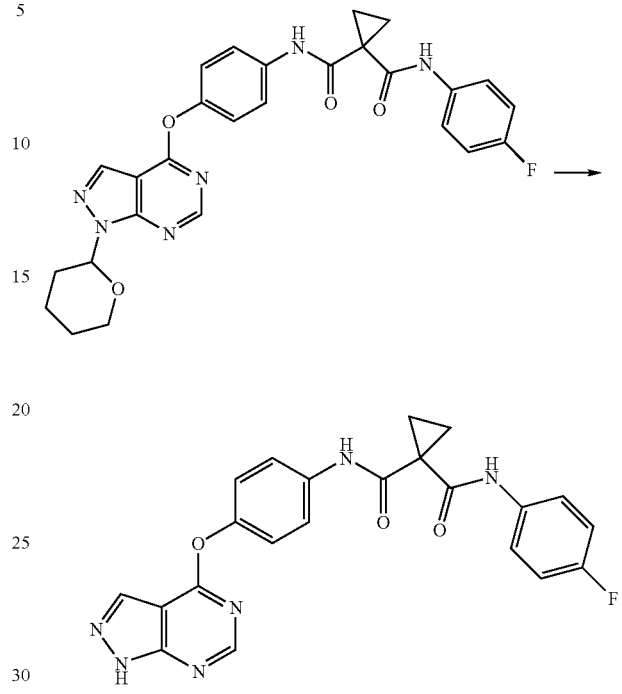

N-(4-fluorophenyl)-N'-[4-(1H-pyrazolo[3,4-d]pyrimidin-4-yloxy)phenyl]cyclopropane-1,1-dicarboxamide. To a round bottom flask equipped with a magnetic stir bar was added N-(4-fluorophenyl)-N'-(4-{[1-(tetrahydro-2H-pyran-2-yl)-1H-pyrazolo[3,4-d]pyrimidin-4-yl]oxy}phenyl)cyclopropane-1,1-dicarboxamide (0.050 mg, 0.10 mmol, 1.0 eq.) and 4M HCl/Dioxane (5 ml). After 5 minutes ether was added. The resulting solid was filtered and washed twice with ether. The solid was further dried under vacuum to give N-(4-fluorophenyl)-N'-[4-(1H-pyrazolo[3,4-d]pyrimidin-4-yloxy)phenyl]cyclopropane-1,1-dicarboxamide (0.027 g, 67% yield). $^1$H NMR (400 MHz, DMSO): 10.20 (s, 1H), 10.10 (s, 1H), 8.50 (s, 1H), 8.06 (s, 1H), 7.75 (m, 2H), 7.67 (m, 2H), 7.27 (m, 2H), 7.13 (m, 2H), 4.47 (bs, 1H), 1.47 (s, 4H); MS (ESI) for $C_{22}H_{17}FN_6O_3$: 433 (MH+).

Example 12

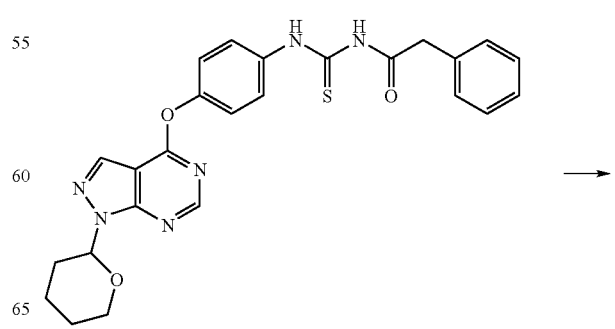

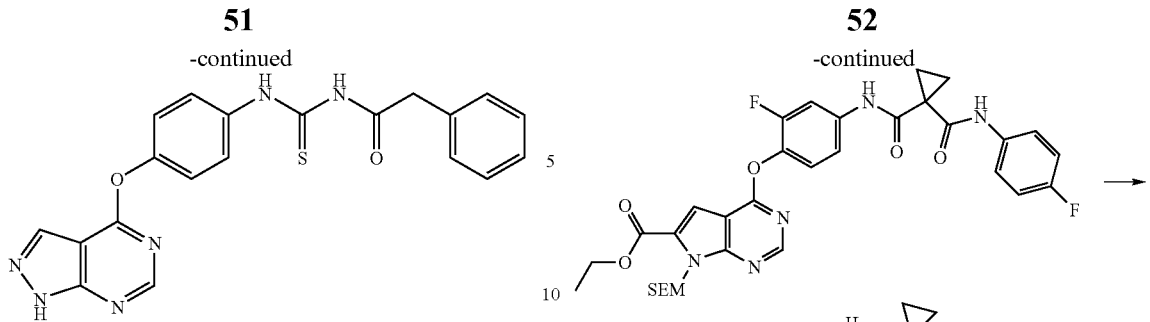

2-Phenyl-N-({[4-(1H-pyrazolo[3,4-d]pyrimidin-4-yloxy)phenyl]amino}carbonothioyl)-acetamide. To a round bottom flask equipped with a magnetic stir bar was added 2-phenyl-N-{[(4-{[1-(tetrahydro-2H-pyran-2-yl)-1H-pyrazolo[3,4-d]pyrimidin-4-yl]oxy}phenyl)amino]-carbonothioyl}acetamide (0.070 g, 0.14 mmol, 1.0 eq.) and 4M HCl/Dioxane (5 ml). After 5 minutes ether was added. The resulting solid was filtered and washed twice with ether. The solid was further dried under vacuum to give 2-phenyl-N-({[4-(1H-pyrazolo[3,4-d]pyrimidin-4-yloxy)phenyl]amino}carbonothioyl)acetamide (0.057 g, 96% yield). $^1$H NMR (400 MHz, DMSO): 12.40 (s, 1H), 11.79 (s, 1H), 8.52 (s, 1H), 8.14 (s, 1H), 7.71 (d, 2H), 7.33 (m, 8H), 3.83 (s, 2H); MS (ESI) for $C_{20}H_{16}N_6O_2S$: 403 (MH$^+$).

Example 13

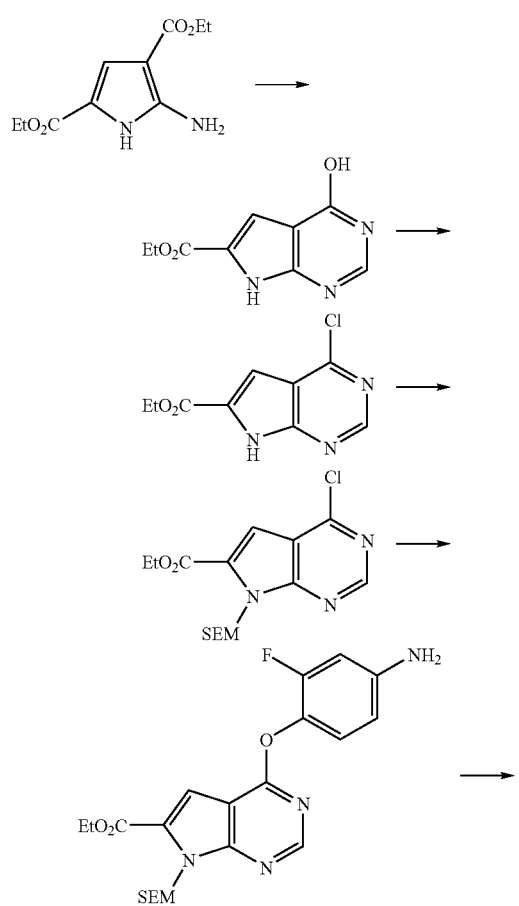

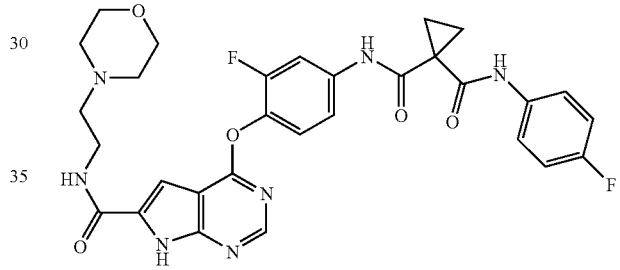

5-Amino-1H-pyrrole-2,4-dicarboxylic acid diethyl ester. To a round bottom flask equipped with a magnetic stir bar was added 1-ethoxy-2-ethoxycarbonyl-vinyl-ammonium chloride (10 g, 51.2 mmol, 1.0 eq.) and sodium ethoxide (4.49 g, 56.3 mmol, 1.1 eq) in ethyl acetate (100 ml). The mixture was stirred for 45 minutes at which time the sodium ethoxide was filtered. To the filtrate was added ethyl bromopyruvate (5.85 g, 28.2 mmol, 0.5 eq). The reaction was then heated to 60° C. for 20 min. The reaction mixture was directly filtered through a silica gel plug. After removal of the solvent in vacuo, the crude product was filtered through another silica gel plug, and raising with a 3:7 hexane/ethyl acetate solution. The combined filtrate was concentrated in vacuo to give 5-amino-1H-pyrrole-2,4-dicarboxylic acid diethyl ester as a yellow solid (3.07 g, 27% yield). $^1$H NMR (400 MHz, DMSO): 10.82 (s, 1H), 6.79 (s, 1H), 5.87 (s, 2H), 4.14 (m, 4H), 1.22 (m, 6H); MS (ESI) for $C_{10}H_{14}N_2O_4$: 227 (MH$^+$).

4-Hydroxy-7H-pyrrolo[2,3-d]pyrimidine-6-carboxylic acid ethyl ester. To a round bottom flask equipped with a magnetic stir bar was added 5-amino-1H-pyrrole-2,4-dicarboxylic acid diethyl ester (0.54 g, 2.3 mmol, 1.0 eq.) and triethyl orthoformate. The mixture was heated at 140° C. for 1 hour at which time the triethyl orthoformate was removed. After removed of the solvent 50 ml of 7N ammonia in methanol was added and the reaction was stirred overnight. A precipitate was formed, which was filtered, washed with methanol and ether, and dried in vacuo to give 4-hydroxy-7H- pyrrolo[2,3-d]pyrimidine-6-carboxylic acid ethyl ester as a cream solid (0.15 mg, 30% yield). $^1$H NMR (400 MHz, DMSO): 12.39 (bs, 1H), 7.99 (s, 1H), 7.10 (s, 1H), 4.32 (q, 2H), 3.32 (bs, 1H), 1.31 (t, 3H); MS (ESI, negative) for $C_9H_9N_3O_3$: 206 (M-H).

4-Chloro-7H-pyrrolo[2,3-d]pyrimidine-6-carboxylic acid ethyl ester. To a round bottom flask equipped with a magnetic stir bar was added 4-hydroxy-7H-pyrrolo[2,3-d]pyrimidine-6-carboxylic acid ethyl ester (0.300 g, 1.3 mmol, 1.0 eq.), thionyl chloride (5 ml), and DMF (1 ml). The mixture was refluxed for 4 hour at which time the reaction was poured onto ice and NaHCO$_3$. The aqueous layer was then extracted with ethyl acetate (2×). The organic layer was washed with water and brine, dried (Na2SO4), and concentrated in vacuo to give 4-chloro-7H-pyrrolo[2,3-d]pyrimidine-6-carboxylic acid ethyl ester as a brown solid (0.35 g 100% yield). MS (ESI, negative) for $C_9H_8ClN_3O_2$: 224 (M-H).

4-Chloro-7-(2-trimethylsilanyl-ethoxymethyl)-7H-pyrrolo[2,3-d]pyrimidine-6-carboxylic acid ethyl ester. To a round bottom flask equipped with a magnetic stir bar was added 4-chloro-7H-pyrrolo[2,3-d]pyrimidine-6-carboxylic acid ethyl ester (0.13 g, 0.58 mmol, 1.0 eq.) and DMF (3 ml). The mixture was cooled to 0° C. followed by the addition of NaH (0.028 g, 0.70 mmol, 1.2 eq) with stirring. After stirring for 10 minutes SEM-CL (0.106 g, 0.64 mmol, 1.1 eq) was added and the reaction was allowed to warm to room temperature with stirring for 1 hour. The reaction was diluted with ethyl acetate (50 ml), washed (2×) water, (1×) NaHCO$_3$, (2×) 5% LiCl, (1×) brine, and dried over sodium sulfate, and concentrated in vacuo to give 4-chloro-7-(2-trimethylsilanyl-ethoxymethyl)-7H-pyrrolo[2,3-d]pyrimidine-6-carboxylic acid ethyl ester as a cream solid (0.17 g, 84%). MS (ESI) for $C_{15}H_{22}ClN_3O_3Si$: 356 (MH$^+$).

4-Chloro-7-(2-trimethylsilanyl-ethoxymethyl)-7H-pyrrolo[2,3-d]pyrimidine-6-carboxylic acid ethyl ester. To a round bottom flask equipped with a magnetic stir bar was added 4-aminophenol (0.146 g, 1.16 mmol, 2.0 eq) and DMF (3 ml). The mixture was cooled to 0° C. followed by the addition of NaH (0.051 g, 2.6 mmol, 2.2 eq). After stirring for 10 minutes 4-chloro-7-(2-trimethylsilanyl-ethoxymethyl)-7H-pyrrolo[2,3-d]pyrimidine-6-carboxylic acid ethyl ester (0.17 g, 0.47 mmol, 1.0 eq.) was added and the reaction was allowed to warm to room temperature, and stirred at room temperature for 1 hour. The reaction mixture was diluted with ethyl acetate (50 ml), washed (2×) water, (1×) NaHCO$_3$, (2×) 5% LiCl, (1×) brine, and dried over sodium sulfate. Upon removal of solvent in vacuo, 4-chloro-7-(2-trimethylsilanyl-ethoxymethyl)-7H-pyrrolo[2,3-d]pyrimidine-6-carboxylic acid ethyl ester was obtained as a cream solid (0.18 g, 85%). MS (ESI) for $C_{21}H_{27}FN_4O_4Si$: 447 (MH$^+$).

4-(2-Fluoro-4-{[1-(4-fluoro-phenylcarbamoyl)-cyclopropanecarbonyl]-amino}-phenoxy)-7-(2-trimethylsilanyl-ethoxymethyl)-7H-pyrrolo[2,3-d]pyrimidine-6-carboxylic acid ethyl ester. To a round bottom flask equipped with a magnetic stir bar was added 4-chloro-7-(2-trimethylsilanyl-ethoxymethyl)-7H-pyrrolo[2,3-d]pyrimidine-6-carboxylic acid ethyl ester (0.178 g, 0.39 mmol, 1.0 eq.), 1-(4-fluoro-phenylcarbamoyl)-cyclopropanecarboxylic acid (0.133 g, 0.59 mmol, 1.5 eq), HATU (0.379 g, 0.98 mmol, 2.5 eq), TEA (0.17 ml, 1.17 mmol, 3 eq), and dry DMF (5 ml). The mixture was stirred at room temperature for 3 hours. The reaction mixture was diluted with ethyl acetate and washed with (2×) H$_2$O (50 ml), sat'd NaHCO$_3$ (2×), 5% LiCl (3×), sat'd NaCl (1×), dried (Na$_2$SO$_4$), and concentrated in vacuo, giving 4-(2-fluoro-4-{[1-(4-fluoro-phenylcarbamoyl)-cyclopropanecarbonyl]-amino}-phenoxy)-7-(2-trimethylsilanyl-ethoxymethyl)-7H-pyrrolo[2,3-d]pyrimidine-6-carboxylic acid ethyl ester as a cream solid (0.138 g, 53% yield). MS (ESI) for $C_{32}H_{35}F_2N_5O_6Si$: 517 (MH$^+$).

4-(2-Fluoro-4-{[1-(4-fluoro-phenylcarbamoyl)-cyclopropanecarbonyl]-amino}-phenoxy)-7-(2-trimethylsilanylethoxymethyl)-7H-pyrrolo[2,3-d]pyrimidine-6-carboxylic acid 7. To a round bottom flask equipped with a magnetic stir bar was added 4-(2-fluoro-4-{[1-(4-fluoro-phenylcarbamoyl)-cyclopropanecarbonyl]-amino}-phenoxy)-7-(2-trimethylsilanyl-ethoxymethyl)-7H-pyrrolo[2,3-d]pyrimidine-6-carboxylic acid ethyl ester (0.069 g, 0.10 mmol, 1.0 eq.), and a 1M tetrabutylammonium fluoride solution (5 ml). The reaction was allowed to stir at overnight. The reaction was diluted with ethyl acetate, washed with (2×) H$_2$O (50 ml), 1M HCl (2×), sat'd NaCl (1×), dried (Na$_2$SO$_4$), and concentrated in vacuo, affording 4-(2-fluoro-4-{[1-(4-fluoro-phenylcarbamoyl)-cyclopropanecarbonyl]-amino}-phenoxy)-7-(2-trimethylsilanyl-ethoxymethyl)-7H-pyrrolo[2,3-d]pyrimidine-6-carboxylic acid as a white solid (0.048 g, 74% yield). MS (ESI) for $C_{30}H_{31}F_2N_5O_6Si$: 624 (MH$^+$).

Cyclopropane-1,1-dicarboxylic acid {3-fluoro-4-[6-(2-morpholin-4-yl-ethylcarbamoyl)-7-(2-trimethylsilanyl-ethoxymethyl)-7H-pyrrolo[2,3-d]pyrimidin-4-yloxy]-phenyl}-amide(4-fluoro-phenyl)-amide. To a round bottom flask equipped with a magnetic stir bar was added 4-(2-Fluoro-4-{[1-(4-fluoro-phenylcarbamoyl)-cyclopropanecarbonyl]-amino}-phenoxy)-7-(2-trimethylsilanyl-ethoxymethyl)-7H-pyrrolo[2,3-d]pyrimidine-6-carboxylic acid (0.05 g, 0.08 mmol, 1.0 eq.), 2-Morpholin-4-yl-ethylamine (0.016 ml, 0.12 mmol, 1.5 eq), HATU (0.076 g, 0.2 mmol, 2.5 eq), TEA (0.033 ml, 0.24 mmol, 3.0 eq), and dry DMF (5 ml). The resulting mixture was stirred at room temperature for 1 hour. The reaction mixture was diluted with ethyl acetate, washed with (2×) H$_2$O (50 ml), sat'd NaHCO$_3$ (2×), 5% LiCl (3×), sat'd NaCl (1×), dried (Na$_2$SO$_4$), and concentrated in vacuo, giving cyclopropane-1,1-dicarboxylic acid {3-fluoro-4-[6-(2-morpholin-4-yl-ethylcarbamoyl)-7-(2-trimethylsilanyl-ethoxymethyl)-7H-pyrrolo[2,3-d]pyrimidin-4-yloxy]-phenyl}-amide(4-fluoro-phenyl)-amide as a cream solid (0.049 g, 83% yield). MS (ESI) for $C_{36}H_{43}F_2N_7O_6Si$: 736 (MH$^+$).

N-{3-Fluoro-4-[(6-{[(2-morpholin-4-ylethyl)amino]carbonyl}-7H-pyrrolo[2,3-d]pyrimidin-4-yl)oxy]phenyl}-N'-(4-fluorophenyl)cyclopropane-1,1-dicarboxamide. To a round bottom flask equipped with a magnetic stir bar was added cyclopropane-1,1-dicarboxylic acid {3-fluoro-4-[6-(2-morpholin-4-yl-ethylcarbamoyl)-7-(2-trimethylsilanyl-ethoxymethyl)-7H-pyrrolo[2,3-d]pyrimidin-4-yloxy]-phenyl}-amide(4-fluoro-phenyl)-amide (0.049 g, 0.07 mmol, 1.0 eq.) and a 1M tetrabutylammonium fluoride solution (5 ml). The reaction was heated to reflux for 1 hour. The reaction was diluted with ethyl acetate, and was washed with (2×) H$_2$O (50 ml), sat'd NaCl (1×), dried (Na$_2$SO$_4$), and concentrated in vacuo. The crude product was purified by flash column chromatography using 3% methanol and DCM as the eluent, giving N-{3-fluoro-4-[(6-{[(2-morpholin-4-ylethyl)amino]carbonyl}-7H-pyrrolo[2,3-d]pyrimidin-4-yl)oxy]phenyl}-N'-(4-fluorophenyl)cyclopropane-1,1-dicarboxamide as a white solid (0.014 g, 35% yield). $^1$H NMR (400 MHz, DMSO): 12.92 (s, 1H), 10.39 (bs, 1H), 10.36 (s, 1H), 10.04 (s, 1H), 9.11 (m, 1H), 8.37 (s, 1H), 7.83 (d, 1H), 7.66 (m, 2H), 7.46 (m, 1H), 7.40 (m, 1H), 7.15 (t, 2H), 3.98 (d, 2H), 3.77 (m, 3H), 3.56 (d, 2H), 3.16 (m, 2H), 3.02 (m, 3H), 1.59 (m, 2H), 1.36 (m, 2H); MS (ESI) for $C_{30}H_{29}F_2N_7O_5$: 606 (MH$^+$).

Example 14

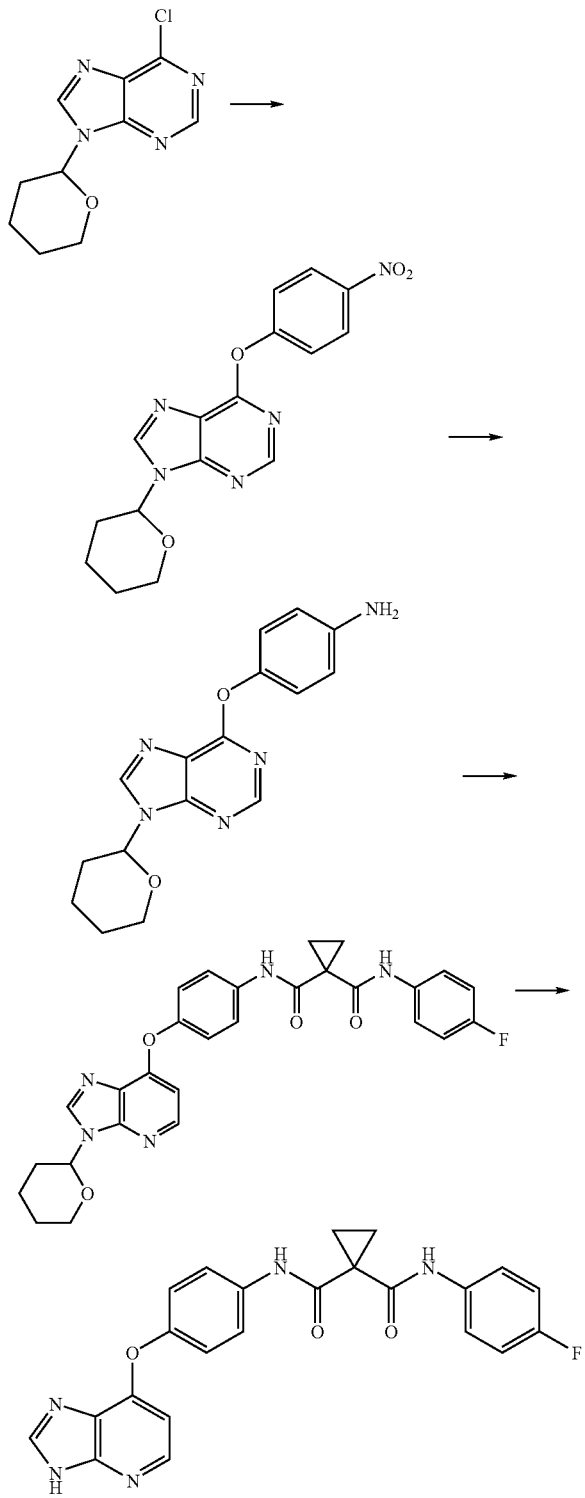

6-(4-Nitro-phenoxy)-9-(tetrahydro-pyran-2-yl)-9H-purine: To a stirred slurry of 6-chloro-9-(tetrahydro-pyran-2-yl)-9H-purine (2.3 g, 10 mmol, 3 equiv) in anhydrous 1,2-dichloroethane (60 mL) was added a solution of 4-nitrophenol (2.3 g, 10 mmol, 3 equiv), DABCO (1.12 g, 1 mmol, 1 equiv) and triethylamine (3.03 g, 4.18 mL, 3 mmol, 3 equiv) in anhydrous 1,2-dichloroethane (5 mL). The mixture was stirred at room temperature for 1 hour. The reaction mixture was diluted with DCM (25 mL), washed with saturated solution of NaHCO$_3$. The aqueous layer was re-extracted with DCM. The combined organic extracts were dried over MgSO$_4$, filtered followed by solvent evaporation, giving 6-(4-nitro-phenoxy)-9-(tetrahydro-pyran-2-yl)-9H-purine (4 g, >99% yield). $^1$H NMR (400 MHz, CDCl$_3$): δ 8.6 (s, 1H), 8.3 (m, 2H), 8.25 (s, 1H), 7.60 (m, 2H), 5.8 (m, 1H), 4.20 (m, 1H), 3.8 (m, 1H), 2.20 (m, 3H), 1.80 (m, 3H). MS (ESI) for C$_{16}$H$_{15}$N$_5$O$_4$: 342 (MH$^+$).

4-[9-(Tetrahydro-pyran-2-yl)-9H-purin-6-yloxy]-phenylamine: To a round bottom flask equipped with a magnetic stir bar was added 6-(4-nitro-phenoxy)-9-(tetrahydro-pyran-2-yl)-9H-purine (4 g, 12.86 mmol, 1.0 eq.), 5% PtS (20% by weight, 800 mg), ammonium formate (3.2 g, 51.44 eq), and ethanol (100 ml). The reaction was stirred at reflux for 30 min upon which the reaction was filtered hot through celite. Removal of the ethanol was followed by the addition of 1N HCl, which was further washed twice with DCM (50 ml). The aqueous layer was basified and extracted with DCM. The organic layer was then washed twice with brine (50 ml) and dried over sodium sulfate. After removal of the DCM in vacuo, 4-[9-(tetrahydro-pyran-2-yl)-9H-purin-6-yloxy]-phenylamine was obtained (3 g, 83%) as a solid. $^1$H NMR (400 MHz, CDCl$_3$): δ 8.4 (s, 1H), 8.2 (s, 1H), 7.0 (m, 2H), 6.75 (m, 2H), 5.8 (m, 1H), 4.20 (m, 1H), 4.0 (m, 2H), 3.8 (m, 1H), 2.20 (m, 3H), 1.80 (m, 3H). MS (ESI) for C$_{16}$H$_{17}$N$_5$O$_2$: 312 (MH$^+$).

N-(4-Fluorophenyl)-N'-(4-{[9-(tetrahydro-2H-pyran-2-yl)-9H-purin-6-yl]oxy}phenyl)cyclopropane-1,1-dicarboxamide: To a mixture of 4-[9-(tetrahydro-pyran-2-yl)-9H-purin-6-yloxy]-phenylamine (0.311 g, 1 mmol) and 1-(4-fluorophenylcarbamoyl)-cyclopropanecarboxylic acid (0.334 g, 1.5 mmol) in DMF (5 mL) was added TEA (216 μL, 2 mmol) followed by HATU (0.76 g, 2 mmol). The resulting solution was stirred overnight at room temperature. The reaction mixture was dumped into water (25 mL) and extracted with EtOAc (2×). The combined organic extracts were washed with 10% LiCl$_{(aq.)}$ (4×), satd. NaHCO$_{3(aq)}$ (2×), water, (1×) and brine (1×), followed by drying over MgSO$_4$ and concentration in vacuo. The crude solids were purified by flash chromatography (silica gel, 1:1 EtOAc:Hexanes containing 2% 7N NH$_3$ in MeOH), affording N-(4-fluorophenyl)-N'-(4-{[9-(tetrahydro-2H-pyran-2-yl)-9H-purin-6-yl]oxy}phenyl)cyclopropane-1,1-dicarboxamide (0.430 g, 83% yield) as a solid. $^1$H NMR (400 MHz, CDCl$_3$): δ 9.50 (s, 1H), 8.95 (s, 1H), 8.45 (s, 1H), 7.60 (m, 2H), 7.45 (m, 2H), 7.20 (m, 2H), 7.0 (m, 2H), 5.8 (m, 1H), 4.20 (m, 1H), 3.8 (m, 1H), 2.20 (m, 3H), 1.80 (m, 2H), 1.7 (m, 5H). MS (ESI) for C$_{27}$H$_{25}$FN$_6$O$_4$: 517 (MH$^+$).

N-(4-Fluorophenyl)-N'-[4-(9H-purin-6-yloxy)phenyl]cyclopropane-1,1-dicarboxamide: To a solution of N-(4-fluorophenyl)-N'-(4-{[9-(tetrahydro-2H-pyran-2-yl)-9H-purin-6-yl]oxy}phenyl)-cyclopropane-1,1-dicarboxamide (430 mg, 0.83 mmol) in 30 mL of dioxane was added 3 mL of 4N HCl in dioxane. The reaction mixture was stirred at room temperature for 1 h. After removal of solvent in vacuo, the reaction mixture triturated with ether, affording N-(4-fluorophenyl)-N'-[4-(9H-purin-6-yloxy)phenyl]cyclopropane-1,1-dicarboxamide (300 mg, 83% yield) as a colorless solid. $^1$H NMR (400 MHz, DMSO, d$_6$): δ 10.20 (s, 1H), 10.10 (s, 1H), 8.6 (s, 1H), 8.4 (s, 1H), 7.6-7.8 (m, 4H), 7.1-7.3 (m, 4H), 1.45 (s, 4H). MS (ESI) for $C_{22}H_{17}FN_6O_3$: 433 (MH$^+$).

Example 15

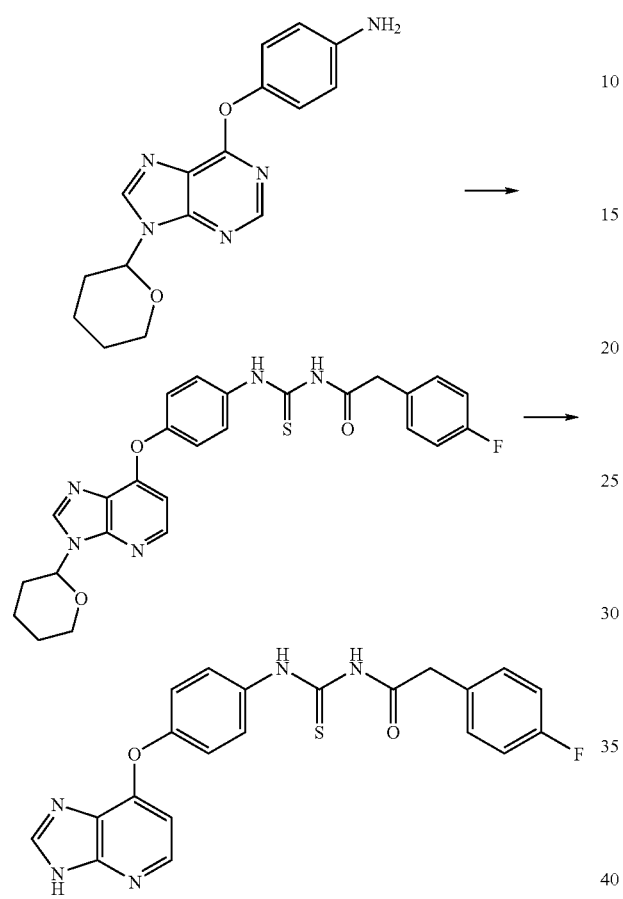

2-Phenyl-N-{[(4-{[9-(tetrahydro-2H-pyran-2-yl)-9H-purin-6-yl]oxy}phenyl) amino]-carbonothioyl}acetamide: To a round bottom flask equipped with a magnetic stir bar was added 4-[9-(Tetrahydro-pyran-2-yl)-9H-purin-6-yloxy]-phenylamine (1.1 g, 3.60 mmol, 1.0 eq.), DCM (10 ml) and phenyl-acetyl isothiocyanate (0.643 g, 3.60 mmol, 1 eq). The reaction mixture was stirred at room temperature overnight. After removal of the solvent the product was purified by flash column chromatography on silica gel to give 2-phenyl-N-{[(4-{[9-(tetrahydro-2H-pyran-2-yl)-9H-purin-6-yl]oxy}phenyl)amino]-carbonothioyl}acetamide as a white solid (400 mg, 25% yield). $^1$H NMR (400 MHz, CDCl$_3$): δ 12.40 (s, 1H), 8.80 (s; 1H), 8.60 (s, 1H), 8.30 (s, 1H), 7.80 (m, 2H), 7.20 (m, 7H), 5.9 (m, 1H), 4.20 (m, 1H), 3.8 (m, 2H), 2.20 (m, 3H), 1.80 (m, 4H). MS (ESI) for $C_{25}H_{24}N_6O_3S$: 489 (MH$^+$).

2-Phenyl-N-({[4-(9H-purin-6-yloxy)phenyl]amino}carbonothioyl)acetamide: To 2-phenyl-N-{[(4-{[9-(tetrahydro-2H-pyran-2-yl)-9H-purin-6-yl]oxy}phenyl)-amino]carbonothioyl}acetamide (190 mg, 0.38 mmol) in 30 mL of dioxane was added 3 mL of 4N HCl in dioxane and let to stir for 1 h. On concentration of the reaction mixture and trituration with ether yielded 2-phenyl-N-({[4-(9H-purin-6-yloxy)phenyl]amino}carbonothioyl)acetamide (102 mg, 65% yield) as a colorless solid. $^1$H NMR (400 MHz, DMSO d$_6$): δ 12.40 (s, 1H), 11.80 (s, 1H), 8.6 (s, 1H), 8.4 (s, 1H), 7.70 (m, 2H), 7.35 (m, 7H), 3.8 (s, 2H). MS (ESI) for $C_{20}H_{16}N_6O_2S$: 433 (MH$^+$).

Synthesis of Bridged Bicyclics

The following describes synthesis of bridged bicyclics with appended leaving groups for use as, for example, alkylating agents. In the context of this invention, these alkylating agents are used, for example, to make intermediates or to derivatize intermediates both of which are used to make compounds of the invention. The invention is not limited to alkylation chemistry to append such bridged bicyclics, but rather the aforementioned description is meant only to be illustrative of an aspect of the invention.

Example 16

1,4:3,6-dianhydro-2-O-methyl-5-O-(methylsulfonyl)-D-glucitol: To a solution of 1,4:3,6-dianhydro-2-O-methyl-D-glucitol (1.19 g, 7.4 mmol) in dichloromethane was added pyridine (1 mL, 12.36 mmol) followed by methanesulfonyl chloride (0.69 mL, 8.92 mmol) and the mixture was allowed to stir at room temperature over 12 hours. The solvent was removed and the amorphous residue was partitioned with ethyl acetate and 0.1M aqueous hydrochloric acid. The aqueous phase was extracted once with additional ethyl acetate and the combined organic layers were washed with saturated aqueous sodium chloride then dried over anhydrous magnesium sulfate. Filtration and concentration followed by drying in vacuo afforded 1,4:3,6-dianhydro-2-O-methyl-5-O-(methylsulfonyl)-D-glucitol (1.67 g, 94% yield) as a colorless oil. GC/MS calculated for $C_8H_{14}SO_6$: 238 (M$^+$).

Example 17

1,4:3,6-dianhydro-5-O-(phenylcarbonyl)-D-fructose ethylene glycol acetal: A solution of 1,4:3,6-dianhydro-5-O-(phenylcarbonyl)-D-fructose (2.00 g, 8.06 mmol), ethylene glycol (5.00 g, 80.6 mmol), and p-toluenesulfonic acid (1.53 g, 8.06 mmol) in benzene (100 mL) was refluxed for 90 min using a Dean-Stark Trap apparatus. The reaction mixture was diluted with ethyl acetate (100 mL), washed with saturated aqueous sodium bicarbonate (2×50 mL) then brine (50 mL), and dried over anhydrous sodium sulfate. Filtration, concentration and column chromatography on silica (1:1 hexane/ethyl acetate) provided 1.44 g (61% yield) of 1,4:3,6-dianhydro-5-O-(phenylcarbonyl)-D-fructose ethylene glycol acetal as a colorless solid. $^1$H NMR (400 MHz; CDCl$_3$): 8.08 (m, 2H), 7.58 (m, 1H), 7.54 (m, 2H), 5.38 (dd, 1H), 4.97 (t, 1H), 4.21-4.02 (m, 7H), 3.86 (d, 1H), 3.75 (d, 1H).

Example 18

1,4:3,6-dianhydro-D-fructose ethylene glycol acetal: To a solution of 1,4:3,6-dianhydro-5-O-(phenylcarbonyl)-D-fructose ethylene glycol acetal (1.44 g, 4.93 mmol) in methanol (40 mL) was added 50% aqueous sodium hydroxide (0.38 g, 4.75 mmol) and the mixture was stirred at room temperature for 30 minutes. Neutralization with 1M HCl, followed by concentration and column chromatography on silica (1:2 hexane/ethyl acetate) provided 0.74 g (80% yield) of 1,4:3,6-dianhydro-D-fructose ethylene glycol acetal as a colorless solid. $^1$H NMR (400 MHz; CDCl$_3$): 4.60 (t, 1H), 4.32 (m, 1H), 4.14 (d, 1H), 4.05-3.98 (m, 5H), 3.82 (s, 2H), 3.62 (dd, 1H), 2.65 (d, 1H).

1,4:3,6-dianhydro-5-O-(methylsulfonyl)-D-fructose ethylene glycol acetal: To a solution of 1,4:3,6-dianhydro-D-fructose ethylene glycol acetal (0.74 g, 3.93 mmol) and triethylamine (1.20 g, 11.86 mmol) in dichloromethane (40 mL) was added methanesulfonyl chloride (0.90 g, 7.88 mmol) at 0° C. under nitrogen. The solution was warmed to room temperature and stirred for 13 h. Dichloromethane (50 mL) was added, and the organic layer was washed with saturated aqueous sodium bicarbonate (30 mL), water (30 mL), and brine (30 mL) then dried over anhydrous sodium sulfate. Filtration and concentration provided 1.02 g (97%) of 1,4:3,6-dianhydro-5-O-(methylsulfonyl)-D-fructose ethylene glycol acetal as a yellow oil. $^1$H NMR (400 MHz; CDCl$_3$): 5.08 (m, 1H), 4.82 (t, 1H), 4.13 (dd, 1H), 4.04 (m, 4H), 3.93 (dd, 1H), 3.87 (d, 1H), 3.81 (d, 1H), 3.13 (s, 3H).

Example 19

1,4:3,6-dianhydro-2-deoxy-2-methylidene-D-arabino-hexitol: To a solution of 1,4:3,6-dianhydro-2-deoxy-2-methylidene-5-O-(phenylcarbonyl)-D-arabino-hexitol (329 mg, 1.34 mmol) in methanol (10 mL) was added 50% aqueous sodium hydroxide (95 mg, 1.19 mmol) and the mixture was stirred at room temperature for 30 minutes. Neutralization with 4M hydrogen chloride in 1,4-dioxane followed by concentration and column chromatography on silica (1:1 hexane/ethyl acetate) provided 141 mg (74%) of 1,4:3,6-dianhydro-2-deoxy-2-methylidene-D-arabino-hexitol as a colorless solid. $^1$H NMR (400 MHz; CDCl$_3$): 5.37 (m, 1H), 5.20 (m, 1H), 4.80 (m, 1H), 4.54 (m, 2H), 4.43 (m, 1H), 4.26 (m, 1H), 3.95 (dd, 1H), 3.54 (dd, 1H), 2.70 (d, 1H).

1,4:3,6-dianhydro-2-deoxy-2-methylidene-5-O-(methylsulfonyl)-D-arabino-hexitol: To a solution of 1,4:3,6-dianhydro-2-deoxy-2-methylidene-D-arabino-hexitol (135 mg, 0.95 mmol) and triethylamine (288 mg, 2.85 mmol) in dichloromethane (10 mL) was added methanesulfonyl chloride (222 mg, 1.94 mmol) at 0° C. under nitrogen. The solution was warmed to room temperature and stirred for 18 h. Dichloromethane (50 mL) was added and the organic layer was washed with saturated aqueous sodium bicarbonate (2×25 mL), water (25 mL) and brine (25 mL) then dried over anhydrous sodium sulfate. Filtration and concentration provided 213 mg (72%) of 1,4:3,6-dianhydro-2-deoxy-2-methylidene-5-O-(methylsulfonyl)-D-arabino-hexitol as a yellow oil. $^1$H NMR (400 MHz; CDCl$_3$): 5.40 (m, 1H), 5.23 (m, 1H), 5.04 (m, 1H), 4.85 (m, 1H), 4.73 (t, 1H), 4.58 (m, 1H), 4.41 (m, 1H), 4.08 (dd, 1H), 3.86 (dd, 1H), 3.14 (s, 3H).

Example 20

1,4:3,6-dianhydro-2-deoxy-5-O-(phenylcarbonyl)-L-arabino-hex-4-enitol: To a mixture of 1,4:3,6-dianhydro-5-O-(phenylcarbonyl)-(D)-glycitol (4.32 g, 17.3 mmol), triethylamine (4.91 mL, 35.3 mmol) and 4-dimethylaminopyridine (0.63 g, 5.2 mmol) in dichloromethane (50 mL) at −10° to −15° was added trifluromethanesulfonic anhydride (3.48 mL, 20.7 mmol) dropwise over ten minutes and the resulting mixture was stirred at this temperature for 3 hours. The mixture was poured into 100 mL of ice-water and extracted with dichloromethane (3×50 mL). The combined organic layers were washed with brine, dried over anhydrous sodium sulfate, filtered then concentrated. The crude triflate was suspended in toluene (50 mL) followed by addition of 1,8-diazabicyclo[4,5,0]undec-7-ene (5.25 mL, 34.6 mmol) and the mixture was stirred at room temperature for 18 hours. The reaction mixture was poured into ice-water and partitioned then the aqueous portion was extracted with dichloromethane (3×50 mL). The combined organic portion was washed with brine, dried over anhydrous sodium sulfate, filtered and concentrated. The residue was purified by flashed chromatography (silica gel, 5-20% ethyl acetate-hexane) to give 1,4:3,6-dianhydro-2-deoxy-5-O-(phenylcarbonyl)-L-arabino-hex-1-enitol, as a white solid, 3.10 g, 77% yield. $^1$H NMR (400 MHz; CDCl$_3$): 8.08-8.06 (m, 2H), 7.61-7.57 (m, 1H), 7.56-7.43 (m, 2H), 6.62-6.61 (d, 1H), 5.48-5.46 (m,1H), 5.32-5.26 (m,1H), 5.13-5.10 (m, 2H), 4.18-4.14 (tr,1H), 3.61-3.56 (tr, 1H).

Example 21

Methyl 3,6-anhydro-5-O-(phenylcarbonyl)-β-L-glucofuranoside: To a solution of 1,4:3,6-dianhydro-2-deoxy-5-O-(phenylcarbonyl)-L-arabino-hex-1-enitol (1.00 g, 4.3 mmol) in methanol (17 mL) at −4° C. was added 3-chloroperoxybenzoic acid (85%, 1.35 g, 8.6 mmol), and the resulting mixture was slowly warmed to room temperature and stirred for 18 hours. The reaction mixture was concentrated, diluted with dichloromethane (50 mL), washed with saturated aqueous sodium bicarbonate solution, dried over sodium sulfate, filtered and concentrated. The residue was purified by flash chromatography (silica gel, 25-60% ethyl acetate-hexane) to give methyl 3,6-anhydro-5-O-(phenylcarbonyl)-β-L-glucofuranoside as a white solid, 1.03 g, 83% yield. $^1$H NMR (400 MHz; CDCl$_3$): 8.11-8.08 (d, 2H), 7.61-7.56 (tr, 1H), 7.48-7.44 (m, 2H), 5.24-5.17 (m, 2H), 4.96 (s, 1H), 4.57-4.56 (d, 1H), 4.27 (s, 1H), 4.22-4.18 (dd, 1H), 4.08-4.04 (dd, 1H), 3.36 (s, 3H).

Methyl 3,6-anhydro-2-O-methyl-5-O-(phenylcarbonyl)-β-L-glucofuranoside: A mixture of methyl 3,6-anhydro-5-O-(phenylcarbonyl)-β-L-glucofuranoside (1.03 g, 3.7 mmol), silver (I) oxide (0.85 g, 3.7 mmol) and methyl iodide (0.34 mL, 5.5 mmol) in DMF (2 mL) was heated at 60° C. for 1 hour. After cooling to room temperature the reaction mixture was diluted with ethyl acetate (50 mL), filtered over celite, adsorbed on silica gel (10 g) and purified by flash chromatography (silica gel, 5-30% ethyl acetate-hexane) to give methyl 3,6-anhydro-2-O-methyl-5-O-(phenylcarbonyl)-β-L-glucofuranoside as a colorless oil, 0.82 g, 76% yield. $^1$H NMR (400 MHz; CDCl$_3$): 8.11-8.09 (d, 2H), 7.60-7.56 (m, 1H), 7.46-7.44 (m, 2H), 5.24-5.20 (m, 1H), 5.18-5.09 (tr, 1H), 4.99 (s, 1H), 4.61-4.60 (d, 1H), 4.21-4.17 (tr, 1H), 4.08-4.03 (tr, 1H), 3.81 (s, 1H), 3.40 (s, 3H), 3.57 (s, 3H).

Methyl 3,6-anhydro-2-O-methyl-α-D-idofuranoside: A solution of methyl 3,6-anhydro-2-O-methyl-5-O-(phenylcarbonyl)-β-L-glucofuranoside (820 mg, 3.1 mmol) and 50% sodium hydroxide (248 mg, 3.1 mmol) in methanol (10 mL) was stirred at room temperature for 30 minutes. The material was adsorbed on silica gel (5 g) and passed through a short column (15% ethyl acetate in hexanes to 5% methanol in ethyl acetate) to give methyl 3,6-anhydro-2-O-methyl-α-D-idofuranoside as a colorless oil, 420 mg, 85% yield. $^1$H NMR (400 MHz; CDCl$_3$): 5.04 (s, 1H), 5.84-5.81 (tr, 1H), 4.44-4.42 (tr, 1H), 4.25-4.19 (m, 1H), 3.85-3.75 (m, 1H), 3.49 (s, 3H), 3.43 (s, 3H), 2.75-2.72 (d, 1H).

Methyl 3,6-anhydro-2-O-methyl-5-O-(methylsulfonyl)-β-L-glucofuranoside: Methyl 3,6-anhydro-2-O-methyl-α-D-idofuranoside (420 mg, 2.6 mmol) was dissolved in dichloromethane (10 mL) and pyridine (0.36 mL, 3.7 mmol) at 0° C. Methanesulfonyl chloride (0.14 mL, 3.1 mmol) was added and the resulting mixture was stirred at 0° C. for 1 hour then at room temperature for 2 hours. The reaction mixture was washed with water and saturated aqueous sodium bicarbonate solution, dried over anhydrous sodium sulfate, filtered and concentrated to give methyl 3,6-anhydro-2-O-methyl-5-O-

(methylsulfonyl)-β-L-glucofuranoside as a colorless oil, 669 mg, 95% yield, which was used without further purification.

Example 22

3,6-anhydro-5-O-(phenylcarbonyl)-α-L-glucofuranose: A mixture of osmium tetroxide (4% in water, 0.25 mL, 0.03 mmol) and N-methylmorpholine (505 mg, 4.3 mmol) in 3 mL of 50% acetone in water was warmed to 60° C. A solution of 1,4:3,6-dianhydro-2-deoxy-5-O-(phenylcarbonyl)-L-arabino-hex-1-enitol (2.00 g, 8.6 mmol) in 6 mL of 50% acetone in water was added over 3 hours. During this time an additional amount of N-methylmorpholine (1.01 g, 8.6 mmol) was added in small portions periodically. Upon completion of the addition process the reaction was stirred for another hour and cooled to room temperature. The crude mixture was applied to a column of silica gel and flashed (0-6% methanol in 1:1 ethyl acetate:hexane) to give 3,6-anhydro-5-O-(phenylcarbonyl)-α-L-glucofuranose as a white solid, 1.5 g, 65% yield. $^1$H NMR (400 MHz; DMSO-$d_6$): 8.01-7.95, (m, 2H), 7.68-7.66 (m, 1H), 7.57-7.53 (m, 2H), 5.18-5.11 (m, 2H), 4.85-4.81 (m, 1H, m), 4.37-4.35 (m, 1H), 4.05-3.96 (m, 2H), 3.85-3.83 (m, 1H).

3,6-anhydro-2-O-methyl-5-O-(phenylcarbonyl)-α-L-glucofuranoside: 3,6-Anhydro-5-O-(phenylcarbonyl)-α-L-glucofuranose (576 mg, 2.2 mmol) was added to a mixture of sodium hydride (60% oil dispersion, 346 mg, 8.7 mmol) and methyl iodide (0.54 mL, 8.7 mmol) in 5 mL of DMF at 0° C. and the resulting mixture was stirred for 1 hour. The reaction mixture was diluted with ethyl acetate and quenched with water (5 mL). The aqueous portion was extracted with ethyl acetate (3×5 mL). The combined organic portion was washed with brine, dried over anhydrous sodium sulfate, filtered, and concentrated. The residue was purified by flashed chromatography (silica gel, 5-20% ethyl acetate in hexane) to give 3,6-anhydro-2-O-methyl-5-O-(phenylcarbonyl)-α-L-glucofuranoside as a white solid, 270 mg, 42% yield. $^1$H NMR (400 MHz; CDCl$_3$): 8.09-8.07 (m, 2H), 7.61-7.57 (m, 1H), 7.48-7.27 (m, 2H), 5.25-5.22 (m, 1H), 5.07-5.06 (d, 1H), 4.94-4.91 (m, 1H), 4.73-4.71 (m, 1H), 4.20-4.16 (m, 1H), 3.96-3.94 (m, 1H), 3.85-3.83 (tr, 1H), 3.50 (s, 3H), 3.42 (s, 3H).

Methyl 3,6-anhydro-2-O-methyl-5-O-(methylsulfonyl)-α-L-glucofuranoside: A solution of methyl 3,6-anhydro-2-O-methyl-5-O-(phenylcarbonyl)-α-L-glucofuranoside (230 mg, 0.92 mmol) and 50% sodium hydroxide (74 mg, 0.92 mmol) in methanol (5 mL) was stirred at room temperature for 30 minutes. The mixture was adsorbed on silica gel (2 g) and passed through a short column (15% ethyl acetate in hexanes to 5% methanol in ethyl acetate) to afford a colorless oil which was employed directly in the next step, 140 mg, 0.72 mmol, 95% yield. The alcohol was dissolved in dichloromethane (5 mL) and pyridine (121 μL, 1.03 mmol) was added at 0° C. Methanesulfonyl chloride (27 μL, 0.88 mmol) was added and the resulting mixture was stirred at 0° C. for 1 hour then at room temperature for 2 hours. The reaction mixture was washed with water and saturated aqueous sodium bicarbonate solution, dried over sodium sulfate, filtered and concentrated to give methyl 3,6-anhydro-2-O-methyl-5-O-(methylsulfonyl)-α-L-glucofuranoside as a colorless oil, 190 mg, 96% yield.

Example 23

3,6-Anhydro-1,2-O-(1-methylethylidene)-5-O-(phenylcarbonyl)-α-L-gluco-furanose: A mixture of 3,6-anhydro-5-O-(phenylcarbonyl)-α-L-glucofuranose (1.00 g), 2,2-dimethoxy propane (0.63 mL), p-toluenesulfonic acid (20 mg) and benzene (10 mL) was heated at reflux for 3 hours. The reaction mixture was cooled then adsorbed on silica gel (10 g) and purified by flash chromatography (silica gel, 5-35% ethyl acetate in hexanes) to give 3,6-anhydro-1,2-O-(1-methylethylidene)-5-O-(phenylcarbonyl)-α-L-glucofuranose as colorless oil, 0.85 g, 74% yield. $^1$H NMR (400 MHz; CDCl$_3$): 8.08-8.06 (d, 2H), 7.59-7.56 (tr, 1H), 7.46-7.42 (m, 2H), 5.99-5.98 (d, 1H), 5.35-5.31 (tr, 1H), 5.10-5.08 (d, 1H), 4.66-4.65 (d, 1H), 4.61-4.60 (d, 1H), 4.20-4.16 (dd, 1H), 3.91-3.74 (tr, 1H,), 1.50 (s, 3H), 1.34 (s, 3H).

3,6-Anhydro-1,2-O-(1-methylethylidene)-5-O-(methylsulfonyl)-α-L-glucofuranose: A solution of 3,6-anhydro-1,2-O-(1-methylethylidene)-5-O-(phenylcarbonyl)-α-L-glucofuranose (850 mg) and 50% sodium hydroxide (111 mg) in methanol (10mL) was stirred at room temperature for 30 minutes. The mixture was then adsorbed on silica gel (5 g) and passed through a short column (15% ethyl acetate in hexanes to 5% methanol in ethyl acetate) and the alcohol intermediate, 390 mg, 70% yield, was used immediately in the next step. The alcohol was dissolved in dichloromethane (10 mL) and pyridine (0.32 mL) at 0° C. Methanesulfonyl chloride (0.12 mL) was added and the resulting mixture was stirred at 0° C. for 1 hour then at room temperature for 2 hours. The reaction mixture was washed with water and saturated aqueous sodium bicarbonate solution, dried over anhydrous sodium sulfate, filtered and concentrated to give 3,6-anhydro-1,2-O-(1-methylethylidene)-5-O-(methylsulfonyl)-α-L-glucofuranose as a colorless oil, 485 mg, 90% yield, which was immediately employed in the next step.

Example 24

(3S,8aS)-3-(Chloromethyl)hexahydro-1H-pyrrolo[2,1-c][1,4]oxazine: (S)-(+)-Prolinol (6.00 g, 59.3 mmol) was added to epichlorohydrin (47 mL, 600 mmol) at 0° C. The solution was stirred at 40° C. for 0.5 h and then concentrated in vacuo. The residual oil was cooled in an ice bath and concentrated sulfuric acid (18 mL) was added dropwise with stirring. The mixture was heated at 170-180° C. for 1.5 h, poured into ice (300 mL) and then basified with sodium carbonate to pH~8. The mixture was partitioned with ethyl acetate/hexanes and filtered. The filtrate was separated and the aqueous portion was extracted twice with ethyl acetate. The combined organic portion was dried over sodium sulfate, filtered and concentrated in vacuo to afford oil that was purified by column chromatography (ethyl acetate for less polar product and then 30% methanol in ethyl acetate). (3S,8aS)-3-(Chloromethyl) hexahydro-1H-pyrrolo[2,1-c][1,4]oxazine (less polar product) (1.87 g, 10.7 mmol, 18% yield): $^1$H NMR (400 MHz, CDCl$_3$): 4.06 (dd, 1H), 3.79-3.71 (m, 1H), 3.60-3.48 (m, 2H), 3.36 (dd, 1H), 3.15 (dd, 1H), 3.13-3.06 (m, 1H), 2.21-2.01 (m, 3H), 1.90-1.68 (m, 3H), 1.39-1.24 (m, 1H); MS (EI) for C$_8$H$_{14}$NOCl: 176 (MH$^+$). (3R,8aS)-3-(Chloromethyl) hexahydro-1H-pyrrolo[2,1-c][1,4]oxazine (1.54 g, 8.77 mmol, 15% yield): $^1$H NMR (400 MHz, CDCl$_3$): 3.94-3.77 (m, 4H), 3.55 (dd, 1H), 3.02-2.93 (m, 2H), 2.45 (dd, 1H), 2.29-2.15 (m, 2H), 1.88-1.64 (m, 3H), 1.49-1.38 (m, 1H); MS (EI) for C$_8$H$_{14}$NOCl: 176 (MH$^+$).

Using the same or analogous synthetic techniques and/or substituting with alternative starting materials, the following were prepared:

(3R,8aR)-3-(Chloromethyl)hexahydro-1H-pyrrolo[2,1-c][1,4]oxazine: $^1$H NMR (400 MHz, CDCl$_3$): 4.05 (dd, 1H), 3.79-3.70 (m, 1H), 3.61-3.48 (m, 2H), 3.35 (dd, 1H), 3.15 (dd, 1H), 3.13-3.07 (m, 1H), 2.21-2.01 (m, 3H), 1.89-1.67 (m, 3H), 1.39-1.25 (m, 1H); MS (EI) for C$_8$H$_{14}$NOCl: 176 (MH$^+$).

(3S,8aR)-3-(Chloromethyl)hexahydro-1H-pyrrolo[2,1-c]
[1,4]oxazine: $^1$H NMR (400 MHz, CDCl$_3$): 3.93-3.77 (m,
4H), 3.55 (dd, 1H), 3.02-2.93 (m, 2H), 2.45 (dd, 1H), 2.30-
2.15 (m, 2H), 1.88-1.64 (m, 3H), 1.49-1.37 (m, 1H); MS (EI)
for C$_8$H$_{14}$NOCl: 176 (MH$^+$).

Example 25

(3S,8aS)-Hexahydro-1H-pyrrolo[2,1-c][1,4]oxazin-3-yl-
methyl acetate: (3S,8aS)-3-(Chloromethyl)hexahydro-1H-
pyrrolo[2,1-c][1,4]oxazine (2.30 g, 13.1 mmol) and potas-
sium acetate (12.8 g, 131 mmol) were stirred in
dimethylformamide (25 mL) at 140° C. for 20 h. The mixture
was partitioned between ethyl acetate and water. The organic
portion was washed twice with water, then with brine, dried
over sodium sulfate, filtered and concentrated in vacuo to
afford (3S,8aS)-hexahydro-1H-pyrrolo[2,1-c][1,4]oxazin-3-
ylmethyl acetate as a brown oil (2.53 g, 12.7 mmol, 97%
yield). $^1$H NMR (400 MHz, CDCl$_3$): 4.14-4.02 (m, 3H),
3.81-3.72 (m, 1H), 3.37-3.31 (m, 1H), 3.09 (dt, 1H), 3.00 (dd,
1H), 2.21-2.00 (m, 3H), 2.10 (s, 3H), 1.90-1.67 (m, 3H),
1.39-1.24 (m, 1H); MS (EI) for C$_{10}$H$_{17}$NO$_3$: 200 (MH$^+$).

(3S,8aS)-Hexahydro-1H-pyrrolo[2,1-c][1,4]oxazin-3-yl-
methanol: (3S,8aS)-Hexahydro-1H-pyrrolo[2,1-c][1,4]ox-
azin-3-ylmethyl acetate (2.36 g, 11.9 mmol) was treated with
sodium methoxide (25 wt % solution in methanol; 2.7 mL) for
0.5 h. The mixture was cooled in an ice bath and a solution of
4M HCl in 1,4-dioxane (3 mL, 12.0 mmol) was added slowly.
The mixture was stirred at room temperature for 5 minutes
and then was concentrated in vacuo to afford a suspension
which was diluted with dichloromethane, filtered and the
filtrate was concentrated in vacuo to afford (3S,8aS)-hexahy-
dro-1H-pyrrolo[2,1-c][1,4]oxazin-3-ylmethanol as a brown
oil (1.93 g, >100% yield). $^1$H NMR (400 MHz, CDCl$_3$): 4.05
(dd, 1H), 3.73-3.65 (m, 2H), 3.62-3.56 (m, 1H), 3.39-3.34 (m,
1H), 3.10 (dt, 1H), 3.00-2.95 (m, 1H), 2.24-1.98 (m, 4H),
1.97-1.70 (m, 3H), 1.44-1.28 (m, 1H); MS (EI) for
C$_8$H$_{15}$NO$_2$: 158 (MH$^+$).

(3S,8aS)-hexahydro-1H-pyrrolo[2,1-c][1,4]oxazin-3-yl-
methyl methanesulfonate: (3S,8aS)-Hexahydro-1H-pyrrolo
[2,1-c][1,4]oxazin-3-ylmethanol (1.00 g, 6.37 mmol) was
dissolved in dichloromethane (10 mL) and triethylamine (2.4
mL, 17.3 mmol) was added at 0° C. followed by dropwise
addition of methanesulfonyl chloride (0.93 mL, 12.0 mmol).
The solution was warmed to room temperature and stirred for
1.25 h and then was concentrated in vacuo. The residue was
partitioned between ethyl acetate and saturated sodium bicar-
bonate solution. The organic portion was washed with satu-
rated sodium bicarbonate solution. The combined aqueous
portion was extracted with ethyl acetate. The combined
organic portion was washed with brine, dried over sodium
sulfate, filtered and concentrated in vacuo to afford (3S,8aS)-
hexahydro-1H-pyrrolo[2,1-c][1,4]oxazin-3-ylmethyl meth-
anesulfonate as an orange-brown oil (1.20 g, 5.1 mmol, 80%
yield). MS (EI) for C$_9$H$_{17}$NO$_4$S: 236 (MH$^+$).

Example 26

Octahydro-2H-quinolizin-3-ylmethanol: Ethyl octahydro-
2H-quinolizine-3-carboxylate (2.35 g, 11.1 mmol) was added
dropwise to a stirred suspension of lithium aluminum hydride
(1 M solution in tetrahydrofuran, 33 mL, 33 mmol) in tetrahy-
drofuran (50 mL) at 0° C. The reaction was stirred at room
temperature for 3 h. The mixture was cooled in an ice bath and
ethyl acetate (6 mL) was added slowly, followed by water
(1.25 mL), 15% aqueous sodium hydroxide solution (5 mL)
and water (1.25 mL). The mixture was filtered through a pad
of celite and washed with ether. The filtrate was concentrated
in vacuo and dried rigorously to afford octahydro-2H-quino-
lizin-3-ylmethanol as a yellow oil (1.66 g, 9.82 mmol, 88%
yield). MS (EI) for C$_{10}$H$_{19}$NO: 170 (MH$^+$).

Octahydro-2H-quinolizin-3-ylmethyl methanesulfonate:
Octahydro-2H-quinolizin-3-ylmethanol (600 mg, 3.55
mmol) was dissolved in dichloromethane (8 mL) and triethy-
lamine (1.5 mL, 10.8 mmol) was added at 0° C. followed by
dropwise addition of methanesulfonyl chloride (0.56 mL,
7.16 mmol). The solution was warmed to room temperature
and stirred for 1.25 h and then was concentrated in vacuo. The
residue was partitioned between ethyl acetate and saturated
sodium bicarbonate solution. The aqueous portion was
extracted with ethyl acetate. The combined organic portion
was washed with brine, dried over sodium sulfate, filtered and
concentrated in vacuo to afford octahydro-2H-quinolizin-3-
ylmethyl methanesulfonate as an orange oil (796 mg, 3.22
mmol, 91% yield). MS (EI) for C$_{11}$H$_{21}$NO$_3$S: 248 (MH$^+$).

Example 27

(3S,8aS)-3-(Hydroxymethyl)hexahydropyrrolo[1,2-a]
pyrazin-1(2H)-one: A solution of methyl 1-[(2S)-3-hydroxy-
2-({[(phenylmethyl)oxy]carbonyl}amino)propyl]-L-proli-
nate (3.50 g, 10.4 mmol) in methanol was added to 5%
palladium on carbon (50 wt. % in water) in methanol and
treated with hydrogen at 40 psi for 1 h. The mixture was
filtered and the filtrate was brought to reflux briefly and then
cooled and concentrated in vacuo to afford (3S,8aS)-3-(hy-
droxymethyl)hexahydropyrrolo[1,2-a]pyrazin-1(2H)-one as
a colorless solid (1.50 g, 8.83 mmol, 85% yield). $^1$H NMR
(400 MHz, CDCl$_3$): 7.28-7.22 (m, 1H), 3.83-3.75 (m, 1H),
3.69 (dd, 1H), 3.56 (dd, 1H), 3.31 (t, 1H), 3.08 (dd, 1H), 2.92
(dt, 1H), 2.76-2.70 (m, 1H), 2.66 (dd, 1H), 2.28-2.16 (m, 1H),
2.02-1.73 (m, 3H); MS (EI) for C$_8$H$_{14}$N$_2$O$_2$: 171 (MH$^+$).

(3S,8aS)-3-({[(1,1-Dimethylethyl)(dimethyl)silyl]
oxy}methyl)hexahydropyrrolo[1,2-a]pyrazin-1(2B)-one: To
a solution of (3S,8aS)-3-(hydroxymethyl) hexahydropyrrolo
[1,2-a]pyrazin-1(2H)-one (1.49 g, 8.82 mmol) in dimethyl-
formamide (20 mL) was added triethylamine (2.45 mL, 17.6
mmol) and 4-dimethylaminopyridine (90 mg, 0.882 mmol).
The solution was cooled in an ice bath and tert-butyldimeth-
ylsilyl chloride (2.66 g, 17.6 mmol) was added. The mixture
was warmed to room temperature and stirred for 14 h. The
mixture was concentrated in vacuo and the residue was par-
titioned between ethyl acetate and water. The aqueous portion
was extracted twice with ethyl acetate. The combined organic
portion was dried over sodium sulfate, filtered and concen-
trated in vacuo to afford a pale brown solid which was tritu-
rated with ethyl acetate to afford (3S,8aS)-3-({[(1,1-dimeth-
ylethyl)(dimethyl)silyl]oxy}methyl)hexahydropyrrolo[1,2-
a]pyrazin-1(2H)-one as an off-white solid (1.74 g, 5.84
mmol, 66% yield). $^1$H NMR (400 MHz, CDCl$_3$): 6.09-5.90
(m, 1H), 3.86-3.76 (m, 1H), 3.63 (dd, 1H), 3.44 (dd, 1H), 3.25
(t, 1H), 3.10 (ddd, 1H), 2.98-2.90 (m, 1H), 2.68-2.60 (m, 1H),
2.52 (dd, 1H), 2.28-2.18 (m, 1H), 2.06-1.95 (m, 1H), 1.93-
1.74 (m, 2H), 0.90 (s, 9H), 0.07 (s, 6H); MS (EI) for
C$_{14}$H$_{28}$N$_2$O$_2$Si: 285 (MH$^+$).

(3S,8aS)-3-({[(1,1-Dimethylethyl)(dimethyl)silyl]
oxy}methyl)-2-methylhexahydro pyrrolo[1,2-a]pyrazin-1
(2H)-one: (3S,8aS)-3-({[(1,1-Dimethylethyl)(dimethyl)si-
lyl]oxy}methyl)hexahydropyrrolo[1,2-a]pyrazin-1(2H)-one
(1.51 g, 5.32 mmol) in dimethylformamide (8 mL) was added
to an ice-cooled suspension of sodium hydride (60 wt. %
dispersion in oil; 213 mg, 5.32 mmol) in dimethylformamide
(8 mL). The mixture was stirred at 0° C. for 0.25 h and then
iodomethane (0.332 mL, 5.32 mmol) was added dropwise.

The mixture was stirred at room temperature for 0.5 h and then was stirred at 70° C. for 2 h. The mixture was concentrated in vacuo and the residue was partitioned between ethyl acetate and water. The aqueous portion was extracted with ethyl acetate. The combined organic portion was dried over sodium sulfate, filtered and concentrated in vacuo to afford (3S,8aS)-3-({[(1,1-dimethylethyl)(dimethyl)silyl]oxy}methyl)-2-methylhexahydropyrrolo[1,2-a]pyrazin-1(2H)-one as a yellow oil (1.552 g, 5.21 mmol) which was dissolved in tetrahydrofuran (20 mL) and treated with tetrabutylammonium fluoride (1.0M solution in tetrahydrofuran; 10.4 mL, 10.4 mmol) for 2 h at room temperature. The mixture was concentrated in vacuo and purified by column chromatography (10% methanol in dichloromethane) to afford (3S,8aS)-3-(hydroxymethyl)-2-methylhexahydropyrrolo[1,2-a]pyrazin-1(2H)-one as a yellow oil (496 mg, 2.70 mmol, 51% yield from (3S,8aS)-3-({[(1,1-dimethylethyl)(dimethyl)silyl]oxy}methyl)hexahydropyrrolo[1,2-a]pyrazin-1(2H)-one). $^1$H NMR (400 MHz, CDCl$_3$): 3.98-3.93 (m, 1H), 3.86 (dd, 1H), 3.61-3.55 (m, 1H), 3.29-3.25 (m, 1H), 3.09-3.03 (m, 1H), 3.03-2.97 (m, 1H), 3.02 (s, 3H), 2.93 (dd, 1H), 2.87-2.79 (m, 1H), 2.32-2.21 (m, 1H), 2.00-1.86 (m, 2H), 1.83-1.64 (m, 1H); MS (EI) for C$_9$H$_{16}$N$_2$O$_2$: 185 (MH$^+$).

Example 28

1,2-Dideoxy-1-[(2S)-2-(methoxycarbonyl)-1-pyrrolidinyl]-2-[[(phenylmethoxy) carbonyl]amino]-D-glycero-hexitol: To a solution of 2-deoxy-2-{[(phenylmethyloxy) carbonyl]amino}-D-glycero-hexopyranose (5.0 g, 0.016 mol) in methanol (500 mL) was added L-proline methyl ester hydrochloride (2.8 g, 0.022 mol) and sodium cyanoborohydride (3.4 g, 0.054 mol). The solution was heated to 64° C. for 14 h. After cooling to room temperature, the reaction mixture was concentrated in vacuo to afford 1,2-dideoxy-1-[(2S)-2-(methoxycarbonyl)-1-pyrrolidinyl]-2-[[(phenylmethoxy)carbonyl]amino]-D-glycero-hexitol (6.81 g, 100%) as a clear and colorless oil. MS (EI) for C$_{20}$H$_{31}$N$_2$O$_8$: 427 (MH$^+$).

Example 29

Methyl 1-[(2S)-3-hydroxy-2-({[(phenylmethyl)oxy]carbonyl}amino)propyl]-L-prolinate: 1,2-dideoxy-1-[(2S)-2-(methoxycarbonyl)-1-pyrrolidinyl]-2-[[(phenylmethoxy)carbonyl]amino]-D-glycero-hexitol (6.81 g, 0.016 mol) was taken into water (100 mL) and the resulting solution was cooled to 0° C. Sodium periodiate (14.8 g, 0.069 mol) dissolved in water was added dropwise and the resulting mixture was stirred at 0° C. for 2 h. The reaction mixture was partitioned with dichloromethane (3×100 mL), dried over anhydrous magnesium sulfate, filtered and concentrated in vacuo. The residue was taken up in methanol (200 mL) and the resulting solution was cooled to 0° C. Sodium borohydride (1.98 g, 0.052 mol) was added and the reaction mixture was stirred for 1 h at 0° C. The reaction mixture was concentrated in vacuo and partitioned with dichloromethane and saturated aqueous ammonium chloride. The organic layer was dried over anhydrous magnesium sulfate, filtered and concentrated in vacuo. The resulting crude product was purified by column chromatography (5% methanol in dichloromethane) to yield methyl 1-[(2S)-3-hydroxy-2-({[(phenylmethyl)oxy]carbonyl}amino)propyl]-L-prolinate (4.9 g, 92%) as a white solid. MS (EI) for C$_{17}$H$_{25}$N$_2$O$_5$: 337 (MH$^+$).

Methyl 1-[(2S)-3-[(methylsulfonyl)oxy]-2-({[(phenylmethyl)oxy]carbonyl]amino) propyl]-L-prolinate: Methyl 1-[(2S)-3-hydroxy-2-({[(phenylmethyl)oxy]carbonyl}amino) propyl]-L-prolinate (200 mg, 0.594 mmol) was dissolved in dichloromethane (5 mL) followed by the addition of 4-(dimethylamino)pyridine (3.6 mg, 0.039 mmol) and triethylamine (0.125 mL, 0.891 mmol) and the resulting mixture was cooled to 0° C. Methanesulfonyl chloride (0.060 mL, 0.773 mmol) was added dropwise and the reaction mixture was stirred for 1 h at 0° C. The mixture was partitioned between dichloromethane and saturated aqueous sodium bicarbonate. The organic layer was dried over anhydrous magnesium sulfate, filtered and concentrated in vacuo to afford methyl 1-[(2S)-3-[(methylsulfonyl)oxy]-2-({[(phenylmethyl)oxy]carbonyl}amino)propyl]-L-prolinate (246 mg, 100%) as a clear and colorless oil. MS (EI) for C$_{18}$H$_{27}$N$_2$O$_7$S: 415 (MH$^+$).

Example 30

1,1-Dimethylethyl (3aR,6aS)-5-(hydroxymethyl)hexahydrocyclopenta[c]pyrrole-2(1H)-carboxylate: Under a nitrogen atmosphere, borane tetrahydrofuran complex (1M in THF, 42 mL, 41.9 mmol) was diluted with tetrahydrofuran (42 mL) and cooled with an ice bath. Neat 2,3-dimethylbut-2-ene (5.0 mL, 41.9 mmol) was added in portions over 0.25 h and the solution was stirred at 0° C. for 3 h. A solution of 1,1-dimethylethyl (3aR,6aS)-5-methylidenehexahydrocyclopenta[c]pyrrole-2(1H)-carboxylate (1.98 g, 8.88 mmol) in tetrahydrofuran (10 mL) was added slowly, and the solution was warmed to room temperature and stirred 12 h. After cooling to 0° C., 10% aqueous sodium hydroxide (17 mL, 41.7 mmol) was added slowly, followed by 30% aqueous hydrogen peroxide (13 mL, 128 mmol) and the solution was warmed to room temperature. The solvent was removed in vacuo and the solution was partitioned between water and diethyl ether. The layers were separated and the aqueous layer was further extracted (3×50 mL diethyl ether). The combined organic layers were dried over anhydrous sodium sulfate, filtered and concentrated in vacuo to provide 2.04 (95%) of 1,1-dimethylethyl (3aR,6aS)-5-(hydroxymethyl)hexahydrocyclopenta[c]pyrrole-2(1H)-carboxylate, which was used without purification. $^1$H NMR (400 MHz, CDCl$_3$): 8.50 (broad s, 1H), 3.66-3.46 (m, 3H), 3.20-3.00 (m, 2H), 2.70-2.59 (m, 2H), 2.37-2.18 (m, 1H), 2.04 (m, 1H), 1.84 (broad s, 1H), 1.70-1.55 (m, 1H), 1.46 (s, 9H), 1.17 (m, 1H), 0.93 (m, 1H).

1,1-Dimethylethyl (3aR,6aS)-5-{[(methylsulfonyl)oxy]methyl}hexahydrocyclopenta[c]pyrrole-2(1H)-carboxylate: Methanesulfonyl chloride (0.2 mL, 2.48 mmol) was added dropwise to a solution of 1,1-dimethylethyl (3aR,6aS)-5-(hydroxymethyl)hexahydro cyclopenta[c]pyrrole-2(1H)-carboxylate (0.40 g, 1.65 mmol) and triethylamine (0.69 mL, 4.95 mmol) in 20 mL dichloromethane at 0° C. and the reaction mixture was stirred for 1 h at room temperature. The solvent was evaporated, the resulting crude mixture was diluted with 100 mL ethyl acetate and washed with water (30 mL), 1M aqueous sodium hydroxide, brine, 1M aqueous hydrochloric acid and brine again. The organic layer was dried over anhydrous sodium sulfate, filtered and concentrated in vacuo. The resulting 1,1-dimethylethyl (3aR,6aS)-5-{[(methylsulfonyl)oxy]methyl}hexahydrocyclopenta[c]pyrrole-2(1H)-carboxylate was used without further purification. MS (EI) for C$_{14}$H$_{25}$NO$_5$S: 320 (MH$^+$), 264 (M-tBu).

Example 31

1,1-Dimethylethyl (3aR,6aS)-5-(hydroxy)-hexahydrocyclopenta[c]pyrrole-2(1H)-carboxylate: Sodium borohydride (0.15 g, 4.00 mmol), was added to a solution of 1,1-dimethylethyl (3aR,6aS)-5-oxo-hexahydrocyclopenta[c]pyrrole-2 (1H)-carboxylate (0.45 g, 2.00 mmol) in 10 mL methanol at 0° C. and the reaction mixture was stirred for 1 h at this temperature. The solvent was evaporated, the crude mixture was diluted with 100 mL ethyl acetate and washed with water (30 mL), 1M aqueous hydrochloric acid and brine. The organic layer was dried over anhydrous sodium sulfate, filtered and concentrated to give 1,1-dimethylethyl (3aR,6aS)-5-(hydroxy)-hexahydrocyclopenta[c]pyrrole-2(1H)-carboxylate (0.44 g, 98%). $^1$H NMR (400 MHz, d$_6$-DMSO): 4.08 (m, 1H), 3.40 (m, 2H), 3.30 (m, 2H), 2.50 (m, 2H), 1.98 (m, 2H), 1.40 (s, 9H), 1.30 (m, 2H). MS (EI) for C$_{12}$H$_{21}$NO$_3$: 228 (MH$^+$).

1,1-Dimethylethyl (3aR,6aS)-5-{[(methylsulfonyl)oxy]}hexahydrocyclopenta[c]pyrrole-2(1H)-carboxylate: Methanesulfonyl chloride (0.18 mL, 2.33 mmol), was added dropwise to a solution of 1,1-dimethylethyl (3aR,6aS)-5-(hydroxy)-hexahydrocyclopenta[c]pyrrole-2(1H)-carboxylate (0.44 g, 1.94 mmol) and triethylamine (0.81 mL, 5.81 mmol) in 10 mL dichloromethane at 0° C. and the reaction mixture was stirred for 1 h at room temperature. The solvent was evaporated, the resulting crude mixture was diluted with 100 mL ethyl acetate and washed with water (30 mL), brine, 1M aqueous hydrochloric acid and brine again. The organic layer was dried over anhydrous sodium sulfate, filtered and concentrated. The resulting crude 1,1-dimethylethyl (3aR,6aS)-5-{[(methylsulfonyl)oxy]}hexahydrocyclopenta[c]pyrrole-2(1H)-carboxylate was used without further purification. MS (EI) for C$_{13}$H$_{23}$NO$_5$S: 306 (MH$^+$).

Example 32

3-(Chloromethyl)hexahydro-1H-[1,4]oxazino[3,4-c][1,4]oxazine: A solution of (3R)-morpholin-3-ylmethanol (4.21 g, 36.0 mmol) in 2-(chloromethyl)oxirane (28.2 mL, 0.360 mol) was heated to 40° C. for 3 h and then the solution was concentrated in vacuo. The intermediate was cooled in an ice bath and treated with 30.0 mL of concentrated sulfuric acid. The mixture was heated to 170° C. for 2 h and then allowed to cool to room temperature. The mixture was poured into ice-water and solid sodium bicarbonate was carefully added until the solution was basic. 10% methanol in ethyl acetate was added and the biphasic mixture was filtered. The layers were separated and the aqueous layer was extracted (3×100 mL 10% methanol in ethyl acetate). The combined organic layers were dried over anhydrous sodium sulfate, filtered and concentrated in vacuo. Column chromatography (SiO$_2$, 2:5 hexanes:ethyl acetate) provided 3-(chloromethyl)hexahydro-1H-[1,4]oxazino[3,4-c][1,4]oxazine 2.44 g (35%) as two separated diastereomers. (3R,9aS)-3-(chloromethyl)hexahydro-1H-[1,4]oxazino[3,4-c][1,4]oxazine: (0.886 g, 13% yield): $^1$H NMR (400 MHz, CDCl$_3$): 3.91 (m, 3H), 3.82 (m, 1H), 3.68 (dt, 1H), 3.61 (dd, 1H), 3.47 (dd, 1H), 3.35 (t, 1H), 3.19 (t, 1H), 2.80 (d, 1H), 2.54 (m, 2H), 2.40 (m, 2H); MS (EI) for C$_8$H$_{14}$NO$_2$Cl: 192 (MH$^+$). (3S,9aS)-3-(chloromethyl)hexahydro-1H-[1,4]oxazino[3,4-c][1,4]oxazine: (1.55 g, 22% yield): $^1$H NMR (400 MHz, CDCl$_3$): 3.85 (m, 2H), 3.73 (m, 3H), 3.50 (m, 2H), 3.29 (t, 1H), 3.18 (t, 1H), 2.85 (dd, 1H), 2.64 (dd, 1H), 2.40 (m, 2H), 2.17 (t, 1H); MS (EI) for C$_8$H$_{14}$NO$_2$Cl: 192 (MH$^+$).

Hexahydro-1H-[1,4]oxazino[3,4-c][1,4]oxazin-3-ylmethyl acetate: A suspension of (3R,9aS)-3-(chloromethyl)hexahydro-1H-[1,4]oxazino[3,4-c][1,4]oxazine (1.97 g, 10.3 mmol) and potassium acetate (10.1 g, 102 mmol) in DMF (20.0 mL) was stirred at 140° C. for 16 h, and then at 150° C. for another 12 h. The reaction mixture was partitioned between water (250 mL) and ethyl acetate (250 mL), the organic layer was washed with 5% lithium chloride (2×100 mL) and brine (100 mL) then dried over anhydrous sodium sulfate and concentrated in vacuo. Column chromatography (SiO$_2$, 1:1 hexane:ethyl acetate, then 100% ethyl acetate) afforded 0.92 g (42%) of hexahydro-1H-[1,4]oxazino[3,4-c][1,4]oxazin-3-ylmethyl acetate as a yellow oil. Distinct diastereomers as described above were converted in this step to give: (3R,9aS)-hexahydro-1H-[1,4]oxazino[3,4-c][1,4]oxazin-3-ylmethyl acetate: $^1$H NMR (400 MHz, CDCl$_3$): 4.18 (dd, 1H), 4.00 (m, 1H), 3.80 (dd, 1H), 3.68 (dt, 1H), 3.60 (dd, 1H), 3.46 (m, 2H), 3.22 (t, 1H), 2.64 (dd, 1H), 2.53 (m, 2H), 2.43-2.35 (m, 2H), 2.10 (s, 3H), and (3S,9aS)-hexahydro-1H-[1,4]oxazino[3,4-c][1,4]oxazin-3-ylmethyl acetate: $^1$H NMR (400 MHz, CDCl$_3$): 4.09 (d, 2H), 3.90-3.82 (m, 2H), 3.75-3.64 (m, 3H), 3.27 (t, 1H), 3.18 (t, 1H), 2.69 (dd, 1H), 2.63 (m, 1H), 2.46-2.33 (m, 2H), 2.16 (t, 1H), 2.10 (s, 3H).

(3R,9aS)-Hexahydro-1H-[1,4]oxazino[3,4-c][1,4]oxazin-3-ylmethyl methanesulfonate: To a solution of (3R,9aS)-hexahydro-1H-[1,4]oxazino[3,4-c][1,4]oxazin-3-ylmethyl acetate (0.922 g, 4.28 mmol) in methanol (14.0 mL) was added 1.03 mL (4.50 mmol) of sodium methoxide (25% wt. in methanol) dropwise at room temperature. After 5 min., 1.6 mL (6.43 mmol) of 4.0M hydrogen chloride in dioxane was added and a pink precipitate formed. The solution was concentrated in vacuo and the pink solid was taken up in 30.0 mL dichloromethane. This slurry was cooled in an ice bath and triethylamine (3.0 mL, 21.5 mmol) was added, followed by methanesulfonyl chloride (0.37 mL, 4.71 mmol). The resultant yellow solution was stirred for 30 minutes at room temperature. The mixture was then partitioned between dichloromethane and saturated aqueous sodium bicarbonate then the aqueous layer was extracted (3×50 mL dichloromethane). The combined organic layers were dried over anhydrous sodium sulfate, filtered and concentrated in vacuo to provide crude (3R,9aS)-hexahydro-1H-[1,4]oxazino[3,4-c][1,4]oxazin-3-ylmethyl methanesulfonate which was taken on to the following reaction without purification.

Example 33

(8aR)-6-(Chloromethyl)tetrahydro-1H-[1,3]thiazolo[4,3-c][1,4]oxazine: A solution of (4R)-1,3-thiazolidin-4-ylmethanol (0.300 g, 2.52 mmol) in 2-(chloromethyl)oxirane (2.0 mL, 25.5 mmol) was heated under nitrogen to 40° C. for 12 h. The solution was then cooled to room temperature and 2-(chloromethyl)oxirane was removed in vacuo. The crude intermediate was cooled in ice, and was taken up in 2.0 mL of concentrated sulfuric acid. The resulting mixture was heated to 200° C. for 0.5 h then poured carefully onto wet ice, which was allowed to melt. The aqueous solution was carefully made basic using solid sodium bicarbonate and the resulting mixture was filtered using water and 10% methanol in ethyl acetate as eluent. The layers were separated and the aqueous layer was extracted with 10% methanol in ethyl acetate. The combined organic layers were dried over anhydrous sodium sulfate, filtered, and concentrated in vacuo to give 11.6 mg (2.4% yield) of crude (8aR)-6-(chloromethyl)tetrahydro-1H-[1,3]thiazolo[4,3-c][1,4]oxazine as a mixture of diastereomers which was directly taken on to the next step.

Example 34

1,1-Dimethylethyl (3-endo)-3-{2-[(methylsulfonyl)oxy]ethyl}-8-azabicyclo[3.2.1]octane-8-carboxylate: To a solution of 1,1-dimethylethyl (3-endo)-3-(2-hydroxyethyl)-8-azabicyclo[3.2.1]octane-8-carboxylate (30.3 mg, 1.19 mmol) in dichloromethane (4.0 mL), was added triethylamine (0.5 mL, 3.56 mmol) and the solution was cooled to 0° C. under nitrogen. Methanesulfonyl chloride (0.11 mL, 1.42 mmol) was added slowly and mixture was allowed to warm to room temperature and stirred for 1 h. The reaction mixture was partitioned between dichloromethane and water. The aqueous phase was extracted with dichloromethane (2×100 mL). The combined organic layers were dried over anhydrous sodium sulfate, filtered and concentrated in vacuo to provide 35.1 mg (89%) of 1,1-dimethylethyl (3-endo)-3-{2-[(methylsulfonyl) oxy]ethyl}-8-azabicyclo[3.2.1]octane-8-carboxylate, which was carried forward for alkylation without purification.

Assays

Kinase assays were performed by measurement of incorporation of $\gamma$-$^{33}$P ATP into immobilized myelin basic protein (MBP). High binding white 384 well plates (Greiner) were coated with MBP (Sigma #M-1891) by incubation of 60 ul/well of 20 μg/ml MBP in Tris-buffered saline (TBS; 50 mM Tris pH 8.0, 138 mM NaCl, 2.7 mM KCl) for 24 hours at 4° C. Plates were washed 3× with 100 μl TBS. Kinase reactions were carried out in a total volume of 34 μl in kinase buffer (5 mM Hepes pH 7.6, 15 mM NaCl, 0.01% bovine gamma globulin (Sigma #I-5506), 10 mM MgCl$_2$, 1 mM DTT, 0.02% TritonX-100). Compound dilutions were performed in DMSO and added to assay wells to a final DMSO concentration of 1%. Each data point was measured in duplicate, and at least two duplicate assays were performed for each individual compound determination. Enzyme was added to final concentrations of 10 nM or 20 nM, for example. A mixture of unlabeled ATP and $\gamma$-$^{33}$P ATP was added to start the reaction (2×10$^6$ cpm of $\gamma$-$^{33}$P ATP per well (3000 Ci/mmole) and either 10 μM or 30 μM unlabeled ATP, typically. The reactions were carried out for 1 hour at room temperature with shaking. Plates were washed 7× with TBS, followed by the addition of 50 μl/well scintillation fluid (Wallac). Plates were read using a Wallac Trilux counter. This is only one format of such assays, various other formats are possible, as known to one skilled in the art.

The above assay procedure can be used to determine the IC$_{50}$ for inhibition and/or the inhibition constant, K$_i$. The IC$_{50}$ is defined as the concentration of compound required to reduce the enzyme activity by 50% under the conditions of the assay. Exemplary compositions have IC$_{50}$'s of, for example, less than about 100 μM, less than about 10 μM, less than about 1 μM, and further for example having IC$_{50}$'s of less than about 100 nM, and still further, for example, less than about 10 nM. The K$_i$ for a compound may be determined from the IC$_{50}$ based on three assumptions. First, only one compound molecule binds to the enzyme and there is no cooperativity. Second, the concentrations of active enzyme and the compound tested are known (i.e., there are no significant amounts of impurities or inactive forms in the preparations). Third, the enzymatic rate of the enzyme-inhibitor complex is zero. The rate (i.e., compound concentration) data are fitted to the equation:

$$V = V_{max}E_0\left[1 - \frac{(E_0 + I_0 + K_d) - \sqrt{(E_0 + I_0 + K_d)^2 - 4E_0 I_0}}{2E_0}\right]$$

where V is the observed rate, V$_{max}$, is the rate of the free enzyme, I$_0$ is the inhibitor concentration, E$_0$ is the enzyme concentration, and K$_d$ is the dissociation constant of the enzyme-inhibitor complex.

Kinase Specificity Assays:

Kinase activity and compound inhibition are investigated using one or more of the three assay formats described below. The ATP concentrations for each assay are selected to be close to the Michaelis-Menten constant (K$_M$) for each individual kinase. Dose-response experiments are performed at 10 different inhibitor concentrations in a 384-well plate format. The data are fitted to the following four-parameter equation:

$$Y = Min+(Max-Min)/(1+(X/IC_{50})^H)$$

where Y is the observed signal, X is the inhibitor concentration, Min is the background signal in the absence of enzyme (0% enzyme activity), Max is the signal in the absence of inhibitor (100% enzyme activity), IC$_{50}$ is the inhibitor concentration at 50% enzyme inhibition and H represents the empirical Hill's slope to measure the cooperativity. Typically H is close to unity.

c-Met Assay c-Met biochemical activity was assessed using a Luciferase-Coupled Chemiluminescent Kinase assay (LCCA) format as described above. Again, kinase activity was measured as the percent ATP remaining following the kinase reaction. Remaining ATP was detected by luciferase-luciferin-coupled chemiluminescence. Specifically, the reaction was initiated by mixing test compounds, 1 μM ATP, 1 μM poly-EY and 10 nM c-Met (baculovirus expressed human c-Met kinase domain P948-S1343) in a 20 uL assay buffer (20 mM Tris-HCL pH7.5, 10 mM MgCl$_2$, 0.02% Triton X-100, 100 mM DTT, 2 mM MnCl$_2$). The mixture is incubated at ambient temperature for 2 hours after which 20 uL luciferase-luciferin mix is added and the chemiluminescent signal read using a Wallac Victor$^2$ reader. The luciferase-luciferin mix consists of 50 mM HEPES, pH 7.8, 8.5 ug/mL oxalic acid (pH 7.8), 5 (or 50) mM DTT, 0.4% Triton X-100, 0.25 mg/mL coenzyme A, 63 uM AMP, 28 ug/mL luciferin and 40,000 units of light/mL luciferase.

KDR Assay

KDR biochemical activity was assessed using a Luciferase-Coupled Chemiluminescent Kinase assay (LCCA) format. Kinase activity was measured as the percent ATP remaining following the kinase reaction. Remaining ATP was detected by luciferase-luciferin-coupled chemiluminescence. Specifically, the reaction was initiated by mixing test compounds, 3 μM ATP, 1.6 μM poly-EY and 5 nM KDR (baculovirus expressed human KDR kinase domain D807-V1356) in a 20 uL assay buffer (20 mM Tris-HCL pH7.5, 10 mM MgCl$_2$, 0.01% Triton X-100, 1 mM DTT, 3 mM MnCl$_2$). The mixture is incubated at ambient temperature for 4 hours after which 20 uL luciferase-luciferin mix is added and the chemiluminescent signal read using a Wallac Victor$^2$ reader. The luciferase-luciferin mix consists of 50 mM HEPES, pH 7.8, 8.5 ug/mL oxalic acid (pH 7.8), 5 (or 50) mM DTT, 0.4% Triton X-100, 0.25 mg/mL coenzyme A, 63 uM AMP, 28 ug/mL luciferin and 40,000 units of light/mL luciferase.

flt-3 Assay

Biochemical activity for flt-3 was assessed using a Luciferase-Coupled Chemiluminescent Kinase assay (LCCA) format. Kinase activity was measured as the percent ATP remaining following the kinase reaction. Remaining ATP was detected by luciferase-luciferin-coupled chemiluminescence. Specifically, the reaction was initiated by mixing test compounds, 5 μM ATP, 3 μM poly-EY and 5 nM Flt-3 (baculovirus expressed human Flt-3 kinase domain R571-S993) in a 20 uL assay buffer (20 mM Tris-HCL pH7.5, 10 mM MgCl$_2$, 0.01% Triton X-100, 1 mM DTT, 2 mM MnCl$_2$). The mixture is incubated at ambient temperature for 3 hours after which 20 uL luciferase-luciferin mix is added and the chemiluminescent signal read using a Wallac Victor$^2$ reader.

The luciferase-luciferin mix consists of 50 mM HEPES, pH 7.8, 8.5 ug/mL oxalic acid (pH 7.8), 5 (or 50) mM DTT, 0.4% Triton X-100, 0.25 mg/mL coenzyme A, 63 uM AMP, 28 ug/mL luciferin and 40,000 units of light/mL luciferase.

Structure Activity Relationships

Table 2 shows structure activity relationship data for selected compounds of the invention. Inhibition is indicated as $IC_{50}$ with the following key: $A=IC_{50}$ less than 50 nM, $B=IC_{50}$ greater than 50 nM, but less than 500 nM, $C=IC_{50}$ greater than 500 nM. Depending upon the functionality, exemplary compounds of the invention exhibit selectivity for any of c-Met, KDR, and flt-3. Abbreviations for enzymes listed in Table 2 are defined as follows: c-Met refers to hepatocyte growth factor receptor kinase; KDR refers to kinase insert domain receptor tyrosine kinase; and flt-3, fms-like tyrosine kinase-3. Empty cells in Table 2 indicate lack of data only.

TABLE 2

| Entry | Name | c-Met | KDR | flt-3 |
|---|---|---|---|---|
| 1 | N-(4-fluorophenyl)-N'-[3-fluoro-4-(7H-pyrrolo[2,3-d]pyrimidin-4-yloxy)phenyl]propanediamide | B | B | A |
| 2 | N-(4-fluorophenyl)-N'-[3-fluoro-4-(7H-pyrrolo[2,3-d]pyrimidin-4-yloxy)phenyl]cyclopropane-1,1-dicarboxamide | A | A | B |
| 3 | N-({[3-fluoro-4-(7H-pyrrolo[2,3-d]pyrimidin-4-yloxy)phenyl]amino}carbonothioyl)-2-phenylacetamide | A | B | C |
| 4 | N-(4-fluorophenyl)-N'-(4-{[1-(tetrahydro-2H-pyran-2-yl)-1H-pyrazolo[3,4-d]pyrimidin-4-yl]oxy}phenyl)cyclopropane-1,1-dicarboxamide | C | C | |
| 5 | 2-phenyl-N-{[(4-{[1-(tetrahydro-2H-pyran-2-yl)-1H-pyrazolo[3,4-d]pyrimidin-4-yl]oxy}phenyl)amino]carbonothioyl}acetamide | C | C | |
| 6 | N-(4-fluorophenyl)-N'-[4-(1H-pyrazolo[3,4-d]pyrimidin-4-yloxy)phenyl]cyclopropane-1,1-dicarboxamide | C | B | |
| 7 | 2-phenyl-N-({[4-(1H-pyrazolo[3,4-d]pyrimidin-4-yloxy)phenyl]amino}carbonothioyl)acetamide | C | C | |
| 8 | N-(4-fluorophenyl)-N'-(4-{[9-(tetrahydro-2H-pyran-2-yl)-9H-purin-6-yl]oxy}phenyl)cyclopropane-1,1-dicarboxamide | C | C | |
| 9 | 2-phenyl-N-{[(4-{[9-(tetrahydro-2H-pyran-2-yl)-9H-purin-6-yl]oxy}phenyl)amino]carbonothioyl}acetamide | C | C | |
| 10 | N-(4-fluorophenyl)-N'-[4-(9H-purin-6-yloxy)phenyl]cyclopropane-1,1-dicarboxamide | C | C | |
| 11 | 2-phenyl-N-({[4-(9H-purin-6-yloxy)phenyl]amino}carbonothioyl)acetamide | C | C | |
| 12 | N-{3-fluoro-4-[(6-{[(2-morpholin-4-ylethyl)amino]carbonyl}-7H-pyrrolo[2,3-d]pyrimidin-4-yl)oxy]phenyl}-N'-(4-fluorophenyl)cyclopropane-1,1-dicarboxamide | A | A | A |

What is claimed is:

1. A compound of formula Vc:

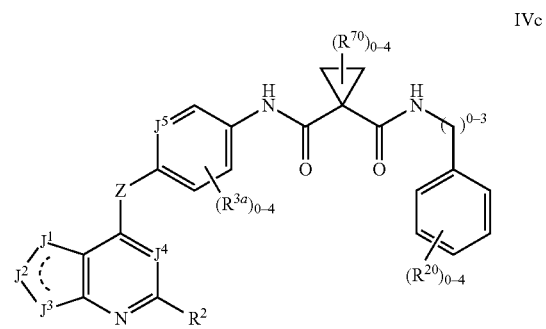

IVc wherein:

$J^1$ is =CH—;

$J^2$ is =C($R^1$)—;

$J^3$ is =N—;

$J^4$ is =N—;

$J^5$ is C—H or C—F;

Z is O;

$R^1$ is independently selected from halogen, trihalomethyl, —CN, —NO$_2$, —OR$^{20}$, —N(R$^{20}$)R$^{20}$, —S(O)$_{0-2}$R$^{20}$, —SO$_2$N(R$^{20}$)R$^{20}$, —CO$_2$R$^{20}$, —C(O)N(R$^{20}$)R$^{20}$, —N(R$^{20}$)SO$_2$R$^{20}$, —N(R$^{20}$)C(O)R$^{20}$, —NHCO$_2$R$^{20}$, —C(O)R$^{20}$, optionally substituted C$_{1-6}$alkyl, optionally substituted aryl, optionally substituted aryl C$_{1-6}$alkyl optionally substituted heterocyclyl, and optionally substituted heterocyclyl C$_{1-6}$alkyl;

$R^2$ is H;

each $R^{3a}$ is independently selected from —H, halogen, trihalomethyl, —CN, —NO$_2$, —OR$^{20}$, —N(R$^{20}$)R$^{20}$, —S(O)$_{0-2}$R$^{20}$, —SO$_2$N(R$^{20}$)R$^{20}$, —CO$_2$R$^{20}$, —C(O)N(R$^{20}$)R$^{20}$, —N(R$^{20}$)SO$_2$R$^{20}$, —N(R$^{20}$)C(O)R$^{20}$, —NHCO$_2$R$^{20}$, —C(O)R$^{20}$, optionally substituted C$_{1-6}$alkyl, and optionally substituted heterocyclyl;

each $R^{20}$ is independently —H, optionally substituted C$_{1-6}$alkyl, optionally substituted aryl, optionally substituted aryl C$_{1-6}$alkyl, optionally substituted heterocyclyl, and optionally substituted heterocyclyl C$_{1-6}$alkyl; or two of $R^{20}$, when taken together with a common nitrogen to which they are attached, can form an optionally substituted five- to seven-membered heterocyclyl, said optionally substituted five- to seven-membered heterocyclyl optionally containing at least one additional annular heteroatom selected from N, O, S, and P; and each $R^{70}$ is independently selected from —H, halogen, trihalomethyl, —CN, —NO$_2$, —OR$^{20}$, —N(R$^{20}$)R$^{20}$, —S(O)$_{0-2}$R$^{20}$, —SO$_2$N(R$^{20}$)R$^{20}$, —CO$_2$R$^{20}$, —C(O)N(R$^{20}$)R$^{20}$, —N(R$^{20}$)SO$_2$R$^{20}$, —N(R$^{20}$)C(O)R$^{20}$, —NHCO$_2$R$^{20}$, —C(O)R$^{20}$, optionally substituted C$_{1-6}$alkyl, optionally substituted aryl, optionally substituted aryl C$_{1-6}$alkyl, optionally substituted heterocyclyl, and optionally substituted heterocyclyl C$_{1-6}$alkyl.

2. A compound selected from:

| Entry | Name | Structure |
|---|---|---|
| 2 | N-(4-fluorophenyl)-N'-[3-fluoro-4-(7H-pyrrolo[2,3-d]pyrimidin-4-yloxy)phenyl]cyclopropane-1,1-dicarboxamide | 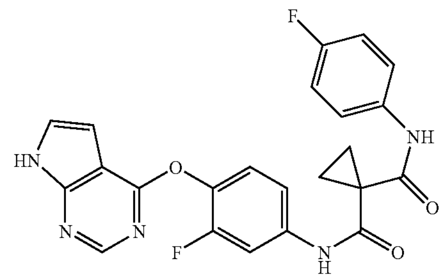 |
| 12 | N-{3-fluoro-4-[(6-{[(2-morpholin-4-ylethyl)amino]carbonyl}-7H-pyrrolo[2,3-d]pyrimidin-4-yl)oxy]phenyl}-N'-(4-fluorophenyl)cyclopropane-1,1-dicarboxamide | 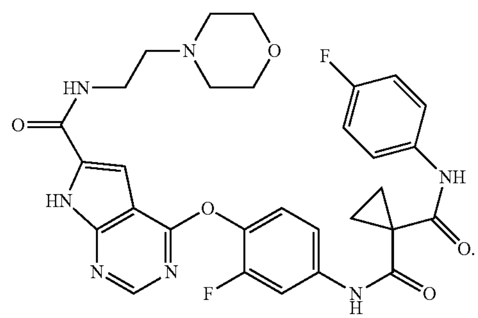 |

3. A pharmaceutical composition comprising a compound according to claim 1 or 2 and a pharmaceutically acceptable carrier.

\* \* \* \* \*